US010646271B2

(12) United States Patent
Trees et al.

(10) Patent No.: US 10,646,271 B2
(45) Date of Patent: May 12, 2020

(54) METHODS AND DEVICES FOR CONTROLLING MOTORIZED SURGICAL DEVICES

(71) Applicant: Ethicon LLC, Guaynabo, PR (US)

(72) Inventors: Gregory A. Trees, Loveland, OH (US);
Eric N. Johnson, Maineville, OH (US);
Chad P. Boudreaux, Cincinnati, OH (US); Robert Laird, Morrow, OH (US); Rudolph H. Nobis, Mason, OH (US); Geoffrey S. Strobl, Williamsburg, OH (US); Jason R. Lesko, Harrison, OH (US); John A. Hibner, Mason, OH (US); David C. Yates, West Chester, OH (US); David M. Locke, Springboro, OH (US); William B. Weisenburgh, II, Maineville, OH (US); Phillip Clauda, Blue Ash, OH (US)

(73) Assignee: Ethicon LLC, Guaynabo, PR (US)

( * ) Notice: Subject to any disclaimer, the term of this patent is extended or adjusted under 35 U.S.C. 154(b) by 332 days.

(21) Appl. No.: 15/724,629

(22) Filed: Oct. 4, 2017

(65) Prior Publication Data

US 2018/0021082 A1    Jan. 25, 2018

Related U.S. Application Data

(63) Continuation of application No. 14/166,244, filed on Jan. 28, 2014, now Pat. No. 9,801,679.

(51) Int. Cl.
*A61B 17/32* (2006.01)
*A61B 18/14* (2006.01)
(Continued)

(52) U.S. Cl.
CPC .......... *A61B 18/1445* (2013.01); *A61B 17/29* (2013.01); *A61B 2017/00022* (2013.01);
(Continued)

(58) Field of Classification Search
CPC ............ A61B 17/32; A61B 17/320016; A61B 17/32002; A61B 17/320092;
(Continued)

(56) References Cited

U.S. PATENT DOCUMENTS

| 7,422,136 | B1 | 9/2008 | Marczyk |
| 7,776,037 | B2 | 8/2010 | Odom |
| 8,128,625 | B2 | 3/2012 | Odom |
| 8,357,158 | B2 | 1/2013 | McKenna et al. |
| 8,357,160 | B2 | 1/2013 | Odom |
| 9,801,679 | B2 * | 10/2017 | Trees ................. A61B 18/1445 |

(Continued)

FOREIGN PATENT DOCUMENTS

WO    WO-2012061638 A1    5/2012

OTHER PUBLICATIONS

International Search Report and Written Opinion for PCT/US2015/011568 (18 pages).
U.S. Appl. No. 14/166,194, filed Jan. 28, 2014.

*Primary Examiner* — Melanie R Tyson
(74) *Attorney, Agent, or Firm* — Mintz Levin Cohn Ferris Glovsky and Popeo, P.C.

(57) ABSTRACT

Methods and devices for controlling motorized surgical devices are provided. In general, the methods and devices can allow a surgical device to grasp and cut tissue. In some embodiments, the device's motor can begin providing power for grasping and/or cutting tissue in response to an output from the device's sensor, the device can adjust power provided by the motor based on whether the device is clamping tissue or is being fired, the device can adjust an amount of power provided by the motor based on an amount of user-applied force to the device's actuator and/or can control drive direction of the motor based on the amount of the force, the device can maintain a force applied to the device, the device can self-shift the motor, and/or the device can adjust an amount of power provided to the device's end effector based on a degree of the end effector's closure.

20 Claims, 30 Drawing Sheets

(51) Int. Cl.
*A61B 17/29* (2006.01)
*A61B 17/00* (2006.01)
*A61B 90/00* (2016.01)

(52) U.S. Cl.
CPC .............. *A61B 2017/00119* (2013.01); *A61B 2017/00398* (2013.01); *A61B 2018/1455* (2013.01); *A61B 2090/061* (2016.02); *A61B 2090/064* (2016.02); *A61B 2090/065* (2016.02)

(58) Field of Classification Search
CPC . A61B 17/285; A61B 17/282; A61B 17/2841; A61B 17/28; A61B 17/29; A61B 2017/320072; A61B 2017/320076; A61B 2017/00398; A61B 18/1442; A61B 18/1445; A61B 2018/1455
See application file for complete search history.

(56) References Cited

U.S. PATENT DOCUMENTS

| | | |
|---|---|---|
| 2008/0039836 A1 | 2/2008 | Odom et al. |
| 2010/0217264 A1 | 8/2010 | Odom et al. |
| 2011/0082494 A1 | 4/2011 | Kerr et al. |
| 2012/0022525 A1 | 1/2012 | Dietz et al. |
| 2012/0022527 A1 | 1/2012 | Woodruff et al. |
| 2012/0022530 A1 | 1/2012 | Woodruff et al. |
| 2012/0078139 A1 | 3/2012 | Aldridge et al. |
| 2012/0078247 A1 | 3/2012 | Worrell et al. |
| 2012/0116379 A1* | 5/2012 | Yates .............. A61B 17/295 606/33 |
| 2013/0193188 A1 | 8/2013 | Shelton, IV et al. |
| 2015/0088122 A1 | 3/2015 | Jensen |
| 2015/0209573 A1 | 7/2015 | Hibner et al. |

* cited by examiner

METHODS AND DEVICES FOR CONTROLLING MOTORIZED SURGICAL DEVICES

CROSS REFERENCE TO RELATED APPLICATIONS

The present application is a continuation of U.S. patent application Ser. No. 14/166,244 entitled "Methods And Devices For Controlling Motorized Surgical Devices" filed Jan. 28, 2014, now U.S. Pat. No. 9,801,679, which is hereby incorporated by reference in its entirety.

FIELD

The present invention relates to methods and devices for controlling motorized surgical devices.

BACKGROUND

Various surgical devices are used for compressing and cutting different types of tissue. In general, these devices have jaws configured to grasp tissue and a cutting mechanism configured to be advanced through the tissue to sever it. These devices can also apply energy to the tissue disposed between the jaws to promote hemostasis.

A common concern when using any of these devices is achieving hemostasis so that bleeding of the target tissue is limited. By increasing the amount of pressure applied to the target tissue, the flow of blood can be limited, decreasing the time necessary to achieve hemostasis. However, applying too much pressure can result in an unnecessary reduction in blood flow to the tissue surrounding the cut-line, potentially resulting in an elevated level of necrosis, a slower rate of healing, and/or a greater recovery period. An optimal amount of force depends on various factors, including the type of tissue and its thickness.

Accordingly, there remains a need for improved methods and devices for controlling motorized surgical devices.

SUMMARY

A surgical device is provided that in one embodiment includes a proximal handle portion that includes a motor, an elongate shaft extending distally from the handle portion, first and second jaws at a distal end of the elongate shaft, an actuator configured to receive an input from a user that causes the motor to provide power that causes at least one of the first and second jaws to move such that a distance between the first and second jaws is reduced, a sensor, and a controller configured to determine, based on output from the sensor, an amount of the power to be provided by the motor. The first and second jaws can be configured to engage tissue therebetween. The input from the user can be selected from the group consisting of pressure, force, strain, and displacement.

The sensor can be configured to sense an amount of the input, and controller can be configured to cause the motor to begin providing the power that causes at least one of the first and second jaws to move only when the sensed amount of the input is greater than or equal to a predetermined threshold amount. In some embodiments, after the motor begins providing the power, the controller can be configured to cause the motor to cease providing the power that causes the at least one of the first and second jaws to move when the sensed amount of the input changes so as to be below the predetermined threshold amount. In some embodiments, when the sensed amount of the input is less than the predetermined threshold amount, the input can cause the at least one of the first and second jaws to move without power from the motor.

The surgical device can include a cutting element configured to move relative to the first and second jaws so as to cut the tissue engaged between the first and second jaws. The power provided by the motor can also cause the cutting element to relative to the first and second jaws. In some embodiments, the sensor can be configured to sense an amount of the input, and when the cutting element is moving proximally relative to the first and second jaws, the greater the sensed amount of the input, the lower the amount of the power can be provided by the motor and the slower the cutting element can move relative to the first and second jaws. When the cutting element is moving distally relative to the first and second jaws, the greater the sensed amount of the input, the greater the amount of the power can be provided by the motor and the faster the cutting element can move relative to the first and second jaws.

The surgical device can vary in any other number of ways. For example, the sensor can be configured to sense an amount of the input, and the sensed amount of the input can be directly proportional to the amount of power provided by the motor. For another example, the sensor can be configured to sense an amount of the input, and when the sensed amount of the input is greater than or equal to a predetermined threshold amount, the controller can be configured to cause the motor to provide the power without the user continuing to provide the input. For yet another example, the sensor can be configured to detect when the first and second jaws have been manually closed by the user, and whenever the motor is not providing the power, the first and second jaws can be configured to be manually opened by the user. For another example, the sensor can be configured to sense an amount of the input, and the controller can be configured to cause a feedback signal to be provided to the user when the sensed amount of the input is greater than or equal to a predetermined threshold amount. The feedback signal can include at least one of a light, a sound, a vibration, and a visual textual display. For yet another example, the sensor can include at least one of a strain gauge, a potentiometer, a piezoresistor, a load cell, an analog sensor, an infrared sensor, and a spring. For another example, the actuator can include a movable trigger coupled to the proximal handle portion.

In another embodiment, a surgical device is provided that includes a proximal handle portion that includes a single motor, an elongate shaft extending distally from the handle portion, and first and second jaws at a distal end of the elongate shaft. The first and second jaws can be configured to engage tissue therebetween. The motor can be configured to supply power that moves at least one of the first and second jaws so as to reduce a distance between facing sides of the first and second jaws that are configured to engage the tissue. The surgical device can also include a first actuator configured to receive a first input from a user that causes the motor to provide the power that causes the at least one of the first and second jaws to move so as to reduce the distance, and a cutting element configured to move relative to the first and second jaws so as to cut the tissue engaged between the first and second jaws. The motor can be configured to supply power that causes the cutting element to move relative to the first and second jaws. The surgical device can also include a second actuator configured to receive a second input from the user that causes the motor to provide the power that causes the cutting element to move relative to the first and second jaws. The second actuator can be prevented from receiving the second input until after the first actuator receives the first input and the at least one of the first and second jaws has moved so as to reduce the distance.

The surgical device can have any number of variations. For example, the second input can cause the cutting element to move in a first direction relative to the first and second jaws, and in response to the second actuator ceasing to receive the second input, the motor can be configured to provide power that moves the cutting element in a second direction relative to the first and second jaws. The second direction can be opposite to the first direction. For another example, in response to the first actuator ceasing to receive the first input, the motor can be configured to provide power that causes the at least one of the first and second jaws to move so as to increase the distance between the facing sides of the first and second jaws. For yet another example, the surgical device can include first and second drive members. The first drive member can be coupled to the first and second jaws and can be configured to be driven by the motor in response to the first input so as to cause the at least one of the first and second jaws to move. The second drive member can be coupled to the cutting element and can be configured to be driven by the motor in response to the second input so as to cause the cutting element to move relative to the first and second jaws. The first rack can not be driven in response to the second input, and the second rack can not be driven in response to the first input. For still another example, the surgical device can include a sensor configured to sense an amount of the first input. An amount of the power provided by the motor that causes the at least one of the first and second jaws to move can be based on the sensed amount of the first input. For another example, the surgical device can include a sensor configured to sense an amount of the second input. An amount of the power provided by the motor that causes the cutting element to move relative to the first and second jaws can be based on the sensed amount of the second input.

In another aspect, a surgical method is provided that includes engaging a tissue with first and second jaws of a surgical device, and receiving an input from a user that causes a motor of the device to provide power that causes at least one of the first and second jaws to move such that a distance between the first and second jaws is reduced. The input from the user can be selected from the group consisting of pressure, force, strain, and displacement. The method can also include, after the distance has decreased, moving a cutting element of the device through the tissue so as to cut the tissue. The method can also include sensing an amount of the input. An amount of the power provided by the motor can be based on the sensed amount of the pressure. The method can vary in any number of ways.

BRIEF DESCRIPTION OF DRAWINGS

This invention will be more fully understood from the following detailed description taken in conjunction with the accompanying drawings, in which.

DETAILED DESCRIPTION

Figure 1:
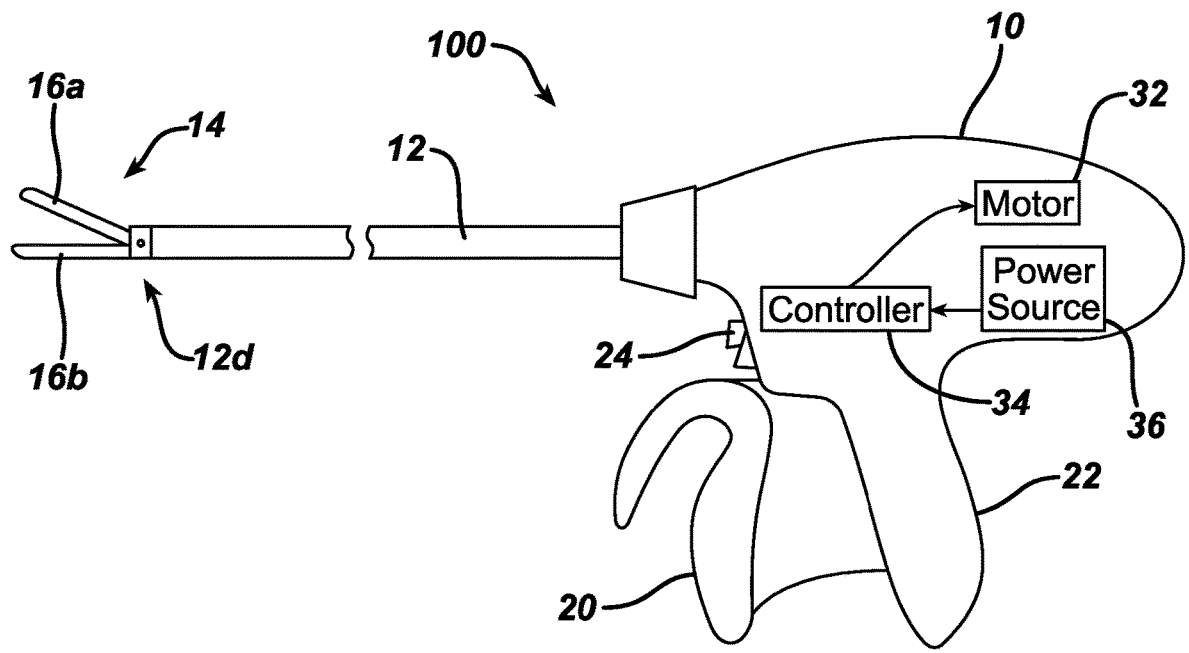
FIG. 1 is a side schematic view of an embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for controlling motorized surgical devices are provided. In general, the methods and devices can allow a surgical device to grasp and cut tissue. In some embodiments, the device can include a sensor and a motor, and the motor can be configured to begin providing power for grasping and/or cutting in response to an output from the sensor. In some embodiments, the device can be configured to adjust power provided by a motor of the device based on whether the device is clamping tissue or the device is being fired. In some embodiments, the device can be configured to adjust an amount of power provided by a motor of the device based on an amount of input force that a user applies to an actuator of the device and/or can be configured to control drive direction of the motor based on the amount of input force. In some embodiments, the device can be configured to maintain a force applied to the device when the force reaches a predetermined force. In some embodiments, the device can be configured to self-shift a motor of the device between two different speeds. In some embodiments, the device can be configured to adjust an amount of power provided to an end effector of the device based on a degree of the end effector's closure.

FIG. 1 illustrates one embodiment of a surgical device 100 configured to grasp and cut tissue. The surgical device 100 can include a proximal handle portion 10, a shaft portion 12, and an end effector 14 configured to grasp tissue. The proximal handle portion 10 can be any type of pistol-grip or other type of handle known in the art that is configured to carry various actuators, such as actuator levers, triggers or sliders, configured to actuate the end effector 14. As in the illustrated embodiment, the proximal handle portion 10 can include a closure grip 20 and a stationary grip 22. Movement of the closure grip 20 toward and away from the stationary grip 22, such as by manual movement by a hand of a user, can adjust a position of the end effector 14. The shaft portion 12 can extend distally from the proximal handle portion 10 and can have a bore (not shown) extending therethrough. The bore can carry mechanisms for actuating the end effector 14, such as a jaw closure tube and/or a drive shaft. As discussed further below, one or more sensors can be positioned on the surgical device 100 and can be configured to sense data related to an applied force on tissue manipulated by the end effector 14.

Figure 2:
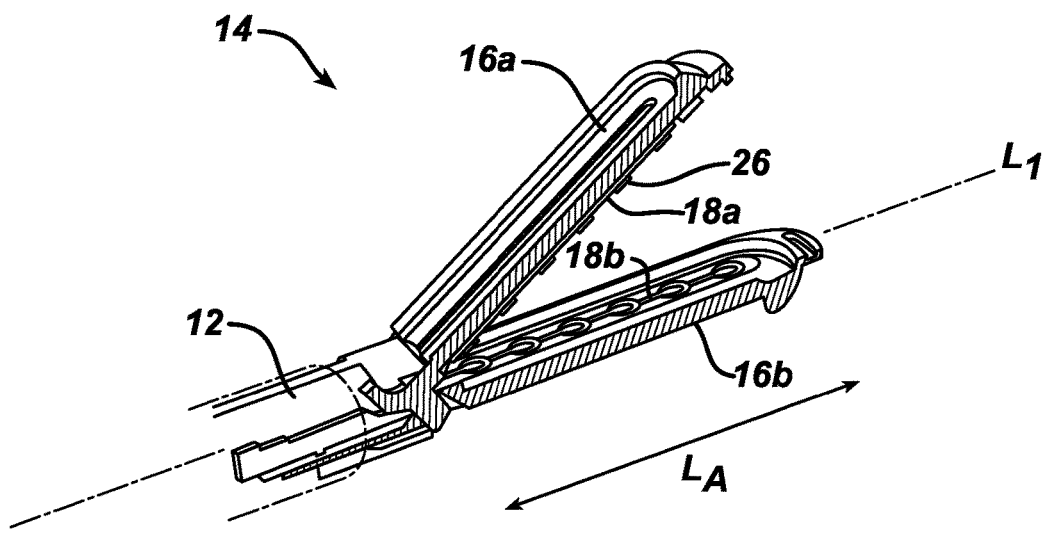
FIG. 2 is a perspective view of a distal portion of the surgical device of FIG. 1.

The end effector 14 can have a variety of sizes, shapes, and configurations. As shown in FIGS. 1 and 2, the end effector 14 can include a first, upper jaw 16a and a second, lower jaw 16b each disposed at a distal end 12d of the shaft portion 12. One or both of the upper and lower jaws 16a, 16b can be configured to close or approximate about a longitudinal axis $L_1$ of the end effector 14. Both of the jaws 16a, 16b can be moveable relative to the shaft portion 12 such that the end effector 14 can be moved between open and closed positions, or only one the upper and lower jaws 16a, 16b can be configured to move relative to the shaft portion 12 and to the other of the jaws 16a, 16b so as to move the end effector 14 between open and closed positions. When the end effector 14 is in the open position, the jaws 16a, 16b can be positioned at a distance apart from one another with a space therebetween. As discussed further below, tissue can be positioned within the space between the jaws 16a, 16b. When the end effector 14 is in the closed position, a longitudinal axis of the upper jaw 16a can be substantially parallel to a longitudinal axis of the lower jaw 16b, and the jaws 16a, 16b can be moved toward one another such that the distance therebetween is less than when the end effector 14 is in the open position. In some embodiments, facing engagement surfaces 18a, 18b of the jaws 16a, 16b can be in direct contact with one another when the end effector 14 is in the closed position such that the distance between is substantially zero. In the illustrated embodiment, the upper jaw 16a is configured to pivot relative to the shaft portion 12 and relative to the lower jaw 16b while the lower jaw 16b remains stationary. In the illustrated embodiment, the jaws 16a, 16b have a substantially elongate and straight shape, but a person skilled in the art will appreciate that one or both of the jaws 16a, 16b can be curved along the longitudinal axis $L_1$ of the end effector 14. The longitudinal axis $L_1$ of the end effector 14 can be parallel to and coaxial with a longitudinal axis of the shaft portion 12 at least when the end effector 14 is in the closed configuration, and if the end effector 14 is configured to articulate relative to the shaft portion 12, when the end effector 14 is not articulated relative to the shaft portion 12.

The jaws 16a, 16b can have any suitable axial length $L_A$ for engaging tissue, where the axial length $L_A$ is measured along the longitudinal axis $L_1$ of the end effector 14, as shown in FIG. 2. The axial length $L_A$ of the jaws 16a, 16b can also be selected based on the targeted anatomical structure for transection and/or sealing. If an exemplary embodiment, the jaws 16a, 16b have a substantially equal axial length $L_A$.

The jaws 16a, 16b can have any number and any combination of features configured to facilitate grasping tissue between the facing surfaces 18a, 18b of the jaws 16a, 16b. The first and second engagement surfaces 18a, 18b can each be configured to directly contact tissue. Either one or both of the engagement surfaces 18a, 18b can include one or more surface features formed thereon that can help secure the tissue thereon. The one or more surface features can facilitate grasping of tissue, can be configured to increase friction between the tissue and the engagement surfaces 18a, 18b of the jaws 16a, 16b without tearing or otherwise damaging the tissue in contact with such surface features, and/or can facilitate forming substantially smooth, uniform layers of tissue to improve tissue effect. Examples of the surface features can include teeth, ridges, and depressions. In the illustrated embodiment, as shown in FIG. 2, the jaws 16a, 16b each include a plurality of teeth 26 positioned along an axial length of both of the engagement surfaces 18a, 18b.

One or both of the first and second jaws 16a, 16b can include one or more features configured to interact with a compression member (not shown) configured to apply compressive forces on tissue. For example, the first and second jaws 16a, 16b can include first and second recessed slots (not shown) that can receive portions of a compression member and act as a track to direct movement of the compression member. As another example, the first and second recessed slots can be configured to receive portions of a cutting member, as discussed further below.

Figure 3:
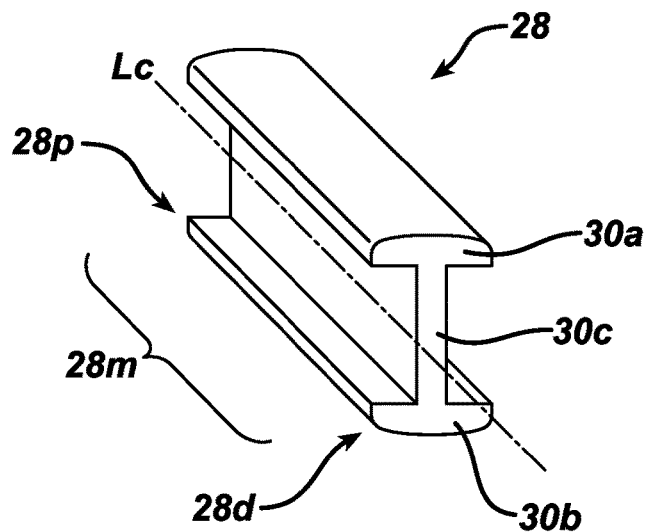
FIG. 3 is a perspective view of a compression member of the surgical device of FIG. 1.

The compression member can have various sizes, shapes, and configurations. The compression member can have an elongate shape and can be moveable proximally and distally along the longitudinal axis $L_1$ of the end effector 14. One embodiment of a compression member 28 is illustrated in FIG. 3. As shown, the compression member 28 can have a proximal end 28p, a distal end 28d, and a medial portion 28m extending therebetween. The proximal end 28p and the medial portion 28m of the compression member 28 can be sized and shaped to reciprocate within the shaft portion 12 of the device 100. The distal end 28d of the compression member 28 can be sized and shaped to interact with the jaws 16a, 16b of the end effector 14. A longitudinal axis $L_C$ of the compression member 28 can be parallel to and coaxial with the longitudinal axis $L_1$ of the end effector 14, though other configurations are possible. The compression member 28 can be actuatable from the proximal handle portion 10 of the device 100 by a first, firing actuator 24 that is operatively coupled to the proximal end 28p of the compression member 28, such as via a depressible button 24, shown in FIG. 1. Other examples of the firing actuator that can actuate the compression member include a lever, a knob, a switch, and a trigger. In general, the firing actuator 24 can be configured to be manually manipulated by a user to cause actuation of one or more other device elements, such as the compression member 28.

The compression member 28 can include a connecting portion 30c and upper and lower flanges 30a, 30b, thus providing an "I" cross-sectional shape for the compression member 28. As on the illustrated embodiment, the upper and lower flanges 30a, 30b can be positioned substantially perpendicular to the connecting portion 30c to form the "I" cross-sectional shape. The upper and lower flanges 30a, 30b can be sized and shaped to allow the upper and lower flanges 30a, 30b to slide in the recessed slots in the upper and lower jaw 16a, 16b, respectively. This sliding contact of lateral edges of the flanges 30a, 30b and sides of each of the recessed slots can prevent lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the end effector 14.

The compression member 28 can form a distal tip of a drive shaft that moves through the end effector 14 such that only a distal portion of the drive shaft includes the compression member 28. A longitudinal length of the compression member 28 can be less than a longitudinal length of the end effector 14 such that the distal tip that includes the compression member 28 can move through the end effector 14 without the compression member 28 extending along the entire longitudinal length of the end effector 14. Alternatively, the compression member 28 can be along an entire longitudinal length of the drive shaft. The compression member 28 can thus extend along the end effector's entire longitudinal length when the compression member 28 is in its distal-most position relative to the end effector 14.

The device 100 can include a cutting element (not shown) configured to cut tissue captured between the jaws 16a, 16b. The cutting element can have various sizes, shapes, and configurations. Examples of the cutting element include a knife blade and a sharp edge. The cutting element can be sized and shaped to cut various thicknesses and types of tissue positioned between the jaws 16a, 16b of the end effector 14. In an exemplary embodiment, the cutting element can be positioned at the distal end 28d of the compression member 28, such as by being formed on the connecting portion 30c of the compression member 28 as an integral part thereof, e.g., as a sharpened edge thereof, or as a member attached thereto, e.g., a blade mounted thereon. The cutting element can have a sharp or serrated edge configured to transect tissue. In an exemplary embodiment, the cutting element can be recessed relative to distal ends of upper and lower flanges 30a, 30b of the compression member 28, which can allow compression to occur prior to the cutting element cutting tissue as the compression member 28 traverses through the jaws 16a, 16b. In another embodiment, the cutting element can be configured such that it is not attached to the compression member 28, such that the cutting element can be configured to advance and retract relative to the jaws 16a, 16b so as to cut tissue sandwiched therebetween without applying compression to the tissue. In this embodiment, the device 100 can include a separate compression member so that tissue engaged by the jaws 16a, 16b can still be compressed.

The surgical device 100 can include a second, closure actuator configured to open and close the jaws 16a, 16b of the end effector 14. Manipulation of the closure actuator, e.g., manual manipulation by a user, can cause the end effector 14 to move between the open and closed positions. In other words, manipulation of the closure actuator can cause one or both of the jaws 16a, 16b to pivot or otherwise move, as discussed above, so as to allow the jaws 16a, 16b to engage tissue, move anatomical structures, and/or perform other surgical functions. The closure actuator can have various sizes, shapes, and configurations. As in the illustrated embodiment, the closure actuator can include the closure grip 20 and the stationary grip 22. The closure grip 20 can be moveable toward and away from stationary grip 22, such as via pivoting. The closure grip 20 can have a first position in which the closure grip 20 is angularly offset from the stationary grip 22 and in which the jaws 16a, 16b are open. The closure grip 20 can have a second position that is different from the first position and in which the closure grip 20 is positioned adjacent to or substantially in contact with the stationary grip 22 and in which the jaws 16a, 16b can engage tissue and apply a force to tissue disposed therebetween. The closure grip 20 can be biased to the first position with the jaws 16a, 16b being open, as shown in FIG. 1.

The closure grip 20 can be configured to move the jaws 16a, 16b between the open and closed positions using manual or powered components. In a manually actuated embodiment, the closure grip 20 can be coupled to a gear that interacts with a rack extending in the handle portion 10, and manual movement of the closure grip 20 toward the stationary grip 22 can move the rack distally toward the end effector 14, causing a force to be exerted onto the jaws 16a, 16b to close the jaws 16a, 16b. In a powered embodiment, as shown in the illustrated embodiment of FIG. 1, the device 100 can include a motor 32, a controller 34, and a power source 36. The motor 32, the controller 34, and the power source 36 can be disposed in the proximal handle portion 10. As will be appreciated by a person skilled in the art, the motor 32 can include any type of motor (e.g., a rotary motor, etc.) configured for use with a surgical device, the controller 34 can include a variety of devices configured to process signals (e.g., a microprocessor, a central processing unit (CPU), a memory controller, etc.), and the power source 36 can include a variety of devices configured to supply power to at least the controller 34 (e.g., a battery, etc.). In some embodiments, the power source can be off-board instead of on-board the device 100, such as by the device 100 being attachable via wired connection to an electrical outlet or other power source. A manual movement of the closure grip 20 can be configured to cause the controller 34 to transmit a control signal to the motor 32, which can cause the jaws 16a, 16b to close via movement of the compression member 28. The closure grip 20 can interact with one or more locking features (not shown) configured to lock the closure grip 20 relative to the stationary grip 22. For example, the one or more locking features can automatically engage when the closure grip 20 substantially contacts the stationary grip 22, or the locking feature can automatically engage at each position the closure grip 20 is pivoted through, such as via ratcheting.

The firing and closure actuators can cooperate to allow selective firing and closing of the device 100. The firing actuator 24 can be configured to be actuated to advance the cutting element through the end effector 14, apply energy to tissue, or both. Depressing or pivoting the firing actuator 25 can activate various elements in the device, and thereby cause one or more actions such as the compression member 28 and/or the cutting element advancing distally relative to the jaws 16a, 16b, and/or the compression member 28 and/or the cutting element retracting proximally relative to the jaws 16a, 16b, and/or energy being delivered to the jaws 16a, 16b. The firing actuator 24 can be in electrical communication with the motor 32. The motor 32 can be operatively coupled to the compression member 28 using e.g., a gear and rack. As in this illustrated embodiment, activation of the motor 32 can cause advancement and/or retraction of the compression member 28.

Tissue can be difficult for the jaws 16a, 16b to securely grasp and/or for the cutting element to cut, such as if the tissue is thick, tough, irradiated, and/or calcified. The tissue may thus not be able to be grasped and/or cut easily, or at all, if the compression member 28 and the cutting element are advanced through the jaws 16a, 16b using manual power alone, e.g., if the compression member 28 and the cutting element are advanced through the jaws 16a, 16b in response to the user's manual manipulation of a trigger handle. The motor 32 can be configured to supplement force applied by the user to the closure grip 20 and/or the firing actuator 24 so as to facilitate clamping and/or cutting tissue grasped by the jaws 16a, 16b. In some embodiments, the motor 32 can provide all force used to clamp and/or cut tissue grasped by the jaws 16a, 16b in response to the user's actuation of an actuator such as the closure grip 20 or the firing actuator 24. In this way, the tissue can be clamped and cut without the user having to uncomfortably apply force, e.g., if the user's hands are small such that the user cannot easily close the closure grip 20 with adequate force to clamp and/or cut the tissue, and/or without the user having to strain to apply adequate force, e.g., if the user's hand is not strong enough to squeeze the closure grip 20 tightly enough to apply adequate clamping and/or cutting force. Even when tissue is sufficiently thin and/or tender that manual power could clamp and/or cut the tissue, the motor 32 providing some or all power to clamp and/or cut the tissue can relieve the user of strain. This can help reduce user discomfort, e.g., hand pain, that can result from repeated clamping and cutting that is performed during a single procedure and/or that is performed in a series of surgical procedures performed by the same user.

The device 100 can include a sensor (not shown), and the motor 32 can be configured to begin providing power in response to an output from the sensor. The controller 34 can be configured to determine an amount of power to be provided by the motor 32. The controller 34 can be configured to receive an output signal from the sensor, and based on the output signal from the sensor, cause the motor 32 to begin providing the power, e.g., to increase the motor's provided amount power from zero.

Figure 4:
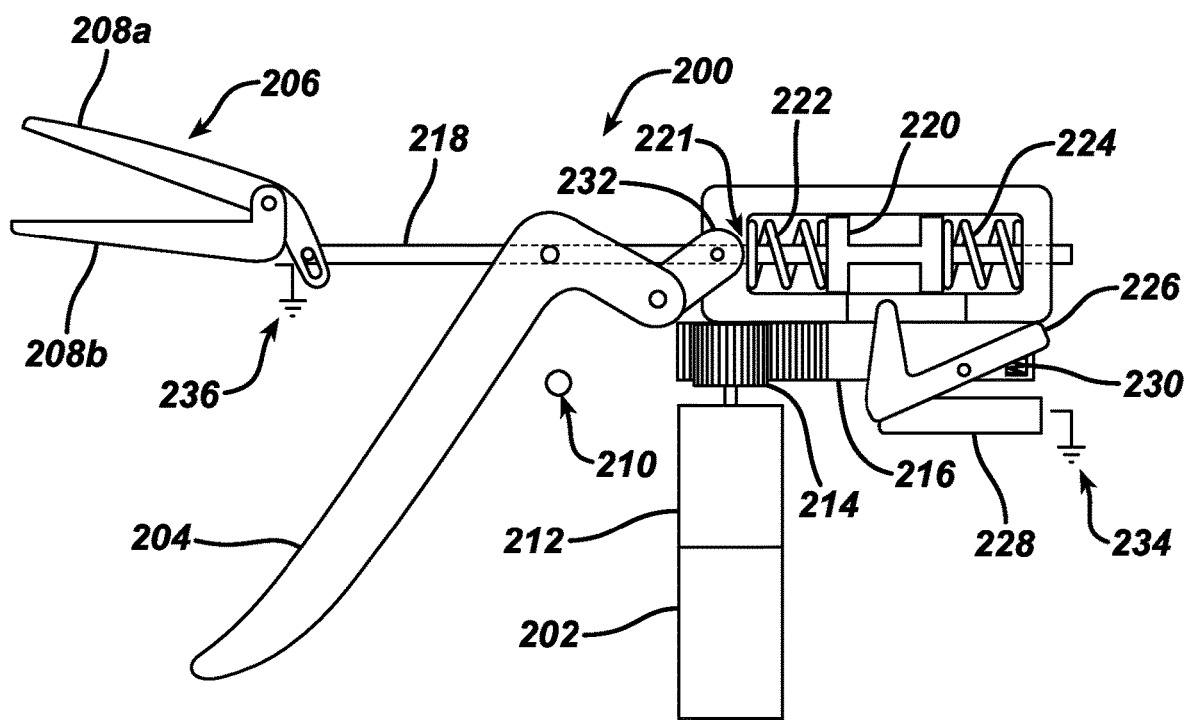
FIG. 4 is a side schematic view of an embodiment of a surgical device configured to begin providing power in response to an output from a sensor.

FIG. 4 illustrates an embodiment of a surgical device 200 configured to begin providing power in response to an output from a sensor. The device 200 can generally be configured similar to the device 100 of FIG. 1. The device 200 can include a motor 202, a closure trigger (also referred to herein as a "closure grip") 204, a firing actuator (not shown), a controller (not shown), a power source (not shown), and an end effector 206 that includes a pair of jaws 208a, 208b. The jaws 208a, 208b can be pivotally coupled together, as shown in FIG. 4. The device 200 can also include a sensor 210 configured to be actuated by the closure trigger 204, a gear box 212 that can have the controller and the power source disposed therein and that can be coupled to a gear 214, a toothed rack 216 engaged with the gear 214, a yoke 220 coupled to the rack 216, to a first, distal spring 222, and to a second, proximal spring 224, a ratchet 226 coupled to the rack 216, a ramp 228 configured to engage the ratchet 226 and cause movement thereof, a third, bias spring 230 coupled to the ratchet 226 and biasing the ratchet 226 to a first position, a jaw closure rod 218 having a distal portion coupled to the first jaw 208a and a proximal portion coupled to the yoke 220, and a closure link 232 having a distal end pivotally coupled to a proximal end of the closure trigger 204 and a proximal end pivotally coupled to a spring, such as a spring cage 221 as in the illustrated embodiment. When the closure trigger 204 is closed, the closure link 232 can push the spring cage 221 proximally, thereby compressing the first spring 222, which forces the yoke 220 proximally so as to close the jaws 208a, 208b via the jaw closure rod 218. The compression member can be coupled to a distal end of the jaw closure rod 218 and can be configured to move proximally and distally through the end effector 206 in accordance with movement of the jaw closure rod 218 proximally and distally, as discussed further below. The device 200 can also include a handle housing (not shown) configured to be handheld and that houses various elements of the device 200 therein, the yoke 220, the springs 222, 224, the ratchet 226, and the ramp 228, as will be appreciated by a person skilled in the art. As will also be appreciated by a person skilled in the art, the handle housing can include a stationary handle, and the device 220 can include a tubular elongate shaft (not shown) extending from the handle housing that has the jaw closure rod 218 extending through a passageway thereof. A first ground symbol 234 in FIG. 4 indicates that the ramp 228 can be attached to the handle housing, and a second ground symbol 236 in FIG. 4 indicates that the second jaw 208b can be attached to the elongate shaft.

The device 200 can include a locking member (not shown) configured to lock the closure trigger 204 in position when the closure trigger 204 has engaged the switch 210. The locking member can have a variety of configurations, as will be appreciated by a person skilled in the art.

The device 200 in this illustrated embodiment can be configured to provide radiofrequency (RF) energy to tissue clamped between the jaws 208a, 208b. The firing actuator can be configured to cause application of the RF energy. The RF energy can be applied in a variety of ways, as will be appreciated by a person skilled in the art. Examples of applying RF energy are described further in US Pat. Pub. No. 2012/0078139 entitled "Surgical Generator For Ultrasonic And Electrosurgical Devices" filed Oct. 3, 2011, US Pat. Pub. No. 2012/0116379 entitled "Motor Driven Electrosurgical Device With Mechanical And Electrical Feedback" filed Jun. 2, 2011, and U.S. application Ser. No. 14/166,194 entitled "Surgical Devices Having Controlled Tissue Cutting And Sealing" filed on Jan. 28, 2014, which are hereby incorporated by reference in their entireties.

In this illustrated embodiment, the sensor 210 includes a position switch, although the sensor 210 can be another type of switch, a hall effect sensor, an optical sensor, or any other sensor, as will be appreciated by a person skilled in the art. The sensor 210 can be attached to the housing in any way, e.g., adhesive, welding, snap fits, screws, etc., such that at least a portion of the sensor 210 can be located outside the housing so as to be actuatable by the closure trigger 204, as discussed further below.

Figure 5:
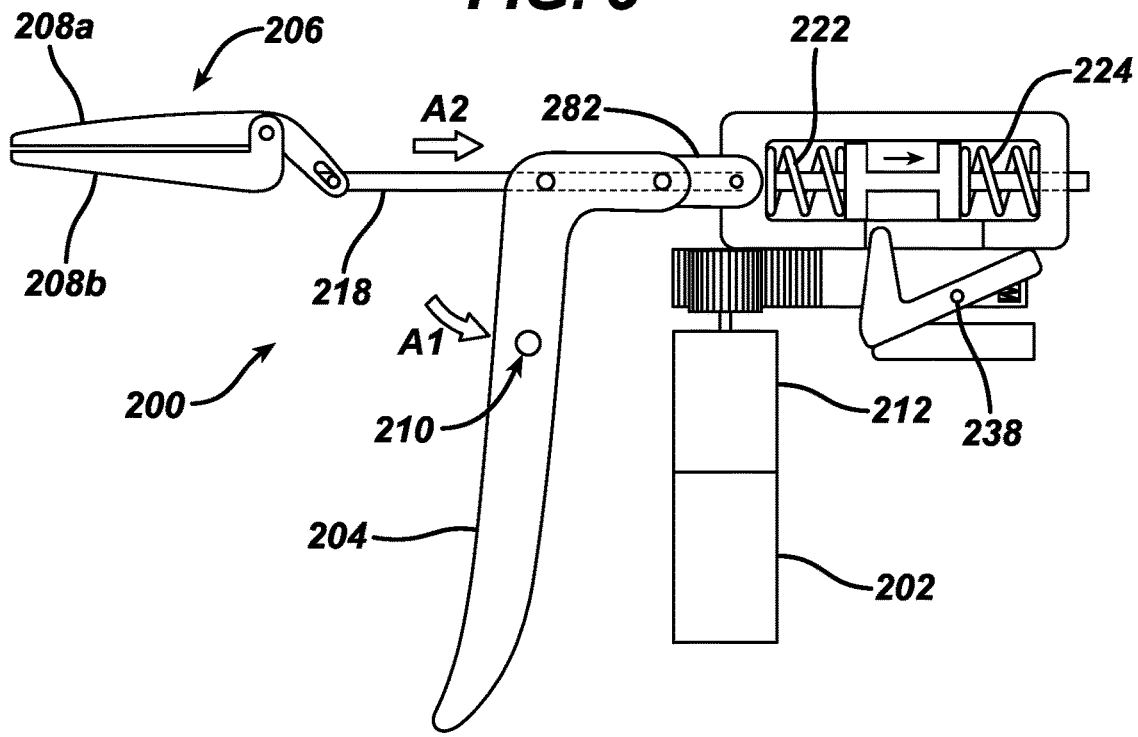
FIG. 5 is a side schematic view of the surgical device of FIG. 4 moved from a position of the surgical device in FIG. 4.
Figure 6:
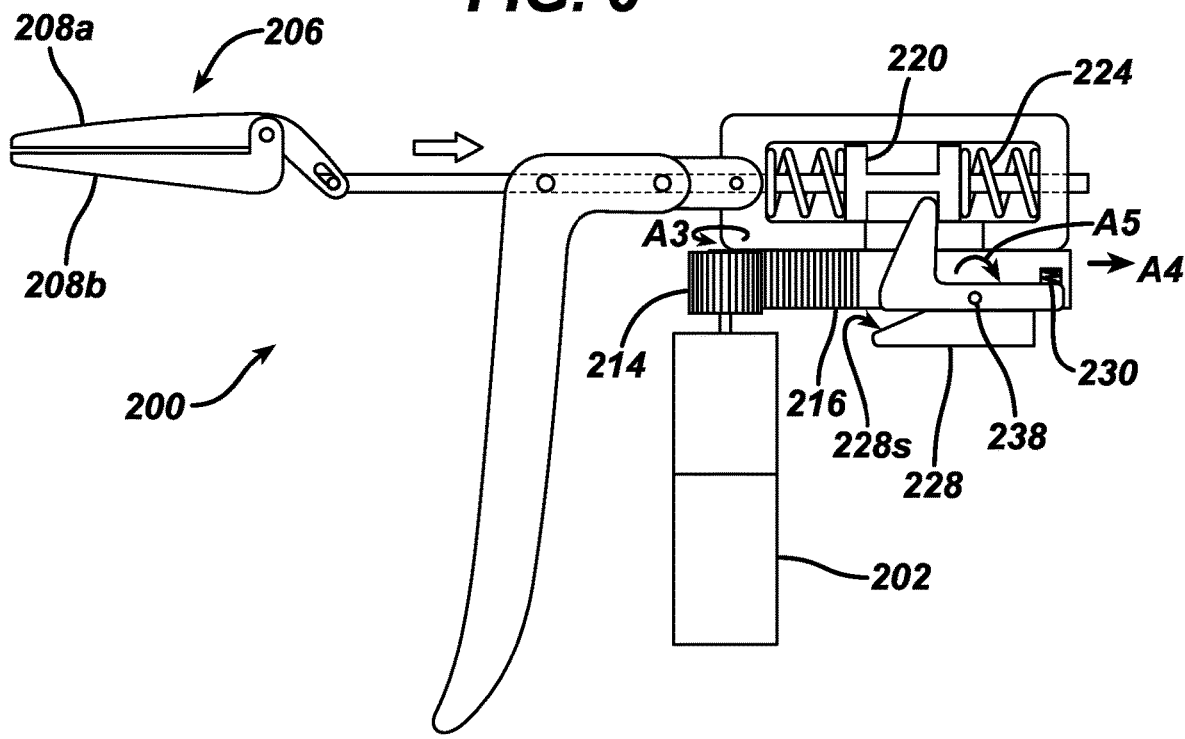
FIG. 6 is a side schematic view of the surgical device of FIG. 5 moved from a position of the surgical device in FIG. 5.

As discussed further below, FIG. 4 shows the device 200 in a first position in which the motor 202 is off and in which the end effector 206 is in an open position with the jaws 208a, 208b being open with a distance of space therebetween, FIG. 5 shows the device 200 in a second position moved from the first position in which the motor 202 is triggered on and in which the end effector 206 is in a closed position with the jaws 208a, 208b closed, and FIG. 6 shows the device 200 in a third position moved from the second position which the end effector 206 is in the closed position and in which the motor 202 has caused movement of the rack 216, thereby causing the jaw closure rod 218 to move proximally relative to the end effector 206.

When the device 200 is in the first position, as shown in FIG. 4, the closure trigger 204 and the closure link 232 are in initial positions in which the closure trigger 204 is not engaged with the sensor 210 and in which a longitudinal axis of the closure link 232 and a longitudinal axis of a proximal portion of the closure trigger 204 between attachments points thereof to the jaw closure rod 218 and the closure link 232 are offset from a longitudinal axis of the jaw closure rod 218. The longitudinal axis of the jaw closure rod 218 is parallel to and optionally coaxial with a longitudinal axis of the device's elongate shaft.

When the closure grip 204 is actuated, e.g., manually pulled proximally by a user's hand as shown by first arrow A1 in FIG. 5, the jaws 208a, 208b can be closed, and the closure trigger 204 can activate the sensor 210, e.g., by pushing down thereon as the closure trigger 204 is pulled toward the handle housing from which the sensor 210 extends. If the sensor 210 is not a position switch, as mentioned above, the sensor 210 can be configured to be activated in another way, such as by being within a certain threshold distance of the closure trigger 204, as with a Hall sensor. Moving the closure trigger 204 can cause the jaws 208a, 208b to close by the jaw closure rod 218 being moved proximally in a direction of second arrow A2 due to the proximal movement of the yoke 220, as discussed above. The jaw closure rod's proximal movement can pivot the first jaw 208a relative to the second jaw 208b so as to close the jaws 208a, 208b. The first spring 222 can provide for the proximal movement of the jaw closure rod 218 by allowing the spring cage 221 to compress the first spring 222 as the closure trigger 204 is pulled proximally so as to make substantially parallel the longitudinal axes of the closure link 232, the proximal portion of the closure trigger 204, and the jaw closure rod 218. The user can "feel" the closure of the jaws 208a, 208b since the jaws 208a, 208b are being closed under manual, user power. This "feel" can allow for a better user experience by allowing the user to know that the end effector 206 is being closed, even if the end effector 206 is only partially visible or is not visible at all during end effector closure.

The activation of the sensor 210 can cause the sensor 210 to transmit a signal to the controller that indicates activation of the sensor 210. The sensor 210 being activated can indicate to the controller that the motor 202 can be turned on since the end effector 206 has been closed by actuation of the closure trigger 204.

The device 200 can be configured to prevent the RF energy from being applied until the sensor 210 is activated. In other words, until the sensor 210 is activated by closure of the closure trigger 204 so as to close the end effector 206, the RF energy cannot be activated, even if the firing actuator is actuated. This can help provide safety by preventing the RF energy from being applied and possibly damaging material near the jaws 208a, 208b before tissue to have the RF energy applied thereto is clamped between the jaws 208a, 208b.

When the firing actuator is actuated, e.g., a button is pressed by a user, a second trigger is pulled by a user, etc., the controller can be configured to confirm that the sensor 210 has been activated before the RF energy is applied. When the controller has confirmed the activation of the sensor 210, the controller can cause the motor 202 to turn on so as to begin moving the rack 216. In general, the motor 202 being turned on can allow further closure of the end effector 206, allow for the jaws 208a, 208b to move closer together so as to more securely grasp tissue held therebetween. A load applied to the tissue by the end effector 206 can be greater when the motor 202 applies closure force than a load applied to the tissue by the end effector 206 prior to motor activation. The further closure of end effector 206 via the motor 202 can help compress the tissue between the jaws 208a, 208b and allow the RF energy to be more pointedly directed to the tissue between the jaws 208a, 208b, can allow the user to provide a comfortable amount of force to the closure trigger 204 with the motor 202 providing additional closure of the end effector 206 that may be difficult for at least some users to comfortably apply manually, and/or can help prevent the RF energy from being applied to tissue before the jaws 208a, 208b have been sufficiently closed. The motor 202 being turned on can cause the gear 214 to begin rotating, as shown by arrow R3 in FIG. 6. The gear's rotation can move the rack 216 proximally, as shown by a fourth arrow A4 in FIG. 6, thereby causing the ratchet 226 attached to the rack 216 to also move proximally. The ramp 228 can have a sloped surface 228s that the ratchet 226 engages prior to powering up of the motor 202, as shown in FIGS. 4 and 5. The bias spring 230 can bias the ratchet 226 to be in contact with the sloped surface 228s, as also shown in FIGS. 4 and 5. The proximal movement of the ratchet 226 can cause the ratchet 226 to slide along the sloped surface 228s and rotate clockwise about a pivot point 238, as shown by fifth arrow A5 in FIG. 6, at which the ratchet 226 can be attached to the rack 216. The rotation of the ratchet 226 can cause the ratchet 226 to engage the yoke 220, as shown in FIG. 6, and move the yoke 220 proximally. The proximal movement of the yoke 220 can cause the jaw closure rod 218 to move proximally, thereby causing further closure of the jaws 208a, 208b.

As mentioned above, the RF energy can be applied in response to actuation of the firing actuator. The RF energy can be applied while the motor 202 is causing the end effector 206 to further close, or the RF energy can be applied after the rack 216 has been moved proximally as much as possible by the gear 214. In an exemplary embodiment, the RF energy can be applied while the motor 202 is causing the end effector 206 to further close, and the RF energy can cease after a predetermined RF threshold is reached as determined by the controller, such as passage of a predetermined amount of time or measurement of a predetermined tissue impedance using an impedance sensor (not shown) coupled to the end effector 206. The motor 202 can be configured to power the gear 214 rotation until a predetermined threshold is reached as determined by the controller, such as passage of a predetermined amount of time, measurement of a predetermined amount of torque using a torque sensor (not shown) coupled to the gear 214, or measurement of a predetermined amount of movement. The controller can be configured to adjust an amount of the power provided to the gear 214 by the motor 202 so as to control a speed of the gear's rotation, and hence an amount of the jaw closure rod's proximal movement and accordant end effector closure, based on one or more factors such as the sensed tissue impedance and the sensed torque.

In an exemplary embodiment, the RF energy can be applied until the first of the predetermined RF threshold being reached as determined by the controller or the firing actuator being released by the user. If the firing actuator is released by the user, the controller can, in response, cause the motor 202 to stop causing closure of the jaws 208a, 208b. The controller can cause the motor 202 to rotate the gear 214 in an opposite direction to which the gear 214 was rotating, e.g., change the gear 214 from rotating clockwise to rotating counterclockwise, thereby causing the rack 216 to move distally. The distal movement of the rack 216 can cause the ratchet 226 to pivot about its pivot point 238 and to disengage from the yoke 220, which can allow the jaw closure rod 218 to move distally and for the jaws 208a, 208b to be opened manually. The manual opening of the jaws 208a, 208b can allow for the tissue engaged therebetween to be released and/or readjusted at the user's discretion. The second spring 224 can be configured to allow the jaws 208a, 208b to open more easily when the user releases the closure trigger 204 by providing a distally directed force.

The device 200 can include a safety mechanism (not shown) for the unexpected situation of failure of the motor 202. The safety mechanism can allow the jaws 208a, 208b to be opened in the event of motor failure. The controller can be configured to determine motor failure and can be configured to engage the safety mechanism in the event that motor failure is determined. The safety mechanism can include, for example, a lever arm configured to push the gear 214 out of engagement with the teeth of the rack 216. For another example, the safety mechanism can include a lever arm configured to move off the ramp 228 such that the ratchet 226 disengages from the ramp 228 and consequently disengages from the yoke 220.

Figure 7:
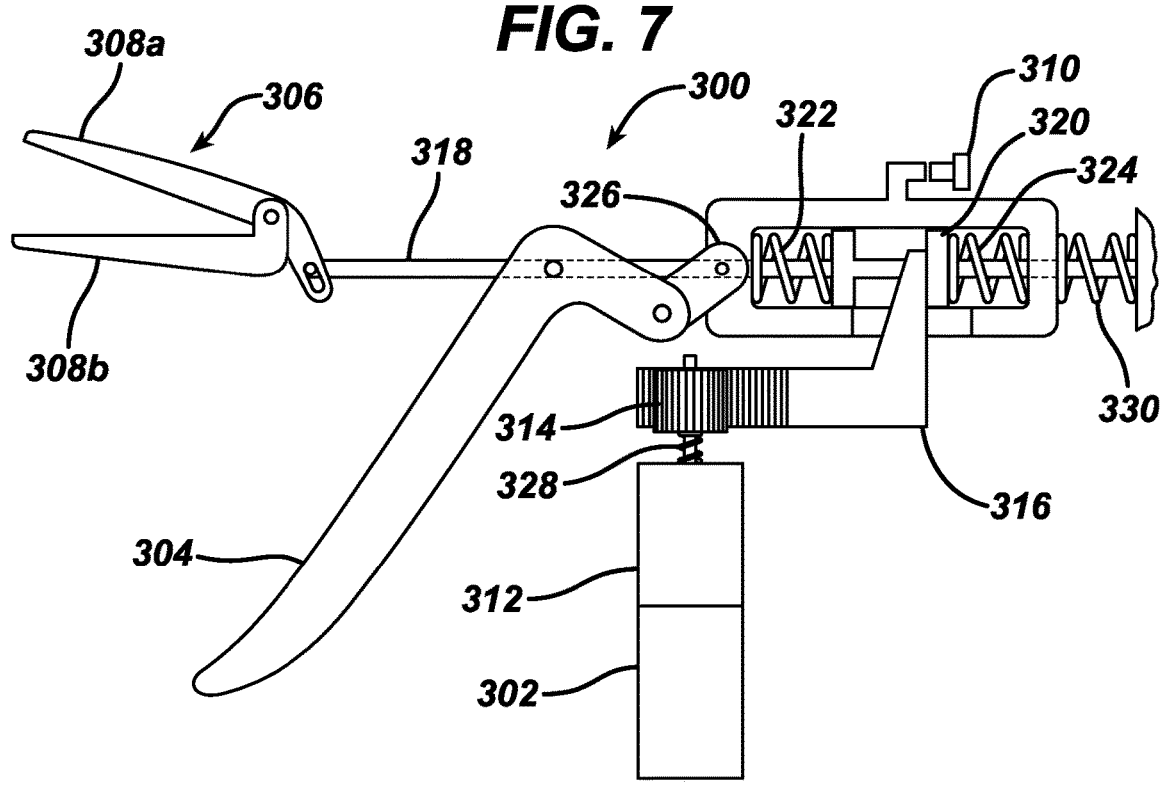
FIG. 7 is a side schematic view of another embodiment of a surgical device configured to begin providing power in response to an output from a sensor.

FIG. 7 illustrates another embodiment of a surgical device 300 configured to begin providing power in response to an output from a sensor. The device 300 can generally be configured similar to the device 200 of FIGS. 4-6. The device 300 can move between a first position, shown in FIG. 7, to a second position, shown in FIG. 8, and to a third position, shown in FIG. 9, similar to the movement of the device 200 described with respect to FIGS. 4-6. The device 300 can include a motor 302, a closure trigger 304, a firing actuator (not shown), a controller (not shown), a power source (not shown), an end effector 306 that includes a pair of jaws 308a, 308b, a sensor 310, a gear box 312, a gear 314, a toothed rack 316, a jaw closure rod 318, a yoke 320, a first, distal spring 322, a second, proximal spring 324, a closure link 326, a motor safety spring 328, and a bias spring 330.

Figure 8:
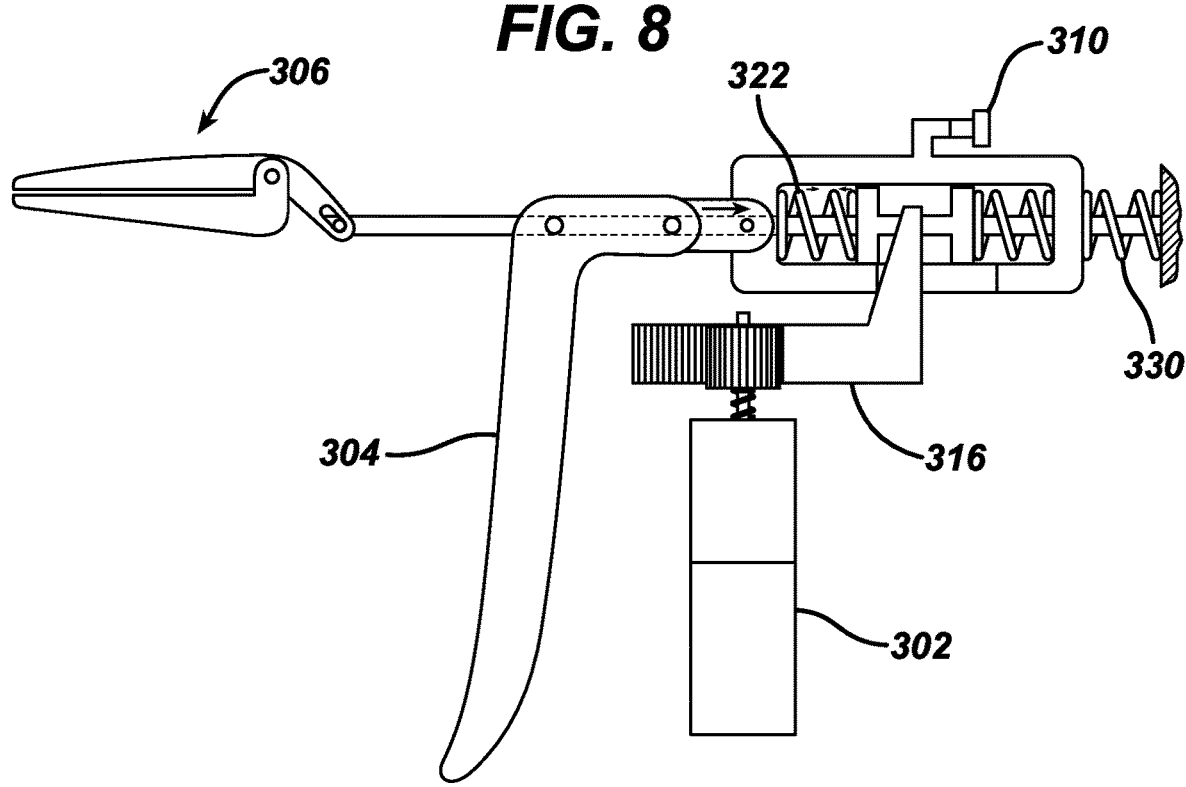
FIG. 8 is a side schematic view of the surgical device of FIG. 7 moved from a position of the surgical device in FIG. 7.
Figure 9:
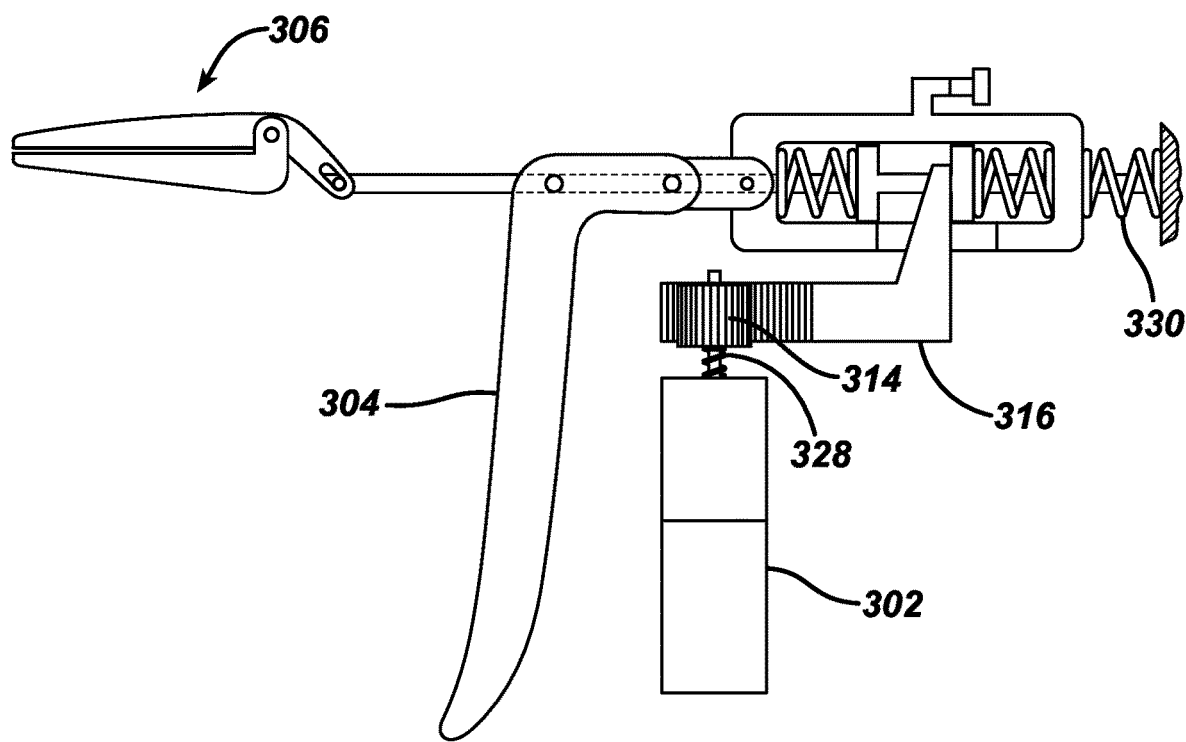
FIG. 9 is a side schematic view of the surgical device of FIG. 8 moved from a position of the surgical device in FIG. 8.

In this illustrated embodiment, the rack 316 is configured to engage the yoke 320 without the use of a ramp or a ratchet. The first spring 322 can be configured to compress, as shown in FIG. 8, when the closure trigger 304 is closed without the rack 316 causing movement of the yoke 320. The device 300 can include a spring cage similar to the spring cage 221 of the embodiment of FIG. 4. Rotation of the gear 314 can cause the rack 316 to move proximally, thereby causing the yoke 320 to move proximally and cause further closure of the end effector 306, as shown in FIG. 9. The gear 314 can be configured to disengage from the teeth of the rack 316 in response to motor failure and/or in response to ceased actuation of the firing actuator. For example, the device 300 can include a cam controlled by the controller and that pushes the gear 314 away from the teeth of the rack 316 in response to instruction by the controller. The motor safety spring 328 can have a bias and thus be configured to move the gear 314 down (or in some other direction, in some embodiments) in response to the gear's teeth being disengaged from the toothed rack 316. Disengagement of the gear 314 from the teeth of the rack 316 can allow the rack 316 to move distally by force of the bias spring 330 that biases the rack 316 to a distal position by biasing the spring cage distally. The jaws 308a, 308b can thus be opened.

Figure 10:
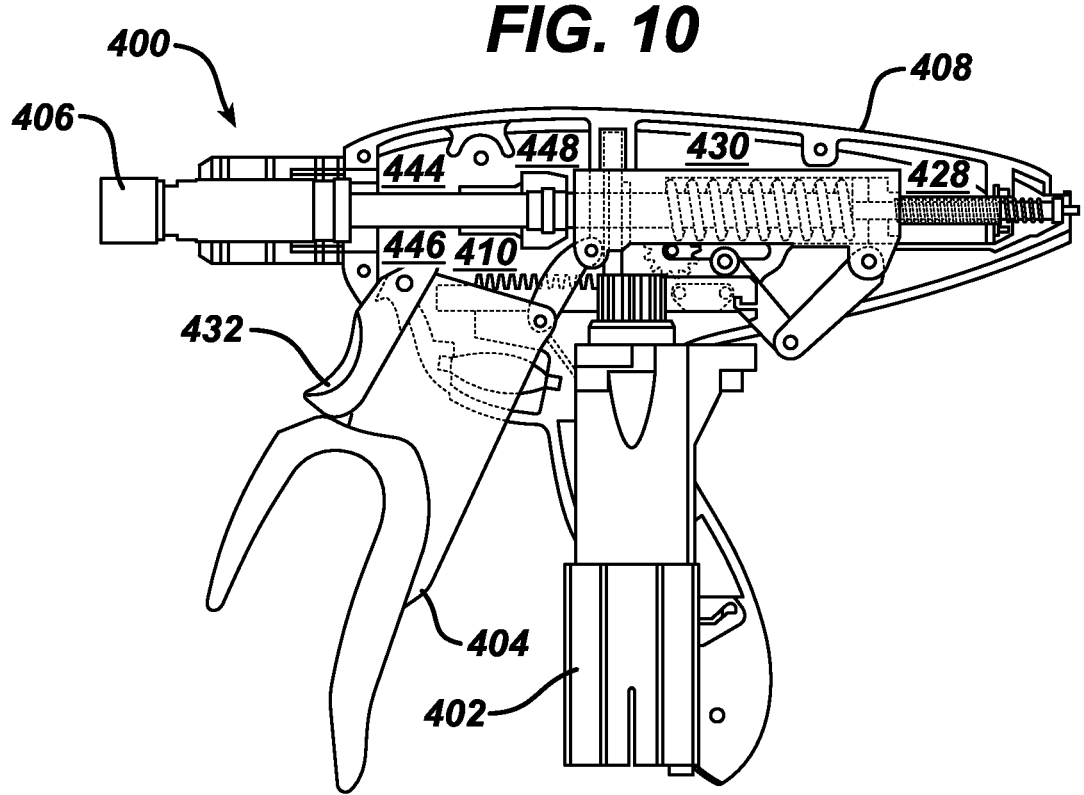
FIG. 10 is a side schematic view of another embodiment of a surgical device configured to begin providing power in response to an output from a sensor.
Figure 11:
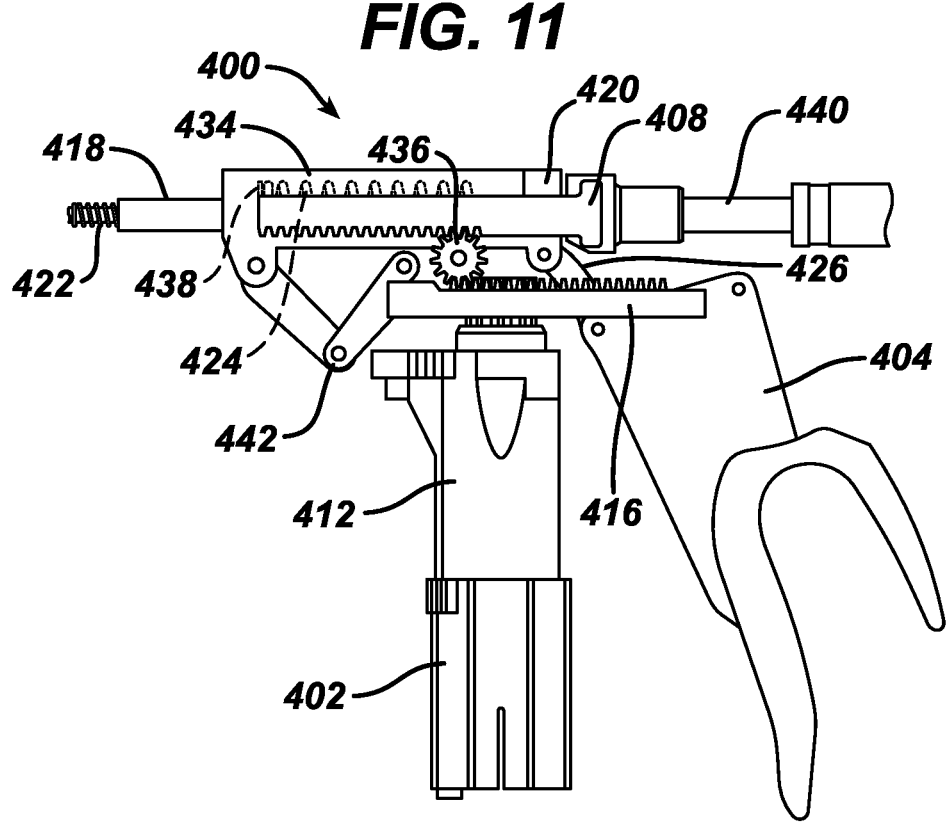
FIG. 11 is a schematic partial view of the surgical device of FIG. 10.
Figure 12:
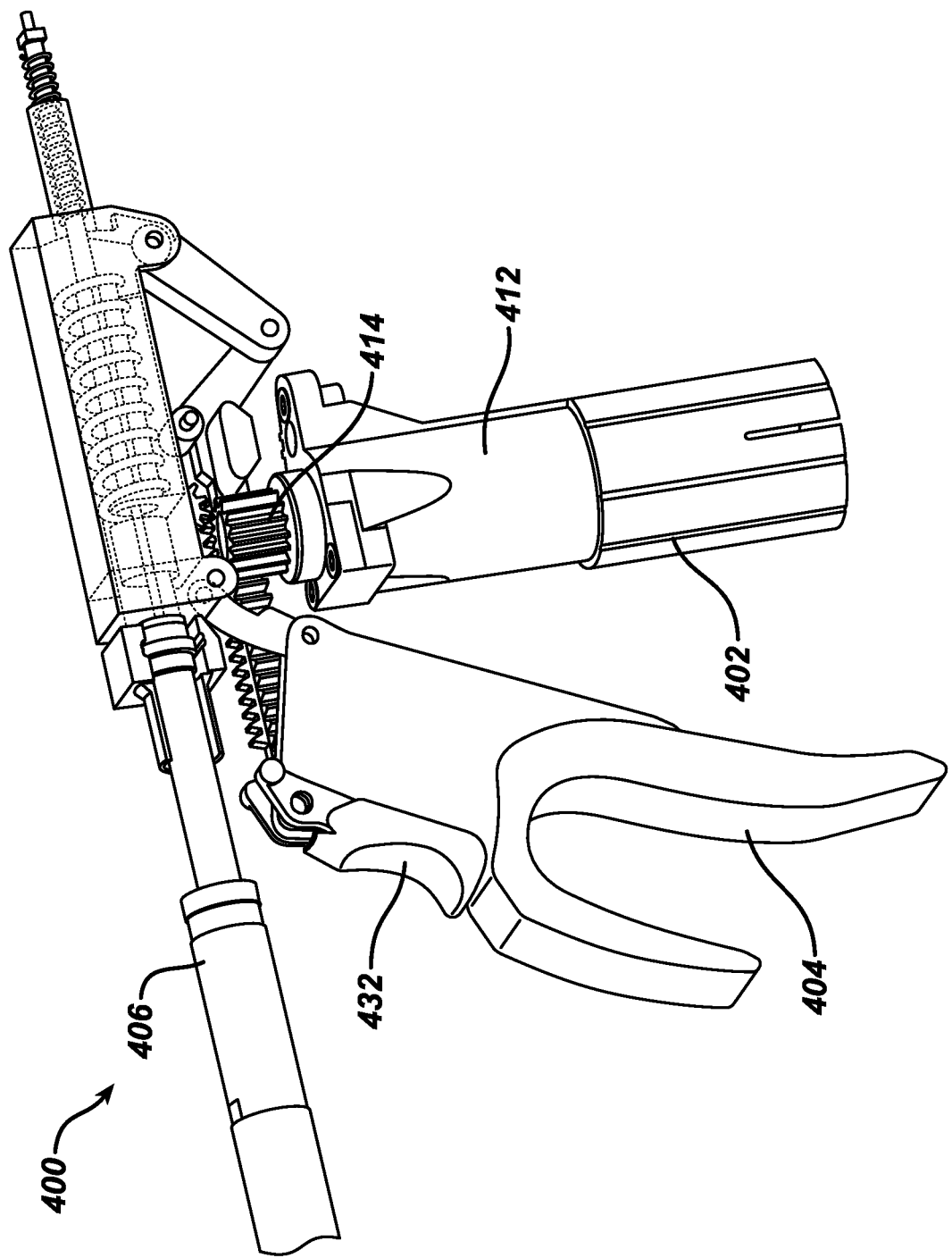
FIG. 12 is a perspective partial view of the surgical device of FIG. 10.

FIGS. 10-12 illustrate another embodiment of a surgical device 400 configured to begin providing power in response to an output from a sensor. The device 400 can generally be configured similar to the device 100 of FIG. 1. The device 400 can include a motor 402, a closure trigger 404, a firing actuator 432 in the form of a trigger, a controller (not shown), a power source (not shown), a cutting element in the form of a knife (not shown), an end effector (not shown) that includes a pair of jaws (not shown), an elongate shaft 406, a first sensor 410, a second sensor 428, a third sensor 444, a fourth sensor 446, a fifth sensor 448, a sixth sensor 430, a gear box 412, a gear 414, a reversing gear 436, a first toothed rack 416, a second toothed rack 408, a jaw closure tube 418, a first yoke 420, a second yoke 434, a first, proximal spring 422, a second, distal spring 424, a closure link 426, a closure toggle 442 that includes proximal and distal linkages, a handle housing 408, a stop ring 438, and a cutting element push tube 440. In general, the closure trigger 404 can be configured to be manually actuated by a user so as to cause the motor 402 to provide power that causes the end effector to move from an open position to a closed position, and the firing actuator 432 can be configured to be manually actuated by the user so as to cause the motor 402 to provide power that causes the cutting element to move relative to the pair of jaws. The device 400 can be configured to prevent the firing actuator 432 from being actuated until after the closure trigger 404 is actuated and the end effector has been closed. In this way, firing can be prevented until the jaws have tissue engaged therebetween, which can help prevent the cutting element from moving prematurely and damaging tissue and/or other material not intended to be cut.

Figure 13:
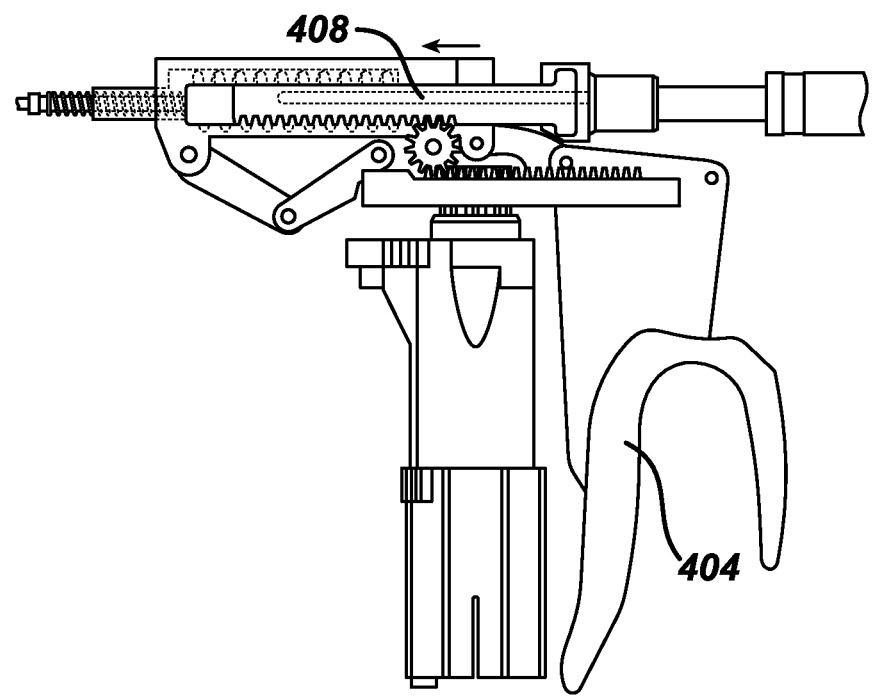
FIG. 13 is a side schematic view of the surgical device of FIG. 11 moved from a position of the surgical device in FIG. 11.
Figure 14:
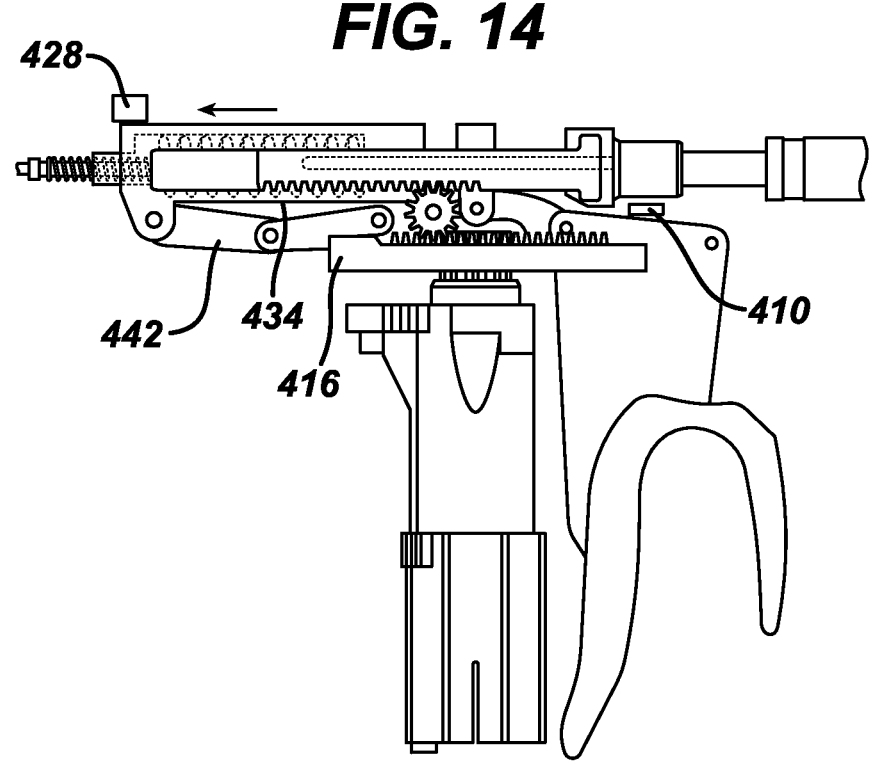
FIG. 14 is a side schematic view of the surgical device of FIG. 13 moved from a position of the surgical device in FIG. 13.
Figure 15:
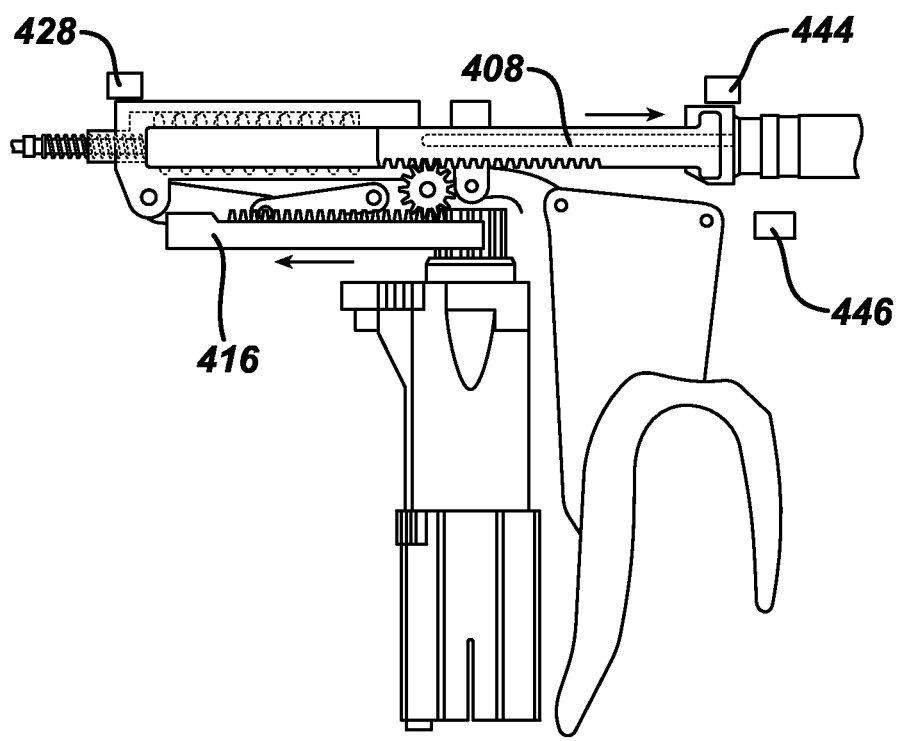
FIG. 15 is a side schematic view of the surgical device of FIG. 14 moved from a position of the surgical device in FIG. 14.

As discussed further below, FIGS. 10-12 show the device 400 in a first position in which the motor 402 is off and in which the end effector is in an open position with the jaws being open with a distance of space therebetween, FIG. 13 shows the device 400 in a second position moved from the first position in which the closure trigger 404 has been partially actuated, FIG. 14 shows the device 400 in a third position moved from the second position in which the motor 402 is triggered on and in which the end effector is in a closed position with the jaws closed, and FIG. 15 shows the device 400 in a fourth position moved from the third position in which the cutting element has been advanced distally through the jaws. A single motor can thus be used to close the end effector and to fire the cutting element.

The first position of the device 400 is similar to the first positions discussed above for the device 200 of FIG. 4 and the device 300 of FIG. 7. Also, the closure trigger 402 can be manually actuated similar to that discussed above. When the closure trigger 402 has begun to be actuated, e.g., manually pulled proximally by a user's hand, as shown in FIG. 13, the jaws 208a, 208b can be closed. More particularly, the closure trigger 404 being pulled toward the handle housing 408 can cause the closure trigger 402 to push the first yoke 420 proximally, thereby causing the first yoke 420 to push the second yoke 434 proximally. The proximal movement of the second yoke 434 can compress the second spring 424, which can pull the jaws closed. The force that the user need apply to the closure trigger 402 to compress the second spring 424 can be relatively low, which can help make the device 400 easy to use during a surgical procedure by users of different strengths and sizes. The motor 402 can be off when the device 400 is in the first position of FIGS. 10-12 and in the second position of FIG. 13.

When the closure trigger 404 becomes fully actuated from its partial actuation position shown in FIG. 13, so as to be in a final, clamped position, as shown in FIG. 14, the closure trigger 404 can activate the first sensor 410, e.g., by pushing down thereon as the closure trigger 404 is pulled toward the handle housing 408. As mentioned above, the device 400 can include a locking member that locks the closure trigger 404 in the final, clamped position. Activation of the first sensor 410 can cause the controller to cause the motor 402 to turn on. The controller can be configured to not activate the motor 402 in response to activation of the first sensor 410 if the fifth sensor 448 is not also activated. Activation of the fifth sensor 448 can indicate that the cutting element is in a proximal position relative to the end effector, e.g., that the knife is in a full back position. The second rack 408 can be configured to engage the fifth sensor 448 when the device 400 is in the first and second positions so as to activate the fifth sensor 448. The motor 402 can provide power that causes the gear 414 to rotate, similar to that discussed above, thereby causing the first toothed rack 416 having first teeth engaged with the gear 414 to move proximally. The first toothed rack's proximal movement can cause rotation of the reversing gear 436 engaged with second teeth of the first toothed rack 416. The rotation of the reversing gear 436 can cause the second rack 408 engaged with the reversing gear 436 to move distally, thereby causing the cutting element to move distally relative to the end effector, e.g., causing the cutting element push tube 440 to push the cutting element. The proximal movement of the first toothed rack 416 can also cause the first toothed rack 416 to contact and push the closure toggle 442, e.g., the distal linkage thereof, thereby causing the closure toggle 442 to move. The movement of the closure toggle 442 can cause the second yoke 434 to move proximally. The proximal movement of the second yoke 434 can cause the closure tube 418 to move proximally, thereby causing further closure of the jaws, such as by pivoting one of the jaws relative to the other of the jaws. In this way, the tissue clamped between the jaws can be held as securely in position as possible, thereby facilitating cutting of the tissue. The proximal movement of the second yoke 434 can also cause the second yoke 434 to activate the second sensor 428, e.g., push a switch. Activation of the second sensor 428 can cause the controller to stop the motor 402. The cutting element can be in position for firing through the jaws when the device 400 is in the third position of FIG. 14.

When the firing trigger 432 is actuated, e.g., manually pulled proximally by a user's hand, as shown in FIG. 15, the firing trigger 432 can activate the fourth sensor 446, e.g., push a switch. The activation of the fourth sensor 446 can cause the controller to activate the motor 402 to continue advancement of the cutting element. The motor 402 being on can rotate the gear 414, thereby causing the first rack 416 to move proximally, which can rotate the reversing gear 436 and cause distal advancement of the cutting element via distal movement of the cutting element push tube 440. The cutting element can be advanced distally until the second rack 408 activates the third sensor 444, e.g., pushes a switch. Activation of the third sensor 444 can cause the controller to stop the motor 402. If the fourth sensor 446 becomes deactivated during distal movement of the cutting element, thereby indicating that the firing trigger 432 has been released by the user, the controller can be configured to cause the motor 402 to reverse movement of the cutting element unless the fifth sensor 448 is activated so as to indicate that the cutting element is already in its full back position. In other words, the motor 402 can cause the gear 414 to rotate in an opposite direction so as to cause the cutting element to move proximally relative to the end effector. The motor 402 can thus be configured to automatically return or retract the cutting element when the firing trigger 432 stops being actuated, e.g., when the firing trigger 432 is released by the user. The fourth sensor 446 can optionally include two switches, one switch indicating an idle cutting element position and another switch indicating a distal cutting element position. When neither of the two switches are activated, the controller can be configured to cause the motor 402 to automatically return or retract the cutting element. When the switch indicating the distal cutting element position is not activated but the switch indicating the idle cutting element position is activated, the controller can be configured to not cause automatic retraction of the cutting element. In other words, the cutting element is in an idle position, and movement of the cutting element can be paused.

When the closure trigger 404 is released from its fully actuated position, e.g., by the user letting go of the closure trigger, by manual release of the locking member, etc., the first sensor 410 can be deactivated. The deactivation of the first sensor 410 can cause the controller to cause the motor 402 to go in reverse until the sixth sensor 430 is actuated. Activation of the sixth sensor 430 can cause the controller to turn off the motor 402. If the closure trigger 404 has not already been moved to its initial, start position, the closure trigger 404 can automatically move back to the initial, start position, such as by spring force.

Referring again to FIG. 1, the device 100 can be configured to adjust power provided by the motor 32 based on whether the device 100 is clamping tissue, e.g., the jaws 16a, 16b are being closed, or the device 100 is being fired, e.g., the firing actuator has been actuated to apply RF energy and/or to cut tissue grasped by the end effector 14. The device 400 of FIG. 10 illustrates one embodiment of such a device. The motor 402 of the device 400 of FIG. 10 can be configured to provide power at different levels based on which of the device's sensors are activated. For example, when the first sensor 410 is activated, the controller can be configured to cause the motor 402 to provide a first amount of power, e.g., rotate the gear 414 at a first speed, and when the fourth sensor 446 is activated, the controller can be configured to cause the motor 402 to provide a second amount of power, e.g., rotate the gear 414 at a second speed. The first and second amounts of power can be different such that the end effector can be clamped and the cutting element can cut at different speeds.

Figure 16:
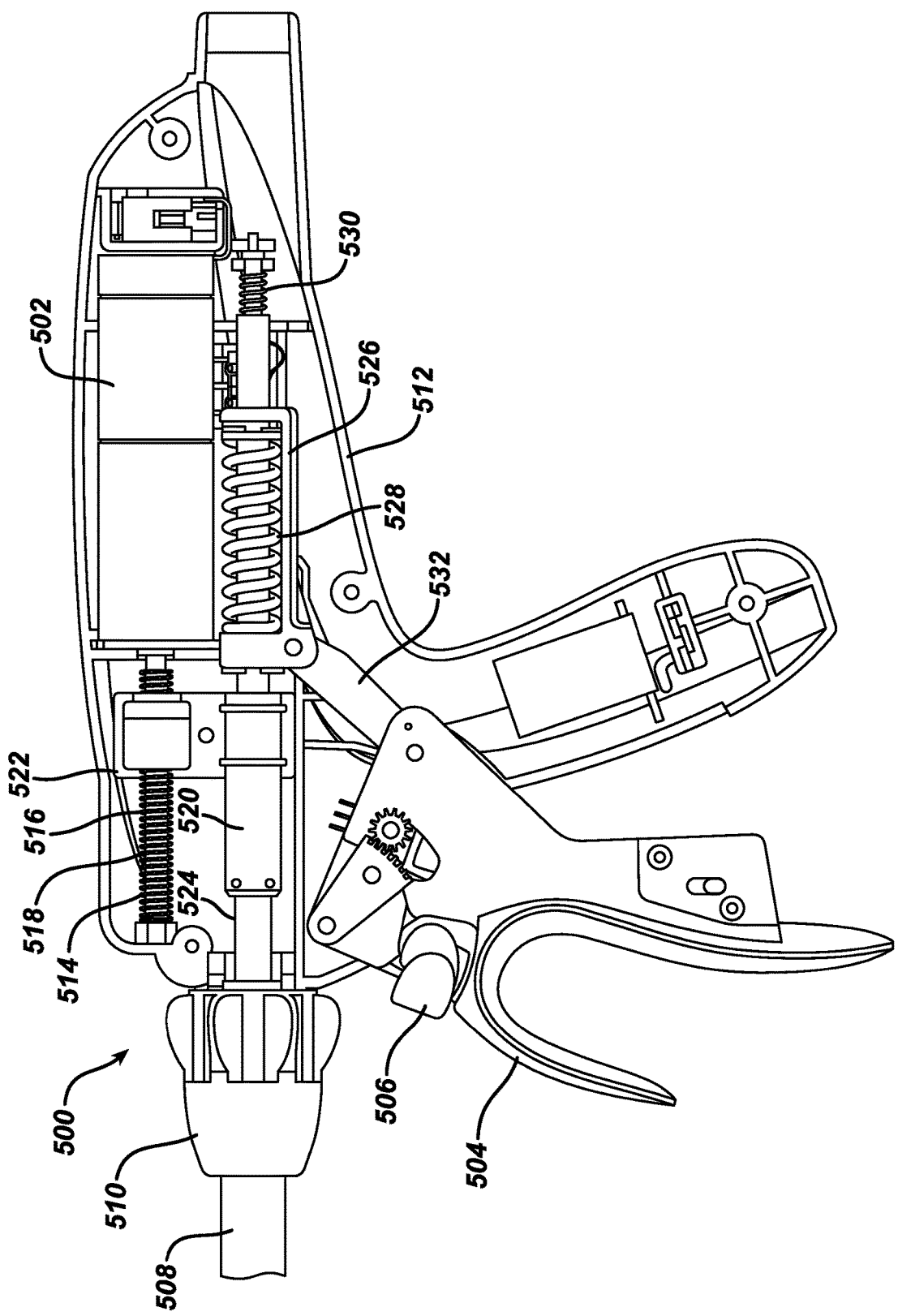
FIG. 16 is a side schematic view of an embodiment of a surgical device configured to adjust power based on whether clamping or firing is being performed.
Figure 17:
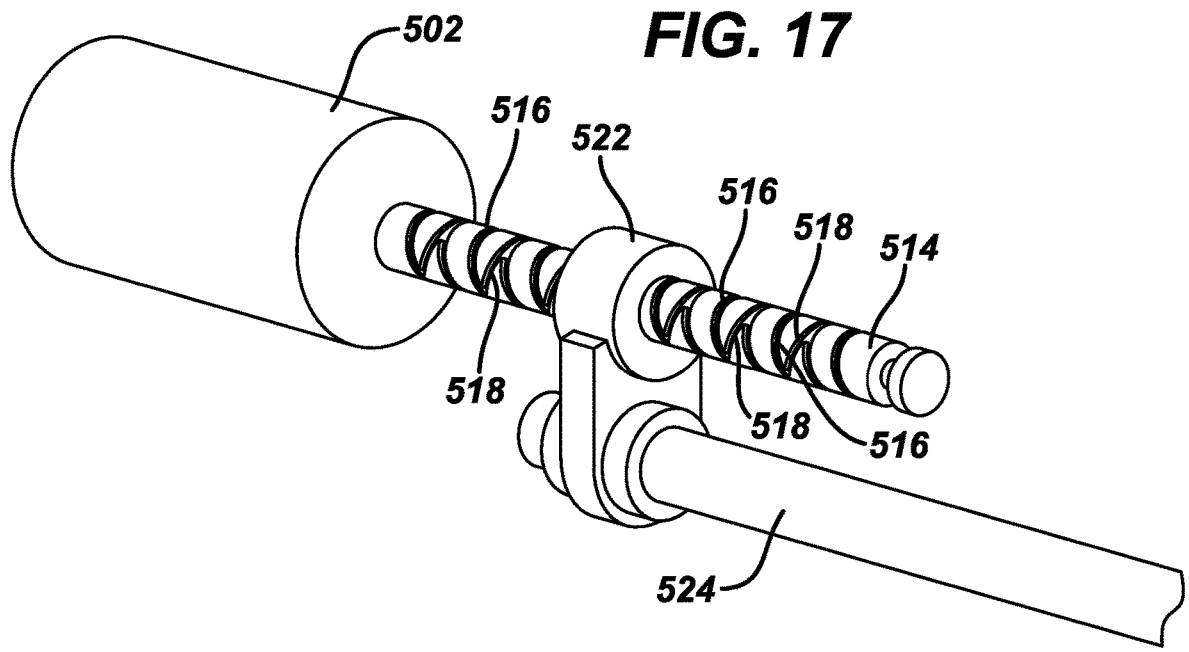
FIG. 17 is a perspective view of a motor, a gear shaft, a connector member, and a drive shaft of the surgical device of FIG. 16.

FIG. 16 illustrates another embodiment of a surgical device 500 configured to adjust power based on whether clamping or firing is being performed. The device 500 can generally be configured similar to the device 100 of FIG. 1. The device 500 can include a motor 502, a closure trigger 504, a firing actuator 506 in the form of a trigger, a controller (not shown), a power source (not shown), a cutting element (not shown), an end effector (not shown) that includes a pair of jaws (not shown), an elongate shaft 508, a knob 510 configured to rotate the shaft 508 about a longitudinal axis thereof, a handle housing 512, a gear shaft or worm gear 514 having a first thread 516 and a second thread 518, a connector shaft 520, a connector element 522 having opposed ends thereof coupled to the gear shaft 514 and the connector shaft 520, a drive shaft 524 coupled to the connector shaft 520, a yoke 526, a first, distal spring 528, a second, proximal spring 530, a closure link 532, and a key 534 (see FIG. 19) coupled to the connector element 522 and configured to threadably engage the first and second threads 516, 518. FIGS. 17-20 also variously show the gear shaft 514, the first and second threads 516, 518, the connector shaft 520, the connector member 522, the drive shaft 524, and the key 534. For clarity, the connector shaft 520 is omitted from FIGS. 17 and 18.

The first and second threads 516, 518 can be different from one another. The first and second threads 516, 518 can have different pitches. The first thread 516 can have a first pitch that is less than a second pitch of the second thread 518. In other words, the first thread 516 can have a tighter helix than the second thread 518. The first and second threads 516, 518 can have different handedness, e.g., the first thread 516 can be right handed and the second thread 518 can be left handed. In other words, the first and second threads 516, 518 can be opposed to one another. By having different handedness, the first and second threads 516, 518 can cross one another at multiple locations along a longitudinal length of the gear shaft 514, as shown in FIGS. 17-20.

The motor 502 can be configured to drive the drive shaft 524 at two different speeds based on whether the key 534 is threading through the first thread 516 or the second thread 518. The first thread 516 having the smaller pitch can correspond to a slower speed providing a higher force, and the second thread 518 having the larger pitch can correspond to a faster speed providing a lower force. A higher one of the speeds, and hence one of the threads 516, 518, can correspond to distal movement of the drive shaft 524, and a lower one of the speeds, and hence the other one of the threads 516, 518, can correspond to proximal movement of the drive shaft 524. In this way, the speed of the cutting element can be controlled, which can facilitate cutting of thick, tough, irradiated, and/or calcified tissue by allowing the cutting element to cut with a relatively high force, can facilitate cutting of tender and/or thin tissue by allowing the cutting element to move and cut quickly, and/or can allow the cutting element to be retracted relatively quickly. Relatively fast retraction of the cutting element can allow the cutting element to be reset relatively quickly, which can save time during performance of a surgical procedure.

Using the gear shaft 514 to control power provided by the motor 502 to the drive shaft 524 can allow the motor 502 to have less weight, cost, and/or power consumption than motors configured to provide varying amounts of power. In other words, the motor 502 can be configured to provide an amount of power that the gear shaft 514 can be configured to transfer to the drive shaft 524 in different amounts based on whether the key 534 is riding in the first thread 516 or in the second thread 518.

Figure 18:
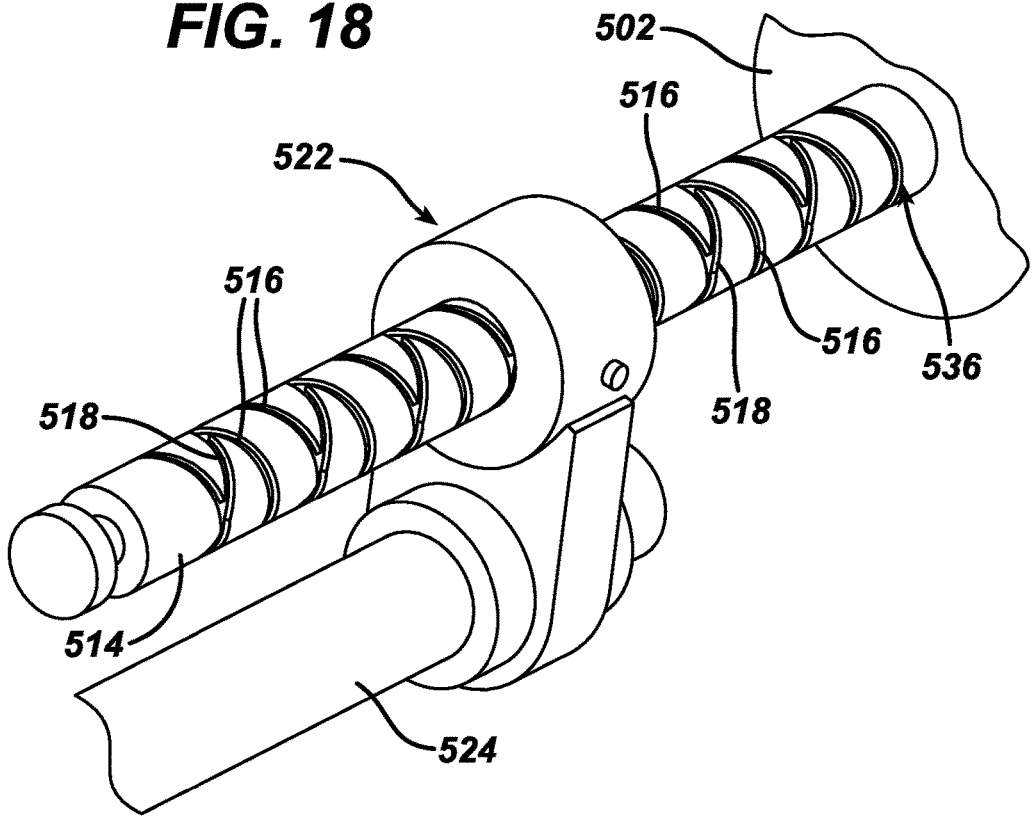
FIG. 18 is another perspective view of the motor, the gear shaft, the connector member, and the drive shaft, of the surgical device of FIG. 17.
Figure 19:
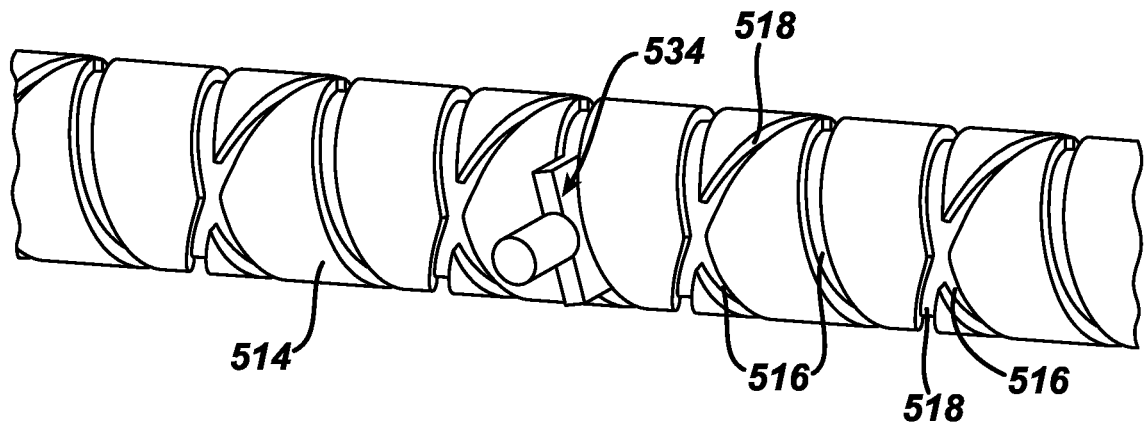
FIG. 19 is a perspective view of the motor shaft and a key of the surgical device of FIG. 17.
Figure 20:
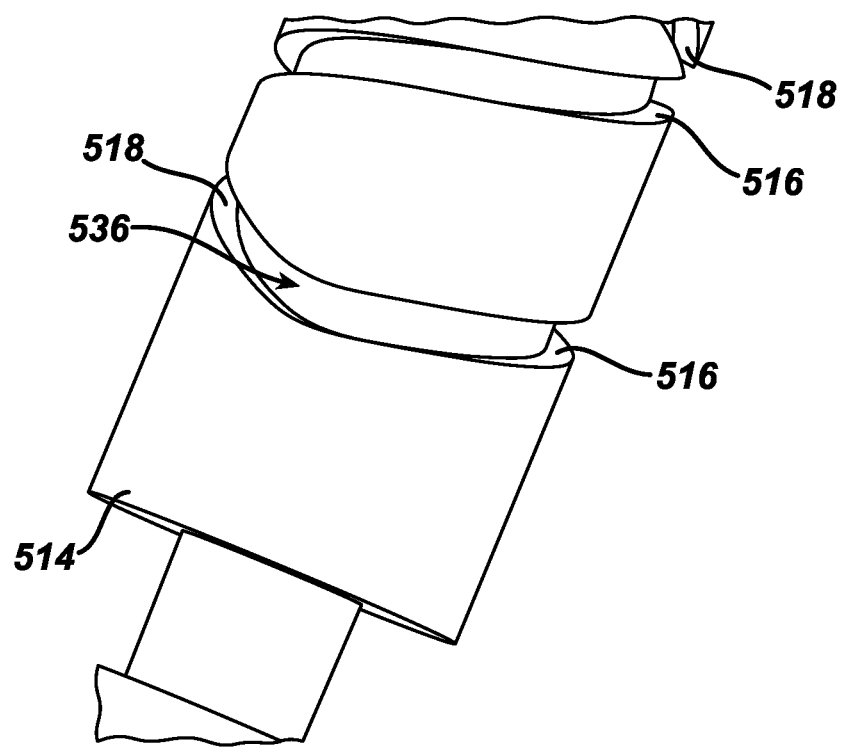
FIG. 20 is a perspective view of the motor shaft of FIG. 17.

The first and second threads 516, 518 can merge at a merge region 536 at each opposed end of the gear shaft 514, as shown in FIGS. 18 and 20, which each have one of the opposed ends identified by reference numeral. The merge regions 536 can allow the key 534 to move between the first and second threads 516, 518. When the key 534 is riding in the first thread 516 and enters one of the merge regions 536, the key 534 can move into the second thread 518, and vice versa. Passing through one of the merge regions 536 can thus reverse the direction of movement of the key 534, and hence reverse the direction of movement of the connector element 522 and the drive shaft 524.

The key 534 can be configured to facilitate reversal thereof in the merge regions 536. For example, the key 534 can be rotationally biased such that when the key 534 is in one of the threads 516, 518 and moves into one of the merge regions 536, reversal of the drive direction in combination with the rotational bias can cause the key 534 to move into the other one of the threads 516, 518. The rotational bias can be provided in a variety of ways, such as via a torsional spring or a solenoid. The solenoid can allow for bias in either direction so that the key 534 can be moved into either one of the threads 516, 518 as needed. For another example, the key 534 can be configured to move up out of the one of the threads 516, 518 in which it is seated, rotate, and then move back down into the other one of the threads 516, 518.

The motor 502 can be configured to run in a same direction to cause the key 534, and hence the connector element 522 and the drive shaft 524, to move distally and to cause the key 534, and hence the connector element 522 and the drive shaft 524, to move proximally. The merge regions 536 can allow the motor 502 to run in the same direction while the key 534, and hence the connector element 522 and the drive shaft 524, switch directions. For example, the motor 502 can be running in the first direction so as to cause the key 534, the connector element 522, and the drive shaft 524 to move distally, and when the key 534 passes through a distal one of the merge regions 536, the key 534, the connector element 522, and the drive shaft 524 can begin to move proximally.

The motor 502 can be reversed from one direction into another, opposite direction so that, for example, the key 534 can move from the first thread 516, e.g., the slower speed thread, to the second thread 518, e.g., the faster speed thread, so as to allow for quicker cutting. Quicker cutting can be beneficial when cutting thin and/or tender tissue. The motor 502 can be reversed in any number of ways, as will be appreciated by a person skilled in the art.

Figure 21:
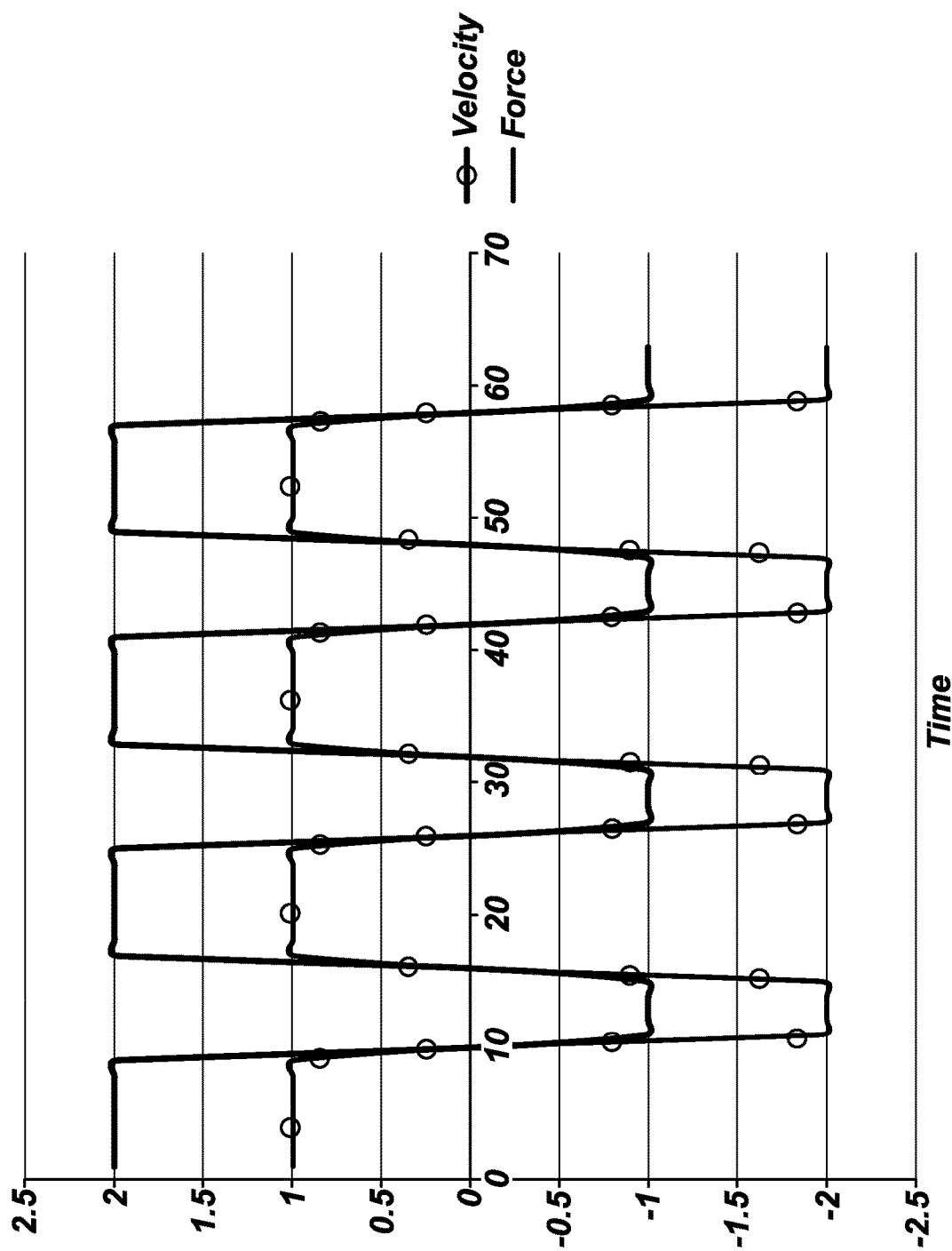
FIG. 21 is a graph showing relative multiplier for speed and force versus time for the surgical device of FIG. 16.

FIG. 21 shows a graph of a relative multiplier for speed (one graph line) and force (another graph line) versus time as the motor 502 is on so as to rotate the gear shaft 514 such that the key 534 rides through the first and second threads 516, 518.

Referring again to FIG. 1, the device 100 can be configured to adjust an amount of power provided by the motor 32 based on an amount of pressure that the user applies to an actuator, e.g., to the clamping trigger 20 or to the firing actuator 24. The device 100 can be configured to detect when the user is applying a force to the actuator above a predetermined threshold of force, thereby indicating that the tissue grasped by the end effector 14 is thick, tough, irradiated, and/or calcified, that the user is having to strain to close the jaws 16a, 16b, and/or that the user is having to strain to cut the tissue held between the jaws 16a, 16b. When the detected force is equal to or greater than the predetermined force, the motor 32 can be configured to provide power as a supplement the user's applied force or to provide power in place of the user's applied force. The predetermined threshold of force can be based on a human factor, e.g., how hard a human can actuate a trigger before it becomes too onerous. For example, the predetermined threshold of force can be in a range of about 2 to 4 pounds of hand grip force.

Figure 22:
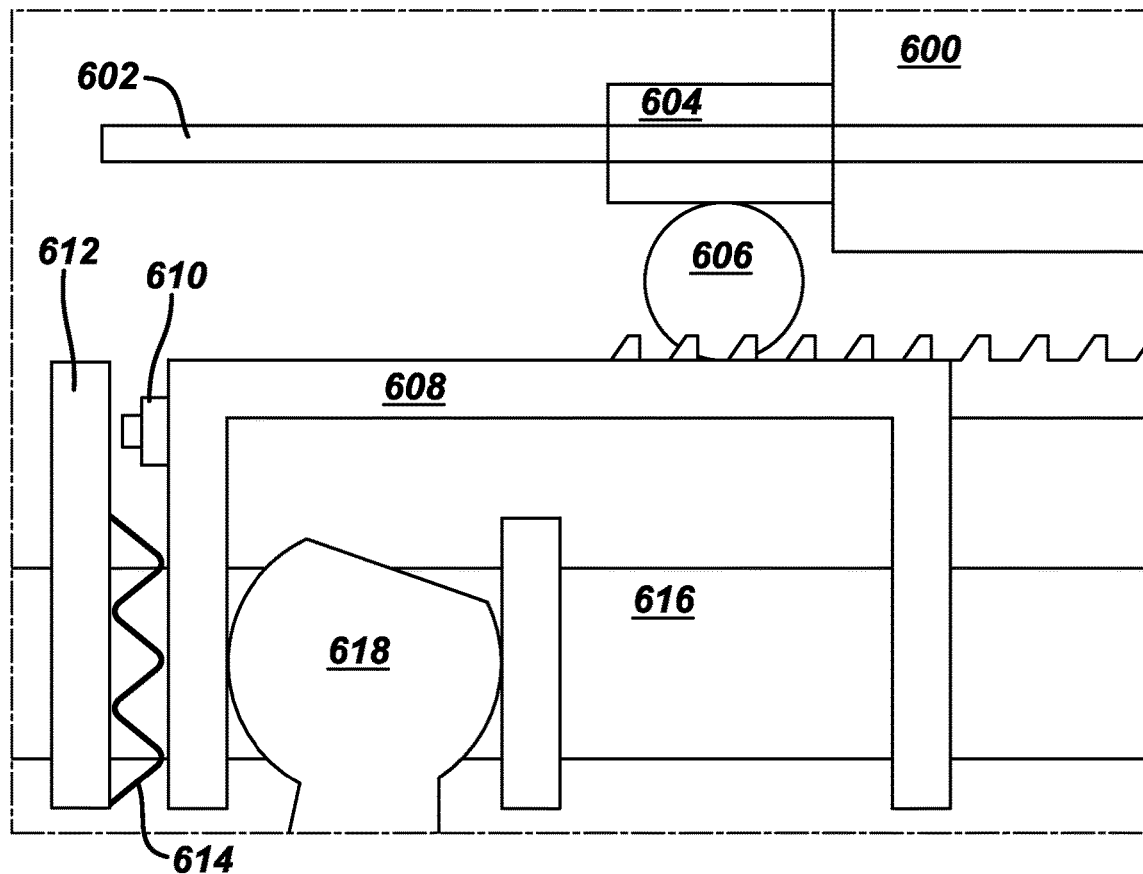
FIG. 22 is a side schematic view of an embodiment of a surgical device configured to adjust an amount of power provided by a motor based on an amount of pressure that a user applies to an actuator.
Figure 23:
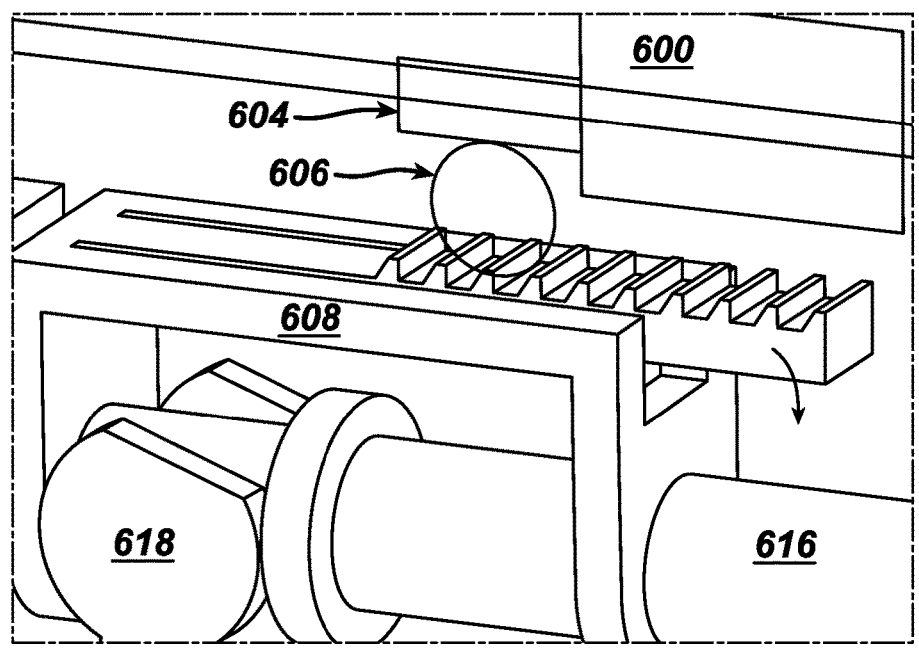
FIG. 23 is a perspective view of the surgical device of FIG. 22.

FIGS. 22 and 23 illustrate one embodiment of a surgical device configured to adjust an amount of power provided by a motor based on an amount of pressure that a user applies to an actuator. The device can generally be configured similar to the device 100 of FIG. 1. The device can include a closure trigger (not shown), a firing actuator (not shown), a controller (not shown), a power source (not shown), an end effector (not shown) that includes a pair of jaws (not shown), an elongate shaft (not shown), a motor 600, a shaft 602, a gear shaft or worm gear 604 attached to the shaft 602, a pinion gear 606 coupled to the worm gear 604, a sled 608 that includes an integrated toothed rack engageable with the pinion gear 606, an sensor 610 attached to the sled 608, a collar 612 configured to activate the sensor 610, a spring 614 positioned between surfaces of the collar 612 and the sled 608, a cutting element (not shown), a cutting element push tube operatively connected to the cutting element 616, and a cam 618 positioned between surfaces of the sled 608 and the collar 612. The sensor 610 in this illustrated embodiment include a push button switch, but the sensor could have other forms. The spring 614 in this illustrated embodiment includes a wave spring, but the spring 614 could have other forms, e.g., a leaf spring, an expansion spring, etc. The gear shaft 604 is concentric with the motor 600 in the embodiment of FIG. 22.

The device can be configured to allow a user to manually advance the cutting element by actuating the firing actuator, e.g., by pulling a trigger, without the motor 600 providing power for the firing. If the user applies a force less than a predetermined force, then the motor 600 can stay off. If the user applies a force equal to or greater than the predetermined force, then the motor 600 can be configured to be provide supplemental force for firing. The motor 600 can be configured to switch between providing power and not providing power based on the user's input force. The motor 600 can be configured to turn on/off without any user input other than the user's input to the firing actuator. The device can thus be configured to provide additional force for cutting if the user is applying a certain amount of minimum force, thereby indicating that the user is having difficulty applying adequate force to the actuator and/or that the tissue being cut is thick, tough, irradiated, and/or calcified.

As discussed further below, the spring 614 can define the predetermined force. More particularly, as will be appreciated by a person skilled in the art, the spring 614 has a spring constant. The spring constant can define the predetermined force.

FIGS. 22 and 23 show the device in a first position in which the motor 600 is off. When the firing actuator is actuated by a user applying a force thereto, the cutting element can be configured to advance distally, similar to that discussed above, without motor assistance. When the motor 600 is off, the teeth of the rack can click past the pinion gear 606, as shown in FIG. 23. When the force applied by the user is equal to or greater than the predetermined force, then the spring 614 can be compressed via movement of the cam 618. The cam 618 moving and the spring 614 compressing can move the sled 608 toward the collar 612, which can accordingly move the sensor 610 toward the collar 612 such that the sensor 610 can be pushed against the collar 612 so as to activate the sensor 610. The sensor 610 can be in electronic communication with the motor 600 directly and/or through the controller. Thus, the sensor 610 being activated can trigger the motor 600 to turn on so as to provide supplemental force to the cutting element. As long as the sensor 610 is pushed against the collar 612, the motor 600 can be on. When the motor 600 is on, the motor 600 can be configured to provide a constant force, e.g., supply a constant amount of power, or the motor 600 can be configured to provide a variable amount of power. For example, the motor 600 can be configured to apply a greater amount of power the greater amount of force applied by the user to the firing actuator. When the motor 600 is on, the teeth of the rack can engage with the pinion gear 606 to provide the supplemental force. When the user ceases to apply a force equal to or above the predetermined force, the sensor 610 can move out of engagement with the collar 612, thereby deactivating the sensor 610. The motor 600 can thus turn off and stop providing the supplemental power. The motor 600 can be repeatedly turned on and off any number of times based on the user's input force. The motor 600 can thus dynamically adjust its power output based on the user's applied force to the firing actuator.

Figure 24:
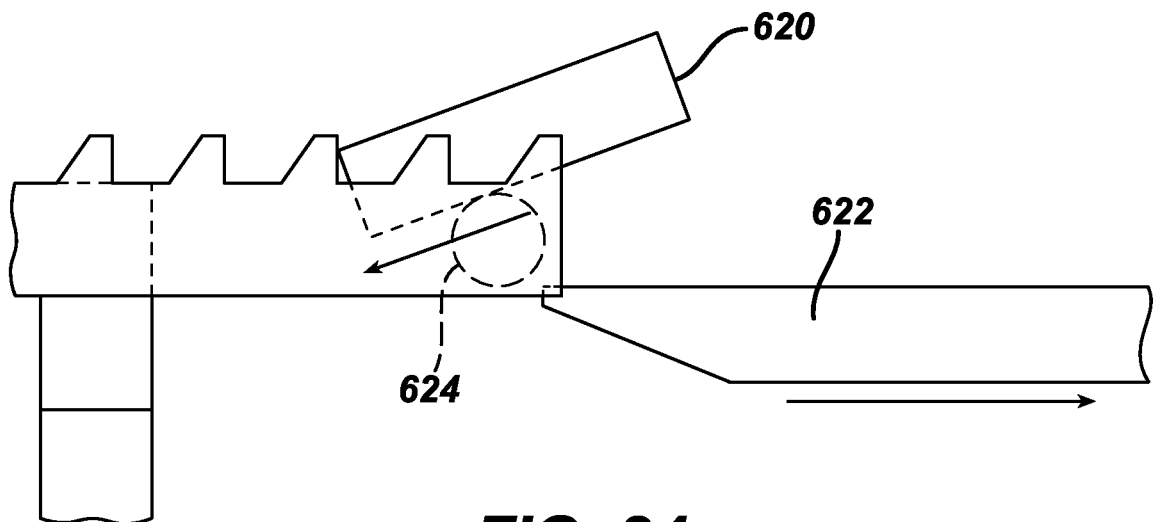
FIG. 24 is a side schematic view showing a return stroke of the surgical device of FIG. 22.
Figure 25:
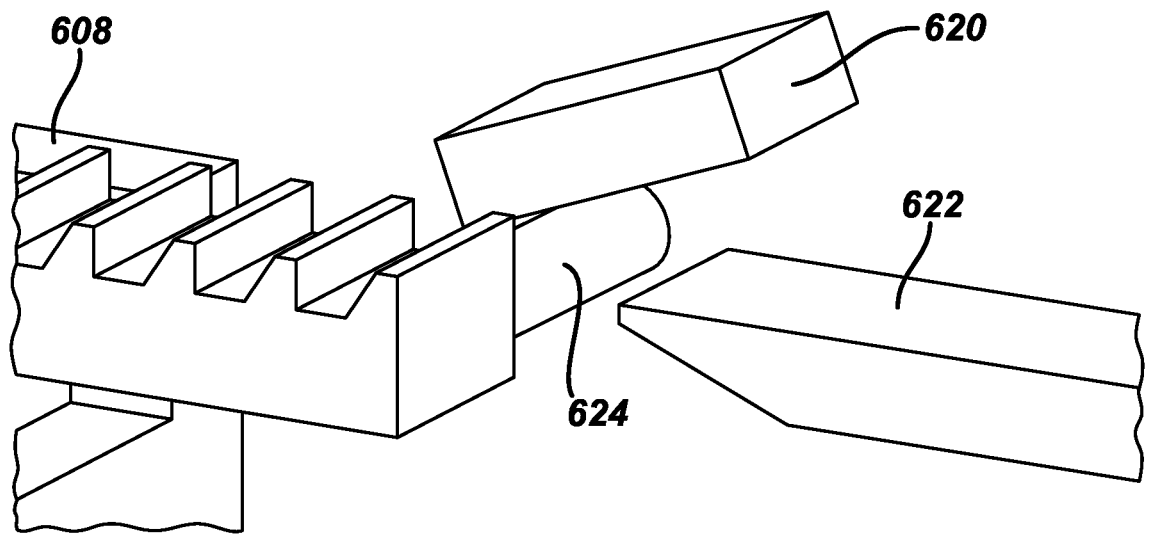
FIG. 25 is a perspective view showing a return stroke of the surgical device of FIG. 22.

FIGS. 24 and 25 illustrate the return stroke in which the cutting element is retracted proximally. The device can include first and second ribs 620, 622 and a ratchet pin 624 coupled to the rack configured to facilitate return stroke and disengagement of the rack. The first rib 620 can be configured to engage the ratchet pin 624 so as to force the rack down and disengage the rack's teeth from the pinion gear 606. The second rib 622 can be configured to keep the rack disengaged from the pinion gear 606 during the return stroke. The second rib 622 can be flexible such that as the pin 624 moves down the first rib 620, the pin 624 can deflect the second rib 622. In other words, the pin 624 can cause the second rib 622 to bend or flex. In this way, once the pin 624 passes off the second rib 622, the pin 624 can spring back up and be in position to keep the rack down on the return stroke. The second rib 622 can have a length that is short enough such that at the end of the return stroke, the pin 624 can fall off of the second rib 622 and come back to the top of the rib 622.

Figure 26:
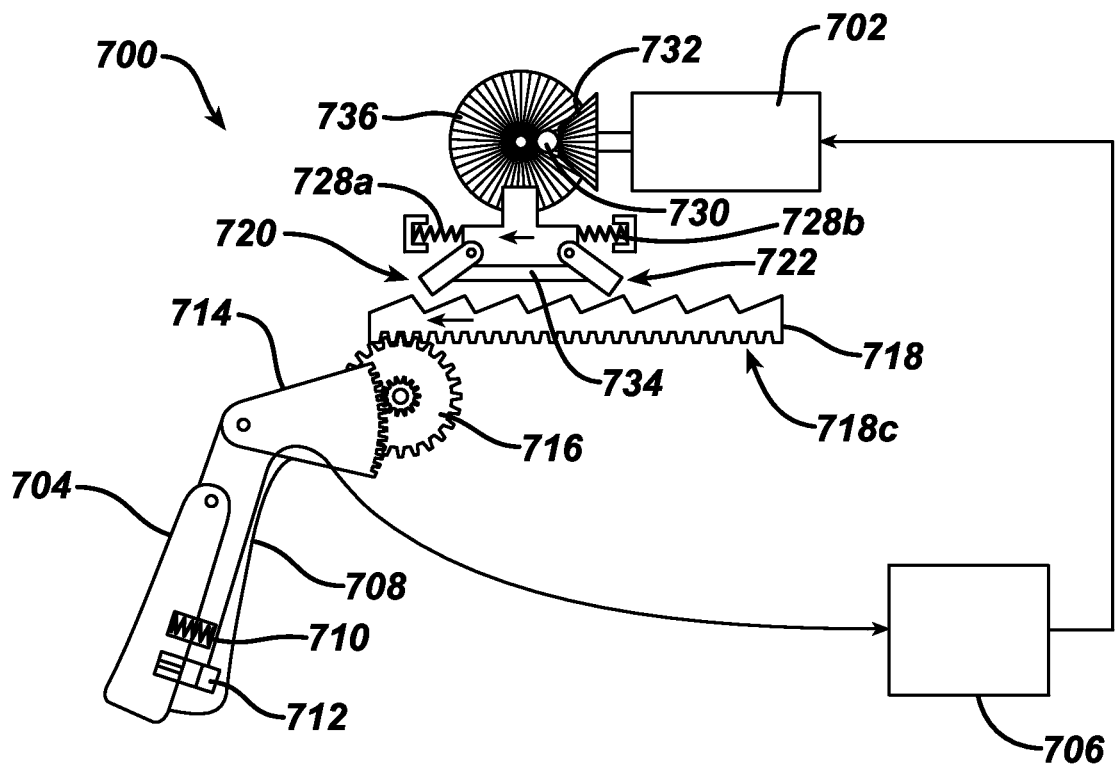
FIG. 26 is a side schematic view of another embodiment of a surgical device configured to adjust an amount of power provided by a motor based on an amount of pressure that a user applies to an actuator.
Figure 27:
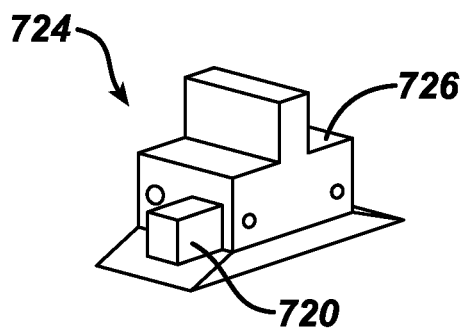
FIG. 27 is a perspective view of a ratchet assembly of the surgical device of FIG. 26.
Figure 28:
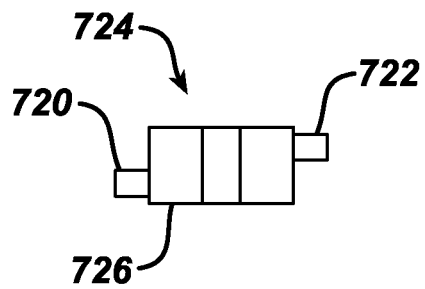
FIG. 28 is a top view of the ratchet assembly of FIG. 27.
Figure 29:
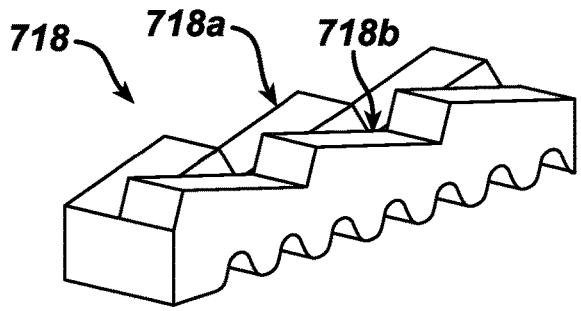
FIG. 29 is a perspective view of a rack of the surgical device of FIG. 26.
Figure 30:
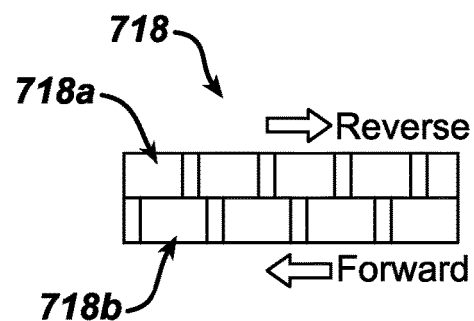
FIG. 30 is a top view of the rack of FIG. 29.
Figure 31:
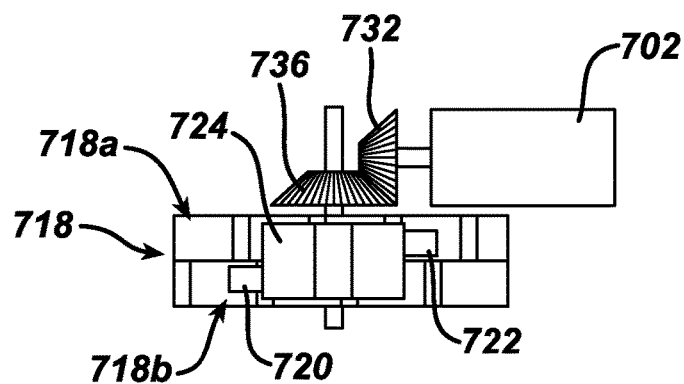
FIG. 31 is a top view of engagements of the ratchet assembly of FIG. 27, the rack of FIG. 29, and a motor of the surgical device of FIG. 26.

FIG. 26 illustrates another embodiment of a surgical device 700 configured to adjust an amount of power provided by a motor 702 based on an amount of pressure that a user applies to an actuator, which in this illustrated embodiment includes a firing trigger 704. The device 700 can generally be configured similar to the device 100 of FIG. 1. The device 700 can include the motor 702, the trigger 704, a controller 706 in the form of a CPU, a power source (not shown), an end effector (not shown) that includes a pair of jaws (not shown), a cutting element (not shown), a compression member (not shown), an elongate shaft (not shown), a stationary handle 708, a trigger spring 710, a sensor 712 in the form of a two position switch, a sector gear 714, a compound gear 716, a rack 718 that includes first, second, and third sets of teeth 718a, 718b, 718c (also see FIGS. 29 and 30), a ratchet assembly 724 (also see FIGS. 27 and 28) that includes a first, forward pawl 720, a second, reverse pawl 722, and a ratchet body 726, first and second springs 728a, 728b, a cam arm or pin 730, a motor gear 732, a ledge 734 engageable with the ratchet assembly 724, and a ratchet gear 736 (also see FIG. 31) engaged with the motor gear 732 and having the pin 730 extending therefrom. The device 700 can optionally include RF functionality.

In general, the device 700 can provide for motor control by the ratchet mechanism 724 interacting with the rack 718 based on a direction that the motor 702 is turning. The first and second pawls 720, 722 can be staggered on the ratchet assembly 724 to correspond to the rack's staggered first and second teeth 718a, 718b. The first teeth 718a can be configured to engage with the first pawl 720 to move the rack 718 forward, e.g., distally, and the second teeth 718b can be configured to engage with the second pawl 722 to move the rack 718 in reverse, e.g., proximally. The pawls 720, 722 can rest on the ledge 734 and can be held in place by the first and second springs 728a, 728b, respectively. The ledge 734 can be configured to prevent the pawls 720, 722 from contacting the rack 718 when the motor 702 is idle, e.g., is off. The rack 718 can thus move freely in response to actuation of the actuator, e.g., when the user manually pulls the trigger 704.

Figure 32:
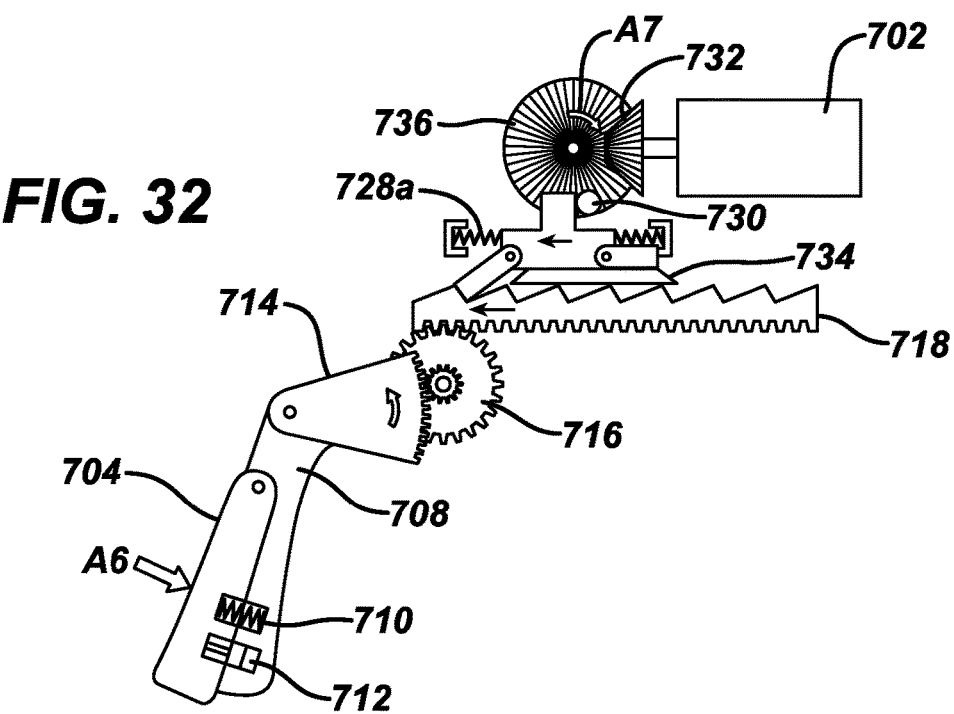
FIG. 32 is a side schematic view of the surgical device of FIG. 26 moved from a position of the surgical device in FIG. 26.
Figure 33:
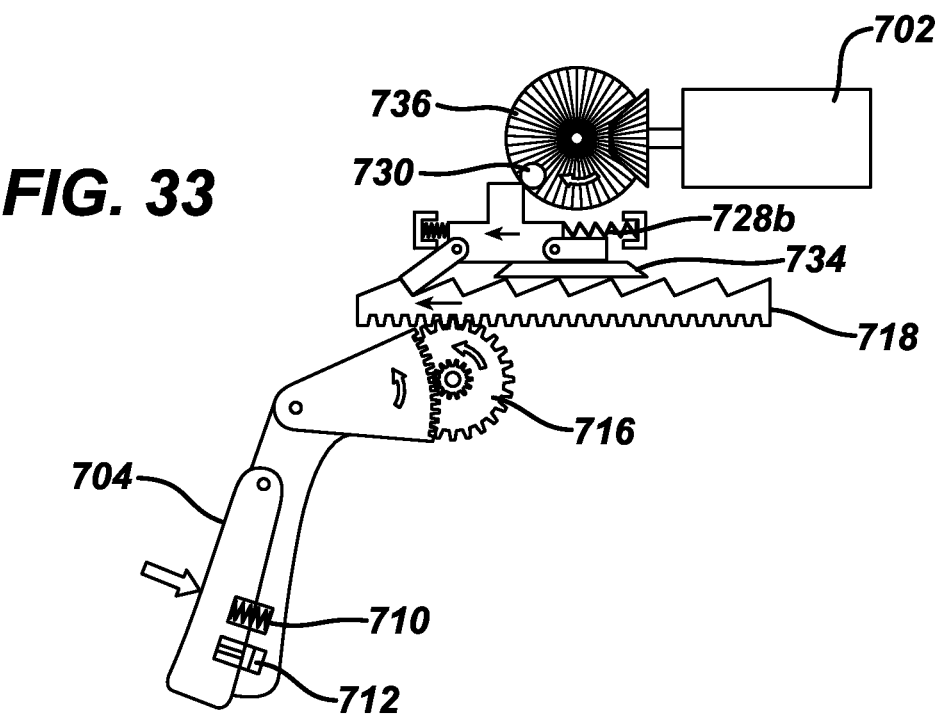
FIG. 33 is a side schematic view of the surgical device of FIG. 32 moved from a position of the surgical device in FIG. 32.
Figure 34:
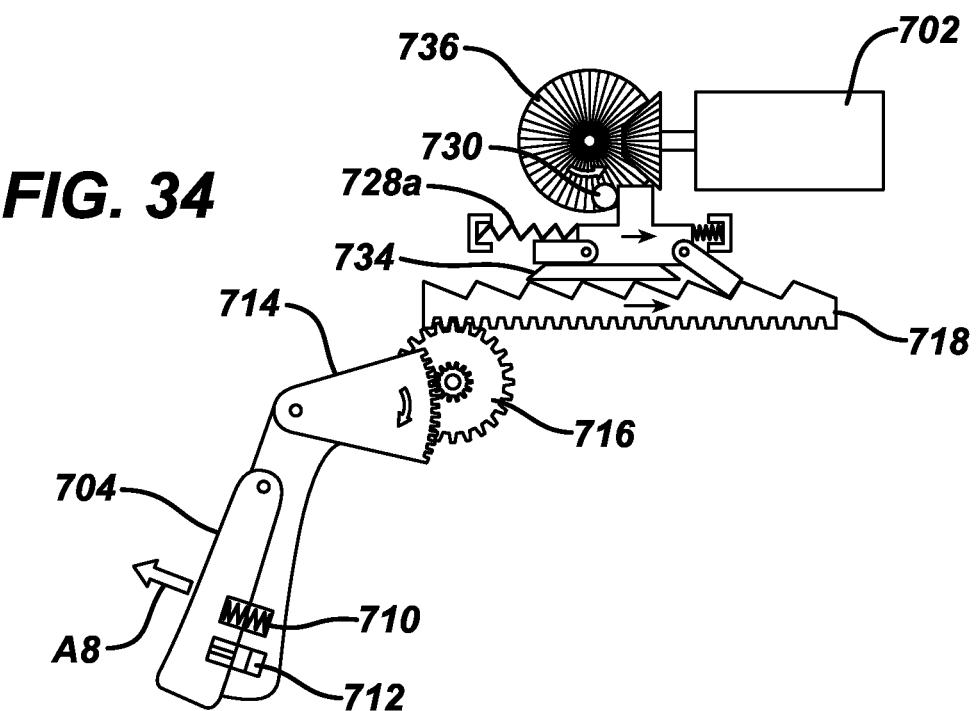
FIG. 34 is a side schematic view of the surgical device of FIG. 33 moved from a position of the surgical device in FIG. 33.

As discussed further below, FIG. 26 shows the device 700 in a first position in which the motor 702 is off and in which the firing trigger 704 is actuated so as to activate a first position of the switch 712, FIG. 32 shows the device 700 in a second position moved from the first position in which firing trigger 704 is further actuated so as to activate a second position of the switch 712 and cause the motor 702 to turn on, FIG. 33 shows the device 700 in a third position moved from the second position in which firing has reached a full stroke, and FIG. 34 shows the device 700 in a fourth position moved from the third position in which the firing trigger 704 is retracted.

The firing trigger 704 can be actuated by being having a force applied thereto, e.g., by a user's hand, toward the stationary handle 708. This movement of the trigger 704 can cause the sector gear 714 to move, which can cause the rack 718 to move when the motor 702 is not active. More particularly, the sector gear 714 can rotate, which can cause rotation of the compound gear 716. The compound gear 716 can have teeth engaged with the third teeth 718c of the rack 718 such that the compound gear's rotation can cause the rack 718 to move distally. The rack's distal movement can cause the cutting element to be distally advanced. The cutting element can be attached to the compression member, e.g., a knife blade mounted thereon, a sharpened edge of the compression member, etc., such that the rack's distal movement can also cause distal advancement of the compression member. The ledge 734 can keep the pawls 720, 722 out of engagement with the first and second teeth 718a, 718b of the rack 718 during manual firing. The ledge 734 can be positioned such that when the ratchet assembly 724 is in a neutral, default position, the pawls 720, 722 can sit on the ledge 724 and not be engaged with any teeth of the rack 718. As the ratchet assembly 724 moves in one direction or the other, e.g., proximally or distally, one of the pawls 720, 722 can move off the ledge 724 and can engage one set of the rack's teeth 718a, 718b. The firing trigger 704 can push against the sensor 712 when the firing trigger 708 is near enough to the stationary handle 708 to activate the first position of the sensor 712, as shown in FIG. 26. The sensor 712 is attached to the stationary handle 708 in this illustrated embodiment, but the sensor 712 could instead be attached to the firing trigger 704. The activation of the sensor's first position can cause the motor 702 to be activated.

The activation of the sensor's first position can cause no compression or a small amount of compression of the trigger spring 710. If the force applied to the firing trigger 704 is not enough to compress the trigger spring 710, then the motor 702 can remain off, and the device 700 can be fired using only manual user input to the firing trigger 704. If the force applied to the firing trigger 704 is enough to compress the trigger spring 710, then the firing trigger 704 can further push against the sensor 712 in a direction of arrow A6, as shown in FIG. 32, to activate the second position of the sensor 712. The activation of the second position of the sensor 712 can cause the motor 702 to turn on and cause rotation of the motor gear 732. The rotation of the motor gear 732 can cause rotation of the ratchet gear 736 in a clockwise direction, as shown by arrow A7. The rotation of the ratchet gear 736 can cause the pin 730 attached to the ratchet gear 736 to push against the ratchet assembly 724, thereby causing the ratchet assembly 724 to move distally relative to the ledge 734. The first pawl 720 can thus move enough off the ledge 734 to engage the first teeth 718a of the rack 718. The first pawl 720 can contact the rack 718 with an impact force that gives the motor 702 a mechanical advantage to help drive the rack 718 forward when there is resistance in the system to the motion. As the motor 702 continues to drive the motor gear 732, the ratchet assembly 724 and hence the first pawl 720 attached thereto can continue moving distally. The rack 718 can thus be driven distally by manual user input with motor assistance.

If at any time before the rack 718 advances to its full firing distal position the user-applied force reduces so as to no longer engage the switch's second position, the motor 702 can stop, and the rack 724 can freely move according to the user's input force. The second spring 728b that has expanded in response to the rack's distal movement, as shown in FIG. 32, can return to its default, biased position, thereby returning the ratchet assembly 724 to its default, biased position on the ledge 734 without the pawls 720, 722 engaging the first teeth 718a or the second teeth 718b of the rack 724, thereby facilitating the free movement of the rack 718.

When the rack 718 is advanced to its full firing distal position, as shown in FIG. 33, whether under manual force only or under a combination of manual force and motor force, a full stroke sensor (not shown), e.g., a push button switch, can be activated. The full stroke sensor can be located, for example, at a distal end of the rack 718 and be activated when the distal end of the rack 718 abuts a surface of the device 700. Activation of the full stroke sensor can cause the motor 702 to reverse direction. If the motor 702 was not previously on to advance the rack 718, the motor 702 can turn on and drive the gear 732 in the reverse direction. The motor gear's reverse direction can cause the ratchet gear 736 to reverse its rotation direction. The pin 730 will consequently cease pushing against the ratchet assembly 724, thereby allowing the force of the second spring 728b to move the ratchet assembly 724 toward its default position.

When the ratchet gear 736 has rotated enough in the reverse direction, the pin 730 can push against an opposite side of the ratchet assembly 724, as shown in FIG. 34, than where the pin 730 pushes against the ratchet assembly 724 to move the rack 718 distally. This pushing can cause the ratchet assembly 724 to move proximally off the ledge 734, thereby allowing the second pawl 722 to engage the second teeth 718b of the rack 718 and cause the rack 718 to move proximally, thereby retracting the cutting element, and the compression member if attached to the cutting element. When the rack 718 reaches its full return, proximal position, a full return sensor (not shown), e.g., a push button switch, can be activated. The full return sensor can be located, for example, at a proximal end of the rack 718 and be activated when the proximal end of the rack 718 abuts a surface of the device 700. Activation of the full return sensor can cause the motor 702 to stop. The ratchet assembly 724 can thus be free to move to its default position on the ledge 734 via force provided by the first spring 720. When the trigger 704 is no longer being pushed, the motor 702 rotates in an opposite direction, e.g., backward, to allow the ratchet assembly 724 to go to the neutral position with the force of the springs 728a, 728b overcoming the motor 702 and forcing the motor 702 to rotate in the opposite direction.

Any time the user stops applying force to the firing trigger 704, e.g., releases the trigger 704, the rack 718 can be allowed to freely return to its default position. The cutting element, and the compression member if attached thereto, can be retracted at any time.

The motor 702 providing supplemental force to the user's manual input force for firing can allow the motor 702 to be smaller and/or lighter than a motor that provides all force for firing. The ratchet assembly 724 can allow the user to move the rack 718 faster than the motor 702 can, hence allowing for user control in firing. By allowing manual user input throughout firing, the user can receive feedback during the firing process, e.g., tactile feedback regarding force, position, and speed, which can provide for a better user experience and/or can facilitate controlled firing.

Figure 35:
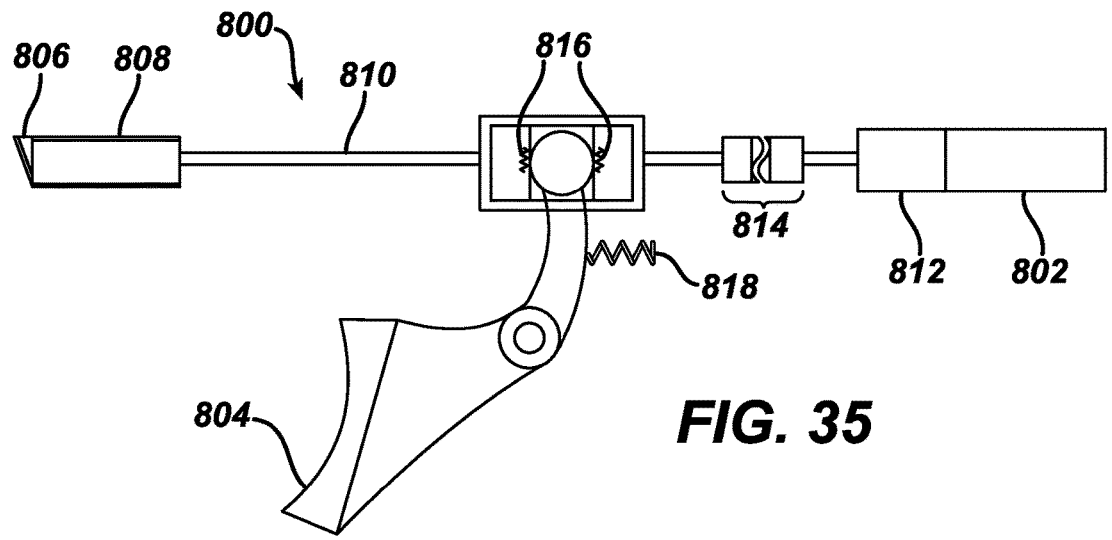
FIG. 35 is a side schematic view of another embodiment of a surgical device configured to adjust an amount of power provided by a motor based on an amount of pressure that a user applies to an actuator.
Figure 36:
FIG. 36 is a cross-sectional view of a compression member of the surgical device of FIG. 35.

FIG. 35 illustrates another embodiment of a surgical device 800 configured to adjust an amount of power provided by a motor 802 based on an amount of pressure that a user applies to an actuator 804, which in this illustrated embodiment includes a firing trigger. The device 800 can generally be configured similar to the device 100 of FIG. 1. The device 800 can include the motor 802, the actuator 804, a controller (not shown), a power source (not shown), an end effector (not shown) that includes a pair of jaws (not shown), a handle housing (not shown), a cutting element 806, a compression member 808 having the cutting element 806 at a distal end thereof, an elongate shaft (not shown), a drive shaft 810 having the compression member 808 and the cutting element 806 at a distal end thereof, a gear box 812, a linear impact mechanism 814, a sensor 816, and a return spring 818. The sensor 816 in this illustrated embodiment includes a plurality of strain gauges, foil strain gauges, etc. The sensor 816 can be attached to the device 800 using various known techniques, e.g., glue, welding, vapor deposition, etc. The motor 802 in this illustrated embodiment includes a linear motor that also includes a rotary component. The cutting element 806 is a knife blade mounted on the compression member 808 in this illustrated embodiment, but the cutting element 806 can have other configurations, as mentioned above. In this illustrated embodiment, as shown in FIG. 36, the compression member 808 is an I-beam having an "I" cross-sectional shape.

The actuator 804 can be directly coupled to the drive shaft 810, such as by being coupled to an intermediate portion thereof as shown in FIG. 35. The actuator 804 can thus be configured to distally advance the cutting element 806 and the compression member 808 through the end effector to their distal-most positions relative to the end effector. The sensor 816 can be configured to sense a force applied by the user to the actuator 804, e.g., an amount of hand pressure applied by the user's finger in pulling the trigger 804 toward a stationary handle (not shown). The sensor 816 can be configured to generate a signal in a Wheatstone bridge and to output the generated signal through an operational amplifier to the controller. The controller can cause the motor's speed to be based on the signal received from the sensor 816. In an exemplary embodiment, the controller can cause the motor's speed to be directly proportional to the signal. The motor's speed can thus be based on an amount of force applied by the user applied to the actuator 804. The user can therefore directly control the speed of firing even with motor-assisted firing. The motor 802 providing proportional power can help compensate for users unable to provide adequate force for firing, e.g., due to low hand strength, tough tissue, thick tissue, etc.

The return spring 818 can be configured to automatically return the actuator 804 to its pre-firing, default position when the user releases the force applied to the actuator 804.

The motor 802 can be configured to cause the linear impact mechanism 814 to rotate, when the motor 802 is on. The rotation of the linear impact mechanism 814 can generate axial pulses on the drive shaft 810 directed in a distal direction. The pulses can be felt at the trigger 804 by the user, thereby allowing the user to receive tactile feedback as to the speed of firing. Stronger pulses generally correspond to faster firing speed.

The device 800 can thus provide proportional position control of the compression member 808 while simultaneously providing force feedback to the user through the firing trigger 804 using vibration from the linear impact mechanism 814. The trigger 804 can maintain direct mechanical coupling to the compression member 808. The device 800 can thereby be configured to provide a reduced force to fire, proportional control, and force feedback. The linear impact mechanism 814 can be a force multiplier, which can allow the motor 802 to provide a relatively small force that can be used produce the force needed for firing, e.g., for advancement of the cutting element 806 and the compression member 808. The vibration from the linear impact mechanism 814 can significantly reduce compression member friction force.

Figure 37:
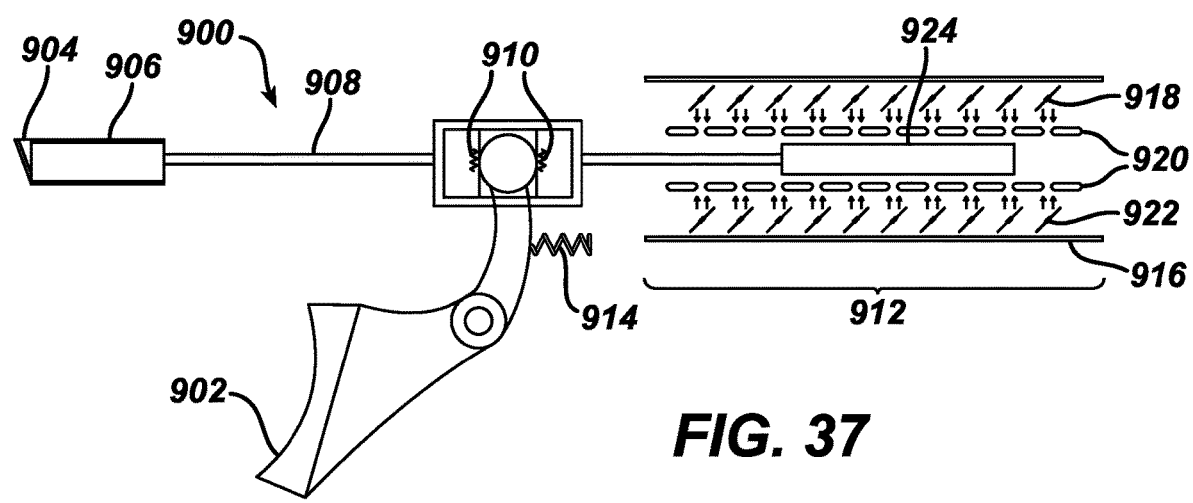
FIG. 37 is a side schematic view of another embodiment of a surgical device configured to adjust an amount of power provided by a motor based on an amount of pressure that a user applies to an actuator.

FIG. 37 illustrates another embodiment of a surgical device 900 configured to adjust an amount of power provided by a motor 924 based on an amount of pressure that a user applies to an actuator 902, which in this illustrated embodiment includes a firing trigger. The device 900 can generally be configured similar to the device 100 of FIG. 1. The device 900 can include the motor 924, the actuator 902, a controller (not shown), a power source (not shown), an end effector (not shown) that includes a pair of jaws (not shown), a handle housing (not shown), a cutting element 904, a compression member 906 having the cutting element 904 at a distal end thereof, an elongate shaft (not shown), a drive shaft 908 having the compression member 906 and the cutting element 904 at a distal end thereof, a gear box (not shown), a linear accelerator 912, a return spring 914, and a sensor 910. The sensor 910, the return spring 918, the cutting element 904, and the compression member 906 in this illustrated embodiment are the same as the sensor 816, the return spring 818, the cutting element 806, and the compression member 808 of FIG. 35, respectively. In this illustrated embodiment, the motor 924 includes a linear motor, and the linear accelerator 912 includes an infrared photo diode 918, an electromagnet 920, an infrared LED linear array 922, and a shield 916. The shield 916 in this illustrated embodiment is an Mu-metal shield. Similar to that discussed above with respect to FIG. 35, the actuator 902 can be directly coupled to the drive shaft 908, such as by being coupled to an intermediate portion thereof as shown in FIG. 37, and the controller can be configured to cause the motor's speed to be based on an output signal received from the sensor 910, e.g., be proportional to the user's input force.

The infrared LED linear array 922 and the infrared photo diode 918 can be configured to sense an edge of a core of the motor 924 to turn coils of the electromagnet 920 on and off as needed. The shield 916 can enclose the motor 924, as shown in FIG. 37, which can help prevent magnetic interference from any nearby electronic devices.

The motor 924 can include a three phase outrunner motor where an outside of the motor 924 spins and a center shaft of the motor 924 is fixed. The outrunner motor can be coupled directly with a lead screw of the device or via a single stage of a spur gear reduction to a lead screw. The outrunner motor can allow the motor 924 to provide relatively high torque in a relatively compact package, thereby allowing the device to include a motor 924 that is less costly, have less weight, and be less complex than other motors, such as a conventional motor with planetary or spur gear reduction systems.

Figure 38:
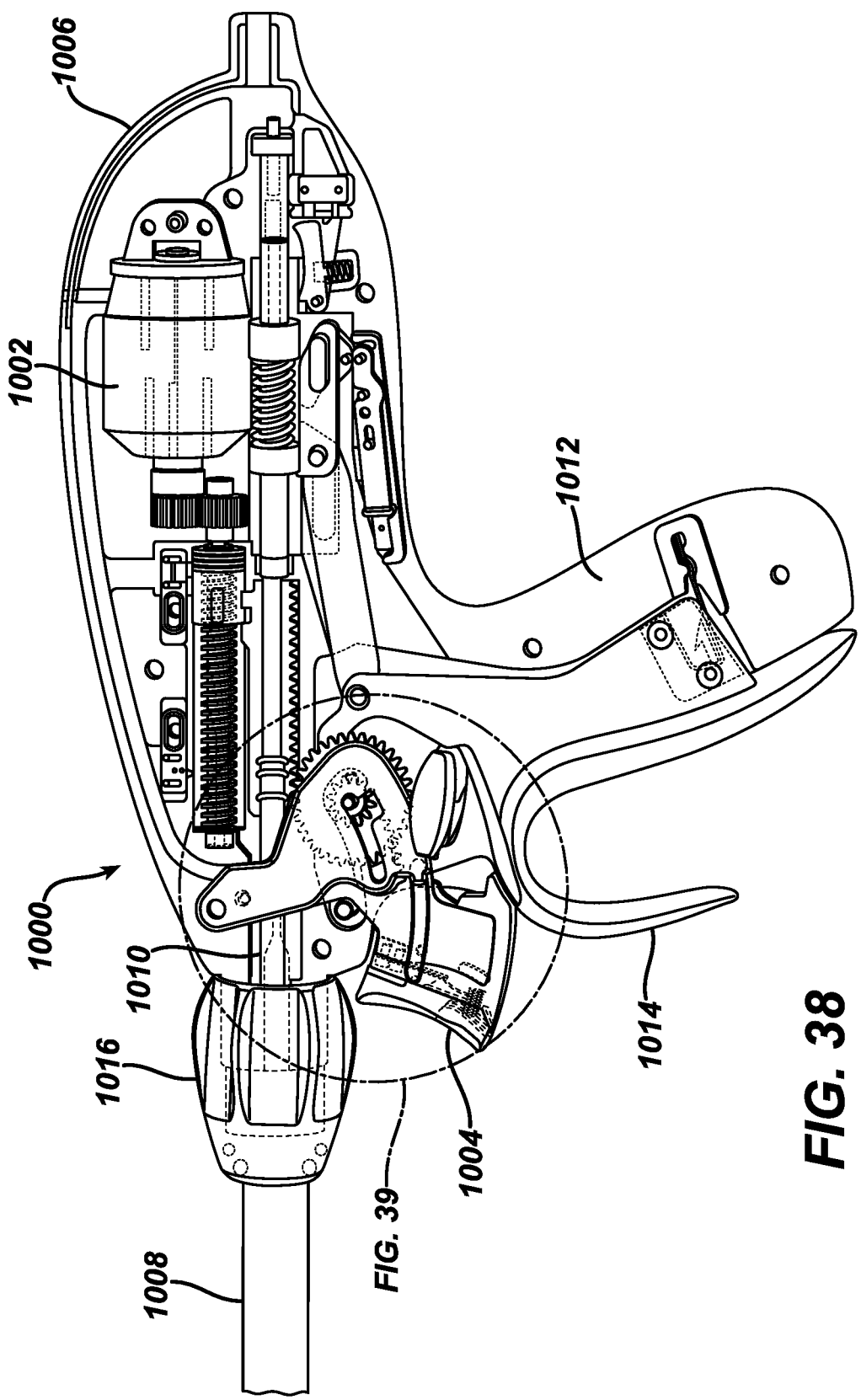
FIG. 38 is a side schematic view of another embodiment of a surgical device configured to adjust an amount of power provided by a motor based on an amount of pressure that a user applies to an actuator.
Figure 39:
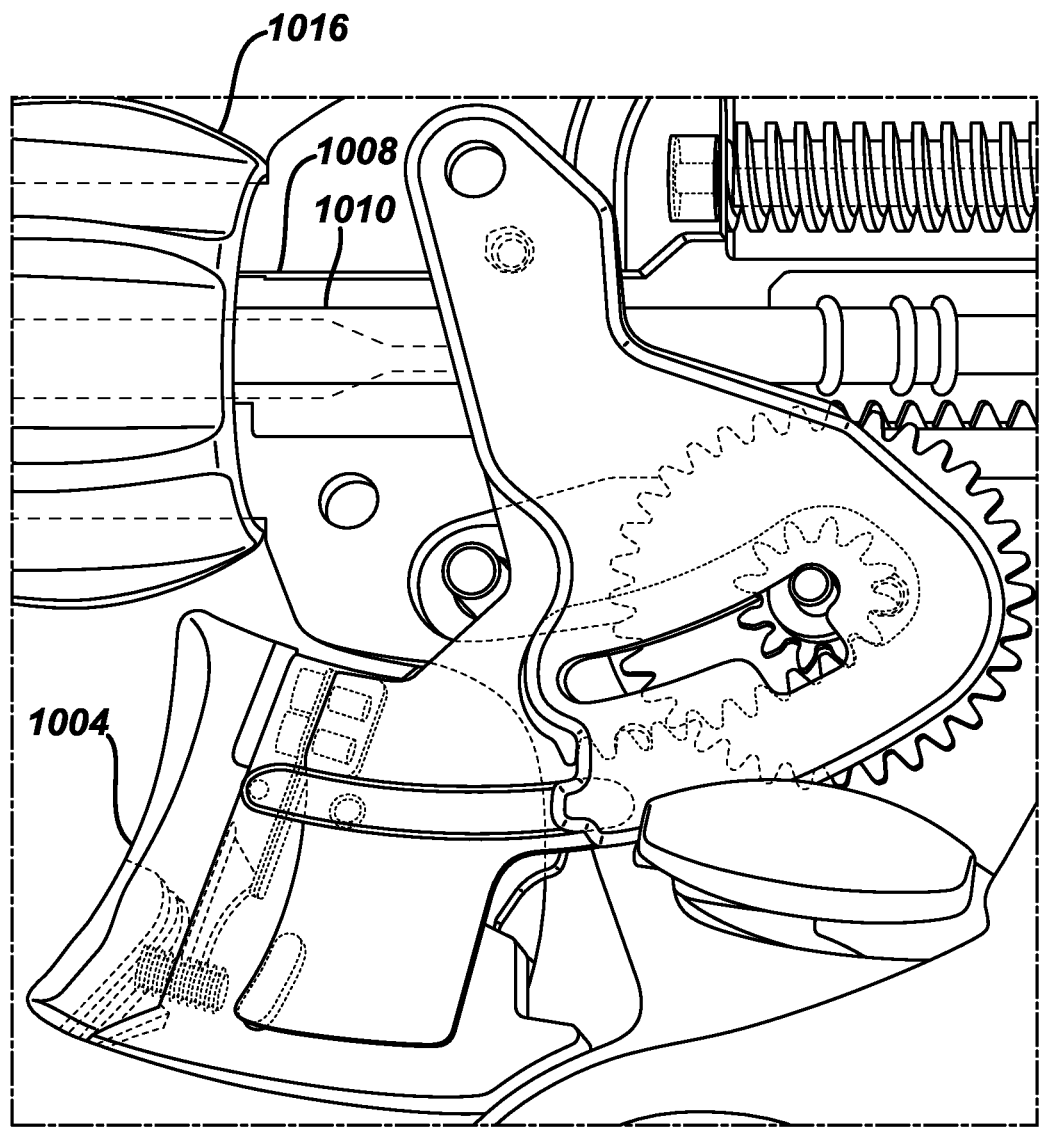
FIG. 39 is a side schematic view of the surgical device of FIG. 38 including an actuator mechanism thereof.
Figure 40:
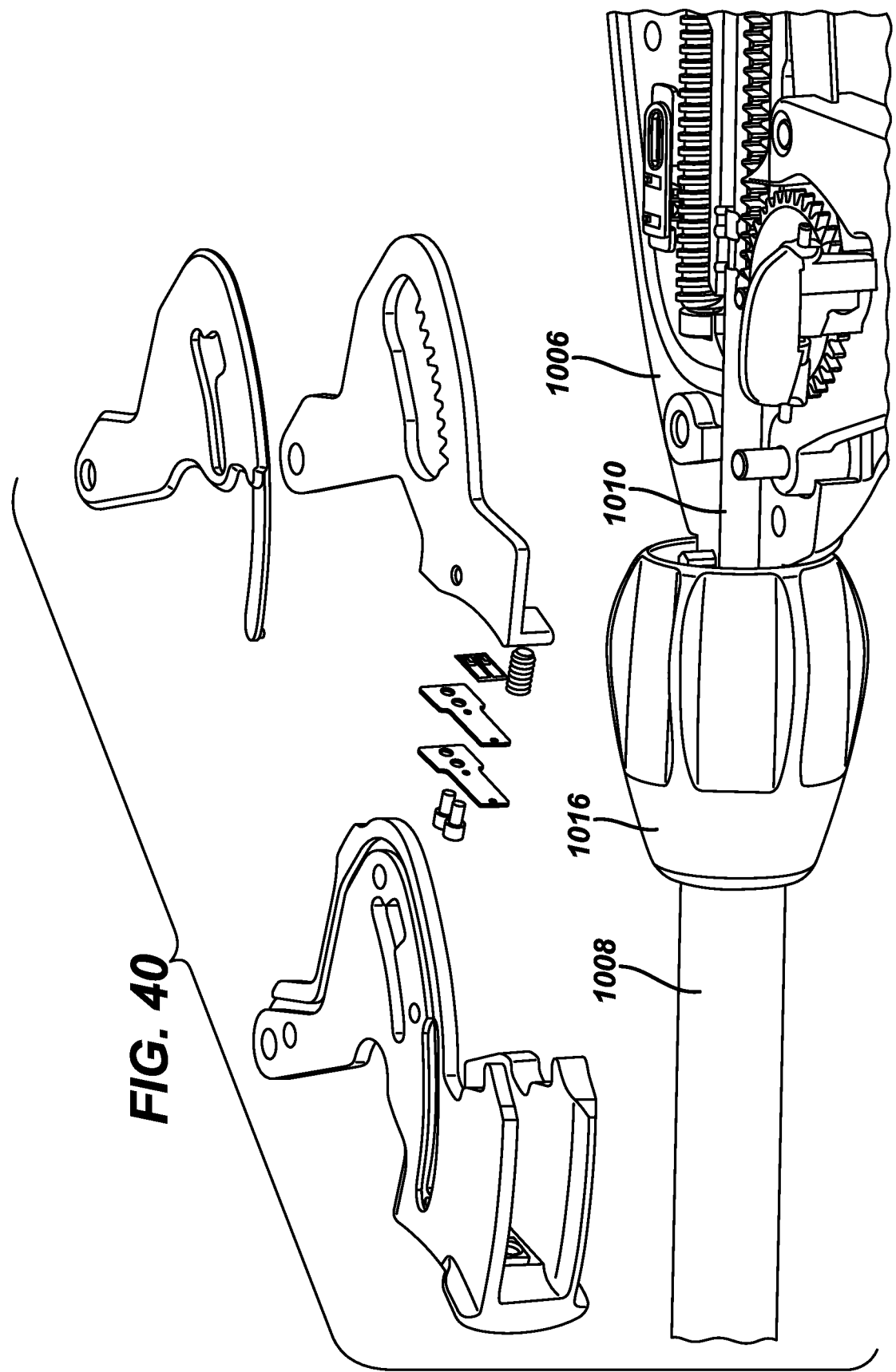
FIG. 40 is an exploded partial view of the surgical device of FIG. 38.

FIG. 38 illustrates another embodiment of a surgical device 1000 configured to adjust an amount of power provided by a motor 1002 based on an amount of pressure that a user applies to an actuator 1004, which in this illustrated embodiment includes a firing trigger. The device 1000 can generally be configured similar to the device 100 of FIG. 1. The device 1000 can include the motor 1002, the actuator 1004, a controller (not shown), a power source (not shown), an end effector (not shown) that includes a pair of jaws (not shown), a handle housing 1006, a cutting element (not shown), a compression member (not shown), an elongate shaft 1008 extending distally from the housing 1006, a drive shaft 1010 having the compression member and the cutting element at a distal end thereof, a stationary handle 1012, a clamping trigger 1014, an actuator mechanism, a knob 1016 configured to rotate the shaft 1008 about a longitudinal axis thereof, a distal trigger plate, a set screw, and a return spring. The actuator mechanism, also shown in FIGS. 39 and 40, can include a leaf spring and a sensor. The compression member in this illustrated embodiment can include an I-beam having the cutting element attached thereto.

The sensor can be configured to sense user force input to the actuator 1004. The actuator mechanism can allow for a small degree of the actuator's motion through a sensing range of the sensor, which can facilitate intuitive operation of the device 1000. The motion through the sensing range can be proportional to the force applied by the user.

When the user applies a force to the actuator 1004, e.g., by pulling the trigger 1004 with a finger, the actuator 1004 can deflect under the applied load. The sensor can be configured to sense the applied force, such as by measuring a change in strain gauge resistance. The sensor can be configured to output a signal to the controller that indicates the sensed applied force, and the controller can cause the motor's speed to be directly proportional to the signal. The set screw can be located in the distal trigger plate, which can provide an adjustable stop allowing the total travel of the actuator 1004 to be adjusted.

Figure 41:
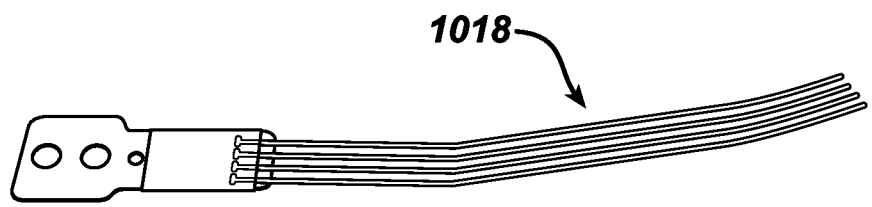
FIG. 41 is a perspective view of an embodiment of a strain gauge.

The sensor in this illustrated embodiment includes a strain gauge. FIG. 41 illustrates an embodiment of a strain gauge in the form of an analog strain gauge 1018. In other embodiments, the sensor can include an analog photoelectric sensor (e.g., an emitter/detector pair, etc.), a load cell in series with a compression spring, a potentiometer in series with a tension spring, or a piezoresistor in series with a leaf spring. Any number of sensors can be used.

Figure 42:
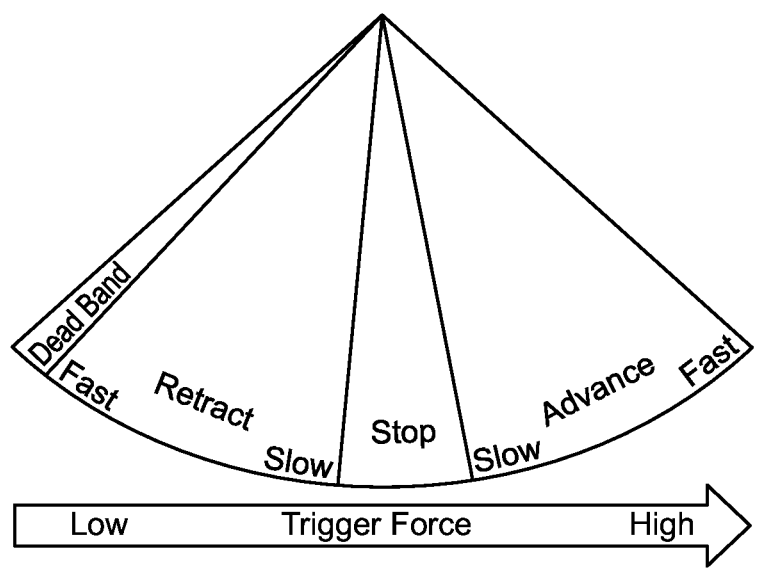
FIG. 42 is a continuum of an embodiment of how a controller can correspond a signal output by a sensor to a speed of a motor.

Referring again to FIG. 1, the device 100 can be configured to adjust an amount of power provided by the motor 32 based on an amount of pressure that the user applies to an actuator, as discussed above, and be configured to control drive direction of the motor 32 based on the amount of pressure. FIG. 42 illustrates a continuum of how a controller can correspond a signal output by a sensor to a speed of a motor. A left hand edge of the continuum represents zero displacement of the actuator, e.g., the clamping trigger 20 or to the firing actuator 24, corresponding to a zero voltage signal system input. Directly to the left of the left hand edge is a "Dead Band" zone corresponding to a low level of input force. The "Dead Band" zone accommodates minor sensor drift from the initial zero value during device operation. Application of additional force to the actuator can cause increased force applied to the sensor and hence increased voltage, corresponding to a "Retract" zone in the continuum in which speed of the motor 32 decreases from a first speed to a second, slower speed and the compression member retracts, e.g., moves proximally. The device 100 can include a proximally located electrical limit switch (not shown) configured to signal the controller 34 to stop the motor 32 from further retracting the compression member when the proximal electrical limit switch is activated, e.g., when the proximal electrical limit switch closes. Further application of force to the actuator can allow the compression member to halt retraction at any point along its stroke length. The stop is reflected by the "Stop" zone in the continuum. The stop can help prevent operator induced oscillation. Application of additional force to the actuator can move into the "Advance" zone of the continuum in which the controller 34 can cause the motor 32 to move from a first speed to a second, faster speed in order to advance the compression member distally. The device 100 can include a distally located limit switch (not shown) configured to signal the controller 34 to stop the motor 32 from further advancing the compression member when the distal electrical limit switch is activated, e.g., when the distal electrical limit switch closes. The different bands of the continuum shown in FIG. 42 can allow for movement of the compression member proportional to a position of the actuator within the continuum, or the actuator can instead create a change in a logic state of the device 100 such that location of the actuator within specific portions of the continuum, e.g., within different ones of the bands, can creates a specific change in the logic state, such as having the motor change its speed from a slow rate to a fast rate once the actuator reaches a specified point in the continuum, as opposed to proportional control of the motor across the entire width of the continuum. The device 1000 is an example of a device that can be operated over the continuum, such as if the device 1000 includes a sensor coupled to the closure trigger 1014 that is configured to provide a signal to the controller that the controller can use to control the motor 1002 according to the continuum of FIG. 42.

Referring again to FIG. 1, the device 100 can be configured to maintain a force applied to the device 100 when the force reaches a predetermined force. In an exemplary embodiment, the force can be applied to the closure grip 20 so as to maintain a clamping force on tissue clamped by jaws of the device's end effector.

Figure 43:
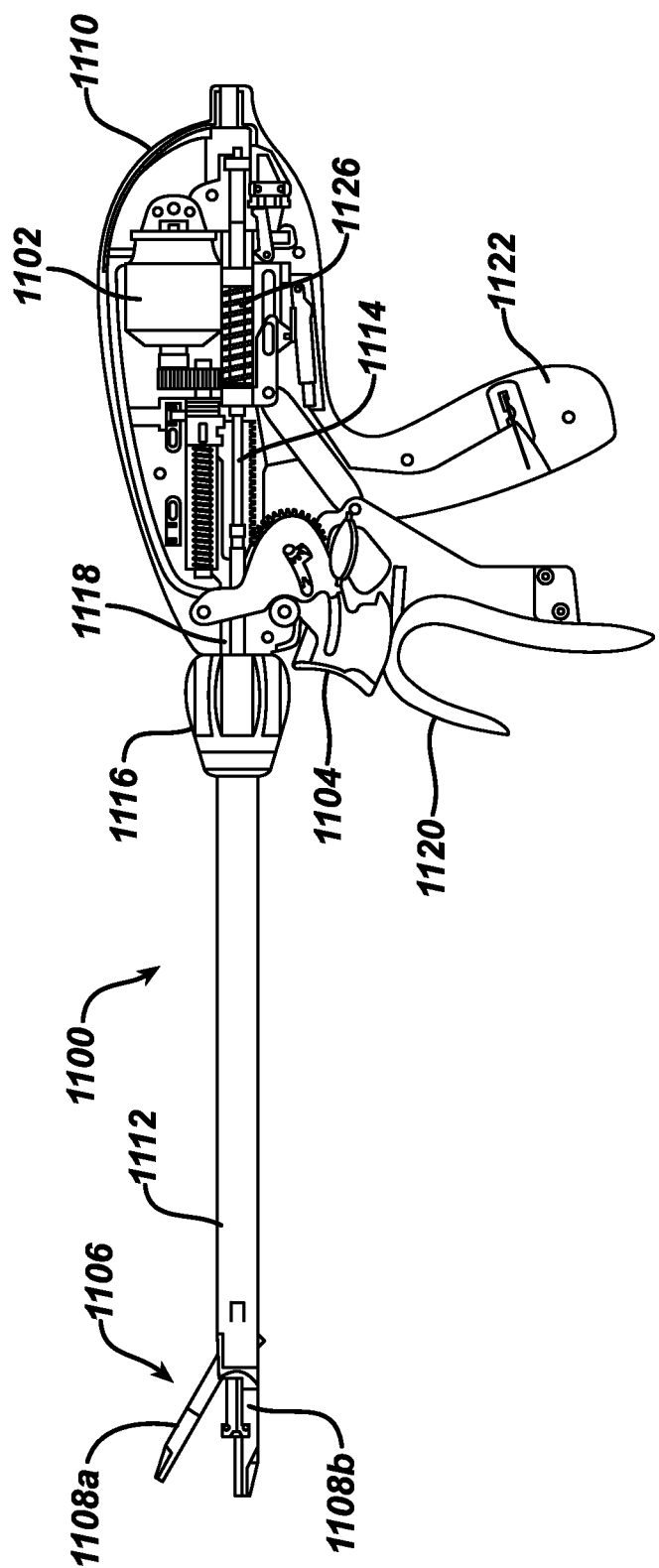
FIG. 43 is a side schematic view of an embodiment of a surgical device that can be configured to maintain a force applied to the device when the force reaches a predetermined force.

FIG. 43 illustrates one embodiment of a device 1100 that can be configured to maintain a force applied to the device 1100 when the force reaches a predetermined force. The device 1100 can generally be configured similar to the device 100 of FIG. 1. The device 1100 can include a motor 1102, a firing trigger 1104, a controller (not shown), an end effector 1106 that includes a pair of jaws 1108a, 1108b, a handle housing 1110, a cutting element (not shown), a compression member (not shown), an elongate shaft 1112 extending distally from the housing 1110, a drive shaft 1114 having the compression member and the cutting element at a distal end thereof, a knob 1116 configured to rotate the shaft 1112 about a longitudinal axis thereof, a jaw closure tube 1118, a sensor (not shown), a notification mechanism (not shown), a closure trigger 1120, and a stationary handle 1122. The sensor can include, for example, a strain gauge or a solenoid. The device 1100 in this illustrated embodiment is configured to be connected to an external power source (not shown), although as mentioned above, the device 1100 could instead be configured to have an on-board power source. The device 1100 can be configured to provide RF energy.

The sensor can be attached to the jaw closure tube 1118, e.g., to a distal end thereof as in the illustrated embodiment (the jaw closure tube's distal end is obscured in FIG. 43). When the sensor senses a predetermined force, the sensor can be configured to transmit a signal to the controller indicating that the predetermined force has been met. The predetermined force can be preprogrammed into the controller. In response to the signal from the sensor, the controller can be configured to cause the closure trigger 1120 having the user force applied thereto to be locked in position using a locking mechanism. The locking mechanism can have a variety of configurations, as will be appreciated by a person skilled in the art, such as a latch configured to automatically latch onto the closure trigger 1120 when the closure trigger 1120 has been pulled a certain amount toward the stationary handle 1122. Also in response to the signal from the sensor, the controller can be configured to cause the notification mechanism to provide a notification that can be visually and/or audibly perceived by the user. Examples of the notification mechanism include a light (e.g., an LED, etc.) and an audio speaker. Examples of the notification include illuminating the light and providing a sound, e.g., a beep, a series of tones, etc., through the audio speaker. The notification can notify the user that the predetermined force has been achieved and that, therefore, the user can stop providing the force to the device 1100, e.g., can stop pulling the closure trigger 1120. The locking mechanism can hold the closure trigger 1120 in position without the user providing force thereto. The clamping of the jaws 1008a, 1008b caused by actuation of the closure trigger 1120 can thus be maintained. When firing is complete, e.g., when RF energy has been applied to clamped tissue, when clamped tissue has been cut, etc., the controller can be configured to release the locking mechanism.

The device 1100 can include a firing safety mechanism configured to prevent firing until the closure trigger 1120 is locked in position, thereby indicating that the end effector 1106 is closed. The firing safety mechanism can have a variety of configurations, such as a mechanical or electrical sensor (e.g., a Hall sensor, etc.) coupled to the closure trigger 1120 or to the end effector 1106.

The motor 1102 can be configured to provide jaw closure force. In such embodiments, the sensor can be configured to sense when the force applied to close the jaws 1108a, 1008b reaches the predetermined force, whether the force is being applied by the user alone, by the motor 1102 alone, or by a combination of the user and the motor 1102. The motor 1102 can be configured to reverse direction to open the end effector 1106, similar to that discussed above.

The motor 1102 can be configured to drive a compression member to a distal tip of the end effector 1106, e.g., to distal tips of the jaws 1108a, 1008b, which can facilitate tissue clamping and, if a cutting element is attached to the compression member, tissue cutting. Having the compression member move to the distal tip of the end effector 1106 can help keep the jaws 1108a, 1108b apart at at least a minimum distance, even if a lot of force is being applied manually by a user and/or by a motor to close the end effector 1106. This can help prevent tissue damage, help prevent damage to the device, and/or facilitate movement of the cutting element through the tissue. Any of the devices disclosed herein can be so configured to drive a compression member to a distal tip of an end effector.

Figure 43A:
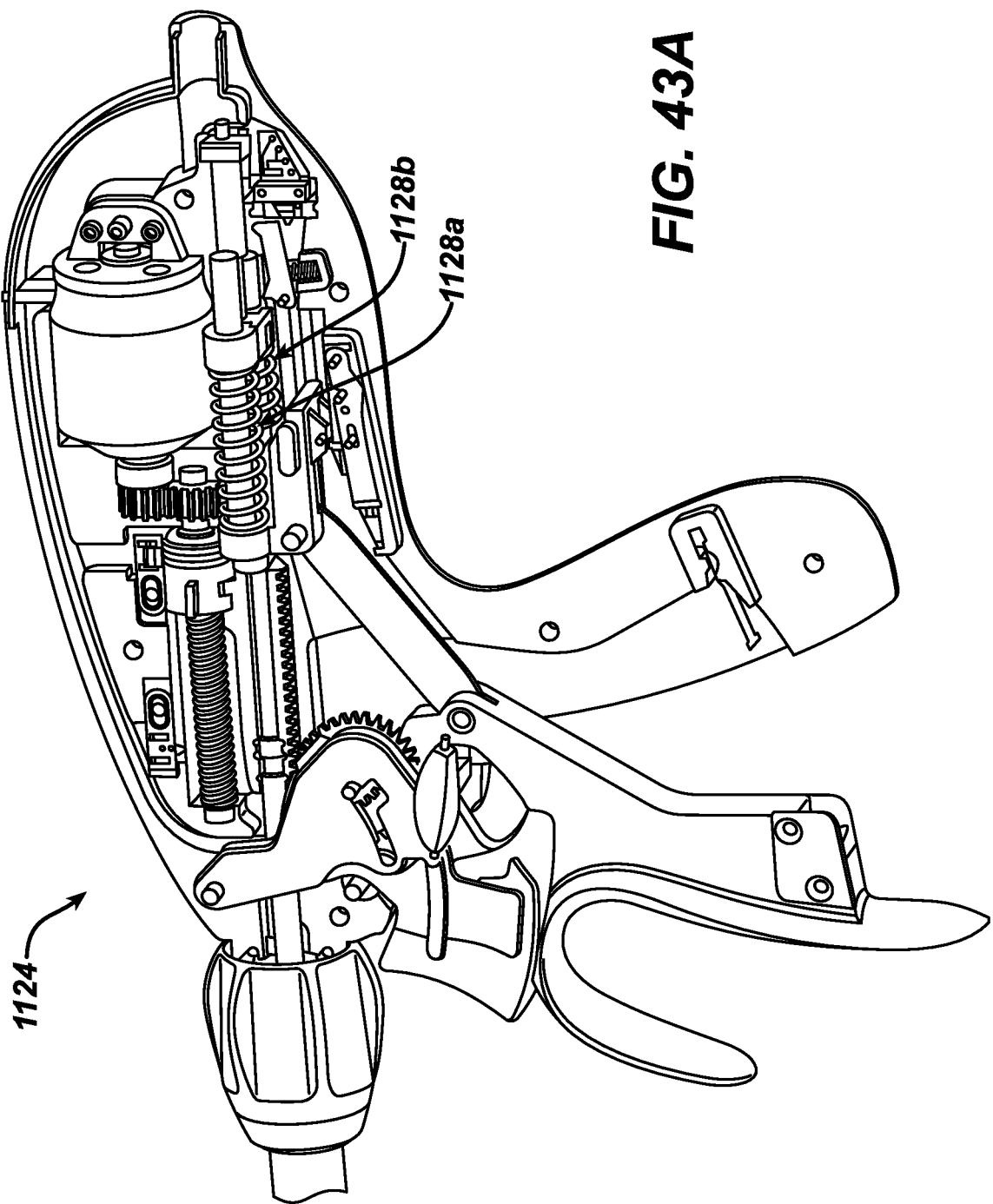
FIG. 43A is a perspective view of an embodiment of a surgical device that includes a single closure spring configured to assist with closure and opening of the device's jaws.

FIG. 43A illustrates a device 1124 that can be an alternate embodiment of the device 1100 of FIG. 43. The device 1100 of FIG. 43 includes a single spring 1126 configured to assist with closure and opening of the jaws 1108a, 1108b. The spring 1126 can be compressed when the jaw closure tube 1118 is moved proximally to close the end effector 1106, and the spring 1126 can expand and return to its default biased state when the end effector 1106 opens. The device 1124 of FIG. 43A includes two springs 1128a, 1128b configured to assist with closure and opening of the device's jaws (not shown). Having two springs 1128a, 1128b instead of one spring 1126 can allow for smaller springs, which can help provide space inside the device's handle for a motor and/or can help allow for the device's handle to be smaller. Any of the device embodiments described herein that has a spring-driven jaw closure tube can include two springs instead of one similar to the device 1124 of FIG. 43A.

Figure 43B:
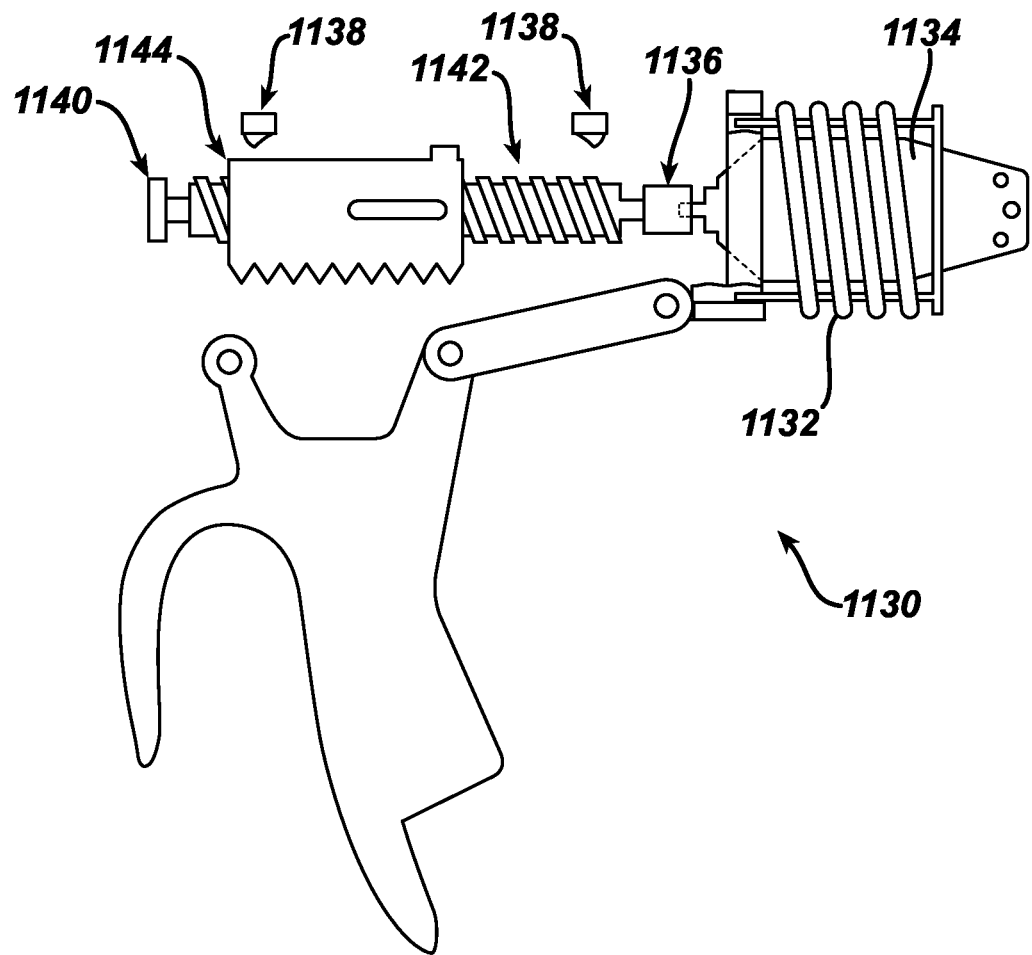
FIG. 43B is a side schematic view of an embodiment of a surgical device that includes a closure spring at a location that is displaced from a motor of the surgical device.

FIG. 43B illustrates a device 1130 that can be an alternate embodiment of the device 1100 of FIG. 43. The device 1100 of FIG. 43 includes the spring 1126 at a location that is displaced from the motor 1102. The device 1130 of FIG. 43B includes a spring 1132 that can be configured to assist with closure and opening of an end effector (not shown), that can replace the spring 1126 of FIG. 43, that can be at a location that is not displaced from a motor 1134, e.g., from the motor 1102. The spring 1132 can be located along a longitudinal axis of a drive shaft that drives a cutting element. The motor 1134 can be nested within the spring 1132, e.g., the spring 1132 can be coiled around the motor 1134. The motor 1134 and the spring 1132 can thus both be located along the drive shaft's longitudinal axis. The spring 1132 not being displaced from the motor 1134 can help reduce a center of gravity of the device 1130, which can help reduce hand fatigue, can help reduce a part count of the device 1130, and/or can help conserve axial space, which can help provide space inside the device's handle for a motor and/or can help allow for the device's handle to be smaller. To facilitate use of the spring 1132, the device 1130 can include a coupler 1136, two limit switches 1138, a bearing 1140, a lead screw 1142, and a nut 1144. The lead screw 1142 and the nut 1144 can have, for example, corresponding acme threads. Any of the device embodiments described herein that has a spring-driven jaw closure tube can include a spring that is not displaced from the device's motor similar to the device 1130 of FIG. 43B.

Referring again to FIG. 1, the device 100 can be configured to self-shift the motor 32 between two different speeds. In other words, a user need not provide input to the device 100 requesting faster or slower motor speed. Instead, the device 100 can be configured to dynamically adjust the motor's speed. The device 100 can be configured to automatically move between motor gears, one gear in which the motor drives at the faster speed and another gear in which the motor drives at the slower speed. In some embodiments, the device 100 can be configured such that when the motor 32 is driving in the first direction so as to close the jaws 16a, 16b, the motor 32 can close the jaws 16a, 16b at a first speed, and when the motor 32 is driving in the second direction so as to open the jaws 16a, 16b, the motor 32 can open the jaws 16a, 16b at a second speed that is different than the first speed. The first speed can be greater than the second speed since it can require more force to close the end effector 14 around tissue than release the end effector 14 from tissue. In some embodiments, the device 100 can be configured such that when the motor 32 is driving in the first direction so as to advance the compression member and/or the cutting element distally through the end effector 14, the motor 32 can advance the compression member and/or the cutting element at a first speed, and when the motor 32 is driving in the second direction so as to retract the compression member and/or the cutting element proximally through the end effector 14, the motor 32 can open retract the compression member and/or the cutting element at a second speed that is different than the first speed. The first speed can be greater than the second speed since it can require more force to advance the compression member and/or the cutting element distally when the end effector 14 is clamping tissue than when the compression member and/or the cutting element are being retracted through cut and/or fastened tissue.

In some embodiments, the device 1100 of FIG. 43 can be modified to include the features of devices described herein that are configured to self-shift a motor, with or without the features related to maintaining a force applied to the device when the force reaches a predetermined force. Similarly, in some embodiments, the device 1124 of FIG. 43A can be modified to include the features of devices described herein that are configured to self-shift a motor, with or without the features related to maintaining a force applied to the device when the force reaches a predetermined force.

Figure 44:
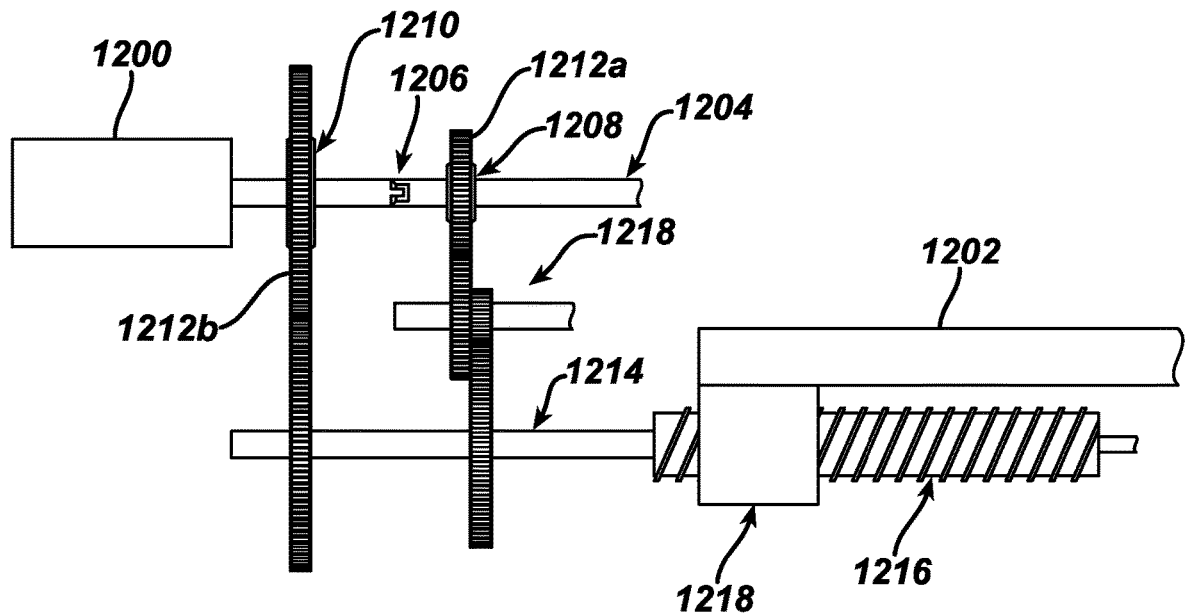
FIG. 44 is a side perspective view of an embodiment of a surgical device configured to self-shift a motor between two different speeds.
Figure 45:
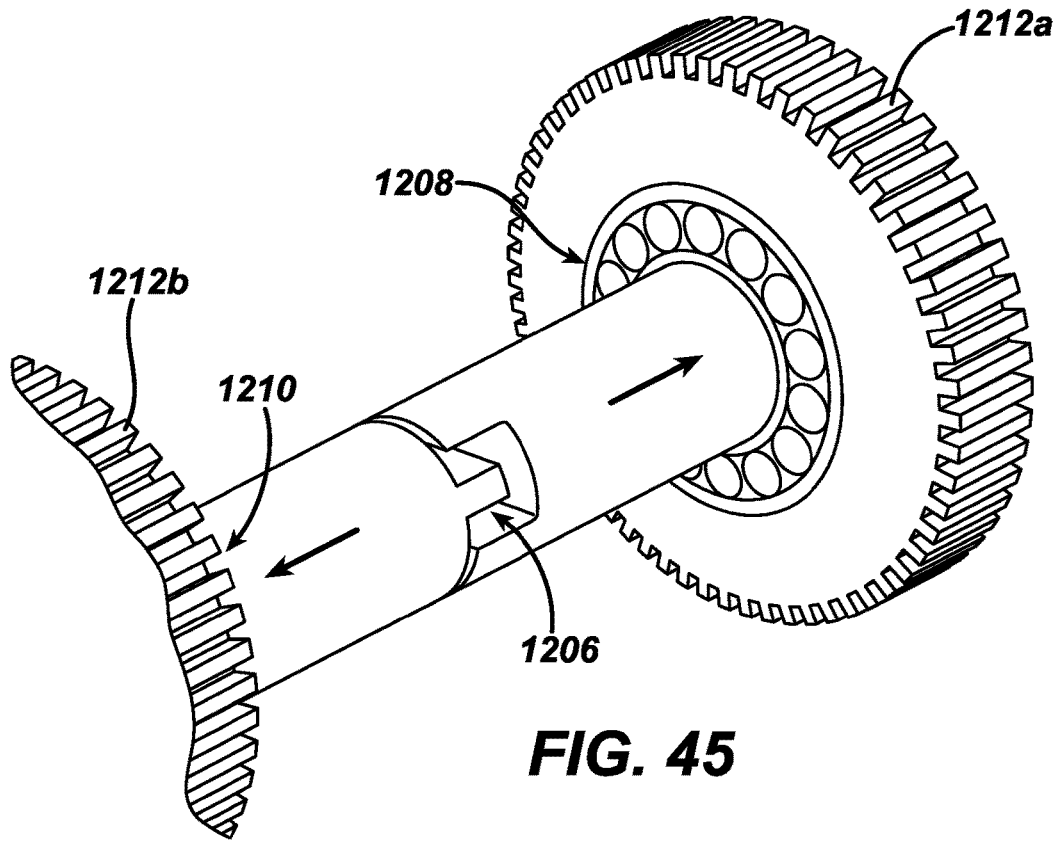
FIG. 45 is a perspective view of a portion of the surgical device of FIG. 44.

FIG. 44 illustrates one embodiment of a device configured to self-shift a motor 1200 between two different speeds. The device can be configured to adjust power provided by the motor 1200 based on a drive direction of the motor 1200, e.g., whether the motor 1200 is driving in a first direction, e.g., clockwise, or in a second direction, e.g., counterclockwise. The speed of the motor 1200 can thus be controlled based on the motor's drive direction. The device can generally be configured similar to the device 100 of FIG. 1. The device can include the motor 1200, a firing trigger (not shown), a controller (not shown), an end effector (not shown) that includes a pair of jaws (not shown), a handle housing (not shown), an elongate shaft (not shown) extending distally from the housing, a drive shaft 1202, a knob (not shown) configured to rotate the shaft about a longitudinal axis thereof, a closure trigger (not shown), a stationary handle (not shown), a motor shaft 1204 that includes a slip joint 1206, a first one way bearing 1208 attached to the motor shaft 1204 on one side of the slip joint 1206 (see FIG. 45), a second one way bearing 1210 attached to the motor shaft 1204 on another side of the slip joint 1206, a first gear 1212a, a second gear 1212b, a compound gear or gear train 1218, a screw shaft 1214, a screw 1216 attached to the screw shaft 1214, a nut 1218 threadably engaged with the screw 1216. The drive shaft 1202 can include a jaw closure tube and/or can be a member having a compression member and a cutting element at a distal end thereof. In this illustrated embodiment, the drive shaft 1202 includes a member having a compression member and a cutting element at a distal end thereof. The motor 1200 can be configured to drive the compression member and the cutting element distally at one speed and to drive the compression member and the cutting element proximally at a different speed.

The gear train 1212 can include a plurality of gears 1212a, 1212b. The first gear 1212a can be directly attached to the motor shaft 1204 through the first one way bearing 1208, and the first gear 1212a can be configured to rotate only in a first direction. The second gear 1212b can be directly attached to the motor shaft 1204 through the second one way bearing 1210, and the second gear 1212b can be configured to rotate only in a second direction that is opposite to the first direction. The first gear 1212a can engage the compound gear 1218 before it attaches to the screw 1216. The first gear 1212a can be configured to provide a speed to the drive shaft 1202 that is slower than a speed provided by the second gear 1212b. The first gear 1212a can thus be configured to provide a mechanical advantage to the device.

The motor shaft 1204 can be configured to drive the first and second gears 1212a, 1212b. The motor shaft 1204 can include two halves with the slip joint 1206 at a junction of the two halves. The slip joint 1206 can be a loose fit such that when the motor shaft 1204 changes rotational direction, the motor shaft 1204 can rotate a small amount before engaging the other half of the shaft 1204. This small amount of rotation can allow the motor shaft 1204 to build up momentum and break loose the opposite one directional bearing when reversing direction. When the motor shaft 1204 rotates in a forward-moving direction, the first one way bearing 1208 can be locked, thereby allowing the gears of the compound gear 1218 to rotate. The second one way bearing 1210 can be free to rotate when the motor shaft 1204 rotates in a forward-moving direction. When the motor shaft 1204 rotates in a reverse-moving direction, the second one way bearing 1210 can be locked, and the first one way bearing 1208 can freely rotate. In this way, the forward and reverse directions can have different speeds and mechanical advantages, and no complex shifting would be necessary.

Figure 46:
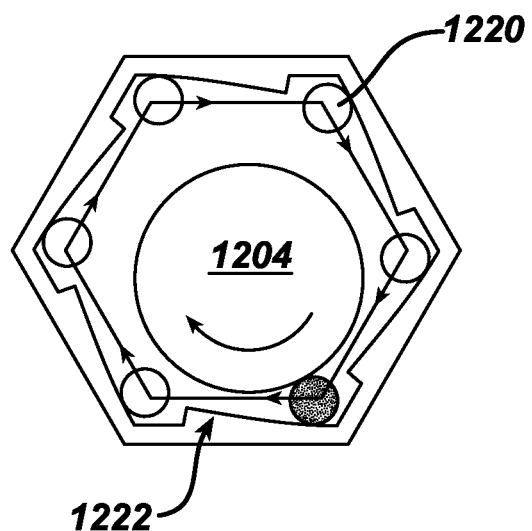
FIG. 46 is a side schematic view of an embodiment of a one way bearing and a motor shaft.
Figure 47:
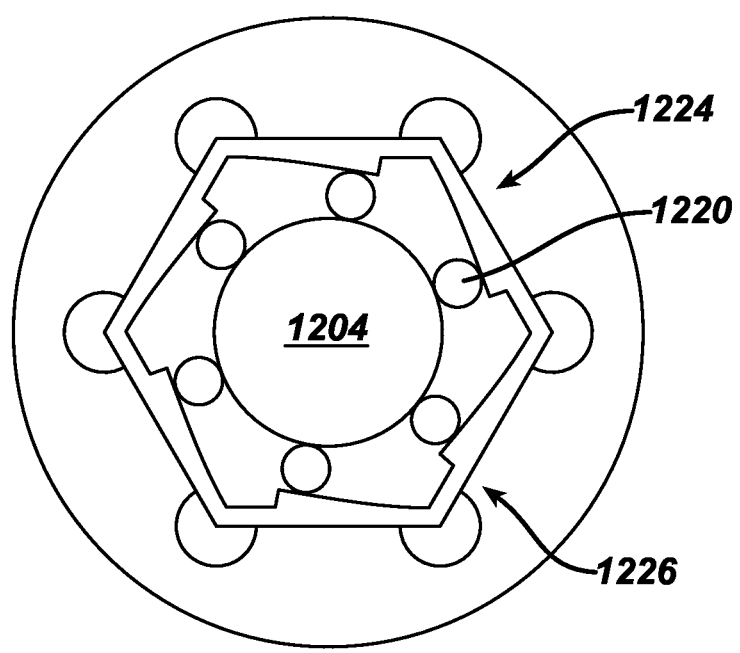
FIG. 47 is a side schematic view of another embodiment of a one way bearing and a motor shaft.
Figure 48:
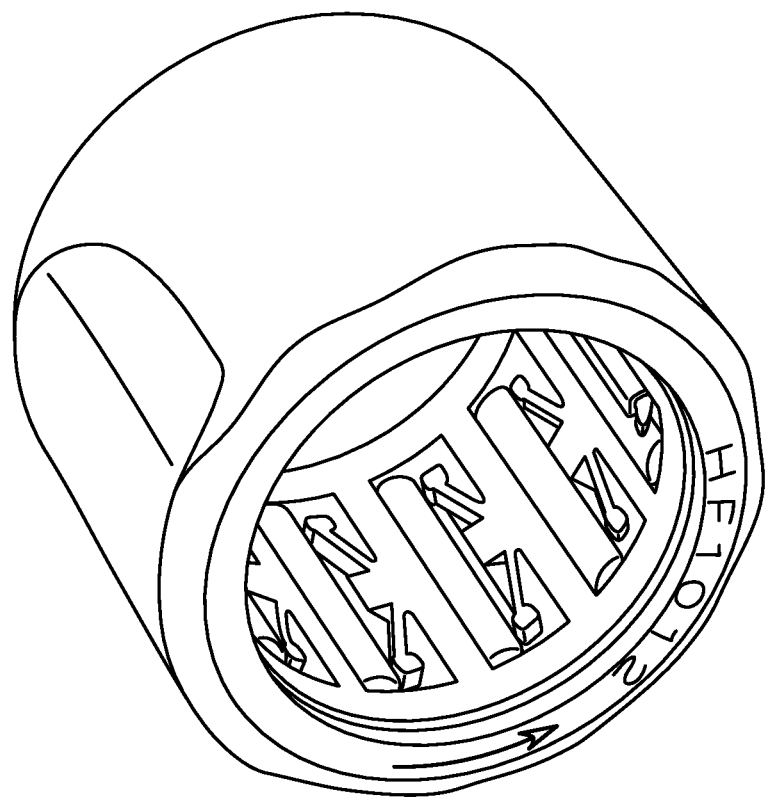
FIG. 48 is a perspective view of another embodiment of a one way bearing and a motor shaft.

FIGS. 46-48 illustrate embodiments of one way bearings. FIGS. 46 and 47 show the motor shaft 1204 relative thereto for clarity. The one way bearings of FIGS. 46 and 47 each include a plurality of bearing pins 1220. A shaded one of the pins 1220 in FIG. 46 can be a first one of this bearing's pins 1220 to contact the shaft 1204, as shown in FIG. 46. A plane 1222 shown in FIG. 46 indicates a plane that the shaded pin 1220 can travel on. Each of the pins 1220 can have a similar plane on which to travel. The shaded pin 1220 can push the bearing's outer case outwards, making an opposite side of the outer case come closer to the shaft 1204, thereby causing the other pins 1220 of the bearing to begin contacting the shaft 1204. The pins 1220 can similarly function in the bearing of FIG. 47. FIG. 47 shows a shaded lubricant area 1224 that can be packed with a lubricant such as grease. A clearance 1226 can be enough to allow the bearing's outer case to center itself around the motor shaft 1204 as the pins 1220 engage the shaft 1204 and a positive lock is developed. The clearance 1226 is shown larger in FIG. 47 than would be necessary, for clarity of description.

Referring again to FIG. 1, the device 100 can be configured to adjust an amount of power provided to the end effector 14 based on a degree of the end effector's closure, e.g., based an amount of closure of the jaws 16a, 16b. For example, the device's closure grip 20 can be coupled to a hub configured to dynamically provide varying amounts of power for closing and for opening the end effector 14. If a device, e.g., the device 100 of FIG. 1, the device 1100 of FIG. 43, the device 1124 of FIG. 43A, etc., the device can, but need not, include a motor, a controller, or a power source.

A hub can be configured to dynamically move between a low gear in which a maximum amount of torque is provided for end effector closure/opening and a high gear in which a minimum amount of torque is provided for end effector closure/opening. The hub can be configured to gradually increase in gear from the low gear to the high gear so as to gradually decrease the amount of torque as the hub moves toward the high gear. Similarly, the hub can be configured to gradually decrease in gear from the high gear to the low gear so as to gradually increase the amount of torque as the hub moves toward the high gear. In other words, the hub can be configured to continuously ramp up torque when moving toward the low gear and to continuously ramp down torque when moving toward the high gear. The hub can thus be configured to create or vary mechanical advantage, which can facilitate end effector closure when the jaws are closing around thick, tough, irradiated, and/or calcified tissue. In an exemplary embodiment, the hub can move toward the low gear during end effector closure, e.g., gradually increase torque when closing the end effector, which can help provide more power for the closure as the jaws clamp around tissue.

Figure 49:
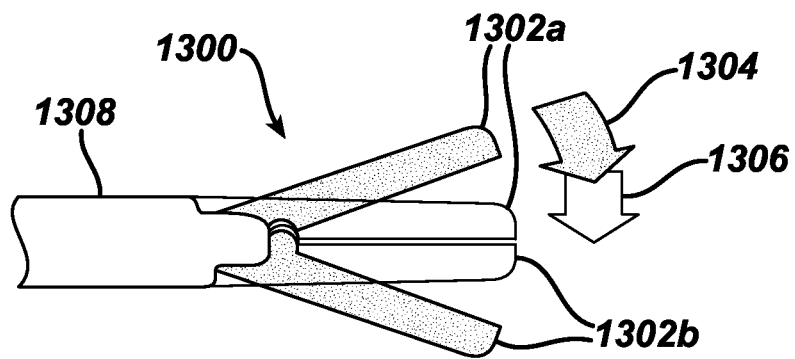
FIG. 49 is a side schematic view of an embodiment of end effector closure using different gears.

FIG. 49 shows an embodiment of a device's end effector 1300 that includes first and second jaws 1302a, 1302b and that can be configured to be coupled to a hub (not shown) configured to dynamically change the speed of the end effector's closure and opening. In this illustrated embodiment, a shaded arrow 1304 indicates a high gear, low torque movement of the jaws 1302a, 1302b as shaded in FIG. 49, and an unshaded arrow 1306 indicates a low hear, high torque movement of the jaws 1302a, 1302b as unshaded in FIG. 49. The jaws 1302a, 1302b can thus be configured to close with more and more power the closer that facing surfaces of the jaws 1302a, 1302b become to one another. FIG. 49 also shows the end effector 1300 coupled to an elongate shaft 1308 with each of the jaws 1302a, 1302b having a proximal end pivotally coupled to the distal end of the elongate shaft 1308.

Figure 50:
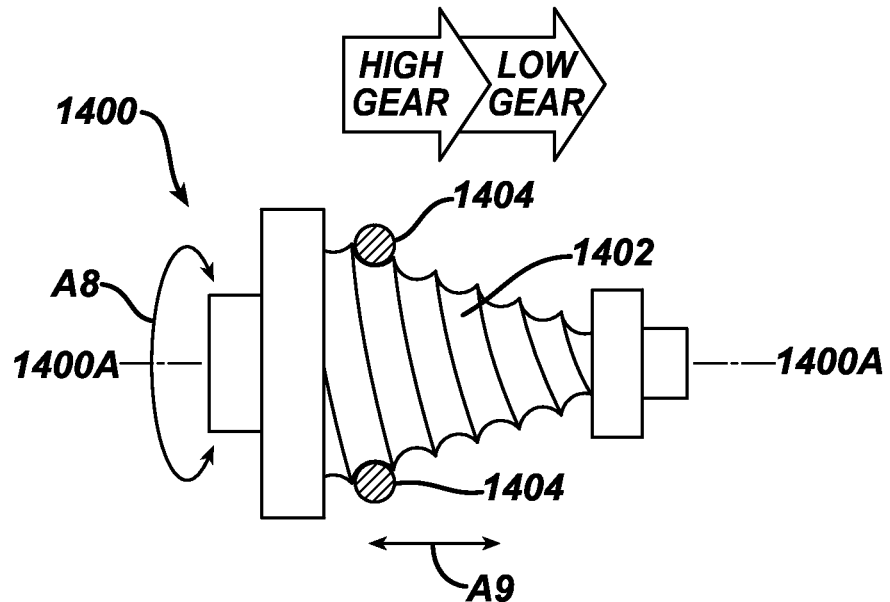
FIG. 50 is a side schematic view of an embodiment of a hub configured to dynamically provide varying amounts of power for closing and for opening an end effector of a surgical device, the hub having a belt coupled thereto.

FIG. 50 illustrates one embodiment of a hub 1400 configured to dynamically provide varying amounts of power for closing and for opening an end effector of a surgical device. The hub 1400 can include a continuous spline body 1402 coupled to a belt 1404. The hub 1400 can be configured to rotate about a longitudinal axis 1400A of the hub 1400, as shown by arrow A8. Actuating a closure trigger of the device can cause the hub 1400 to rotate. The belt 1404 can be configured to move longitudinally along the body 1402 in response to the rotation of the hub 1400, as shown by arrow A9. When the hub 1400 rotates in a first direction, the belt 1404 can be configured to translate in a first longitudinal direction based on a direction of the body 1402, and when the hub 1400 rotates in a second, opposite direction, the belt 1404 can be configured to translate in a second, opposite longitudinal direction based on the direction of the body 1402. In the illustrated embodiment, the belt 1404 is configured to move toward the low gear, e.g., toward the right of FIG. 49, when the hub 1400 rotates clockwise and to move toward the high gear, e.g., toward the left of FIG. 49, when the hub 1400 rotates counterclockwise. The body 1402 can have a varying diameter along the hub's longitudinal axis 1400A, with a smaller diameter at the low gear side of the hub 1400. The belt 1404 can be a flexible member configured to ride along a surface of the body 1402 along the body's varying diameter.

Figure 51:
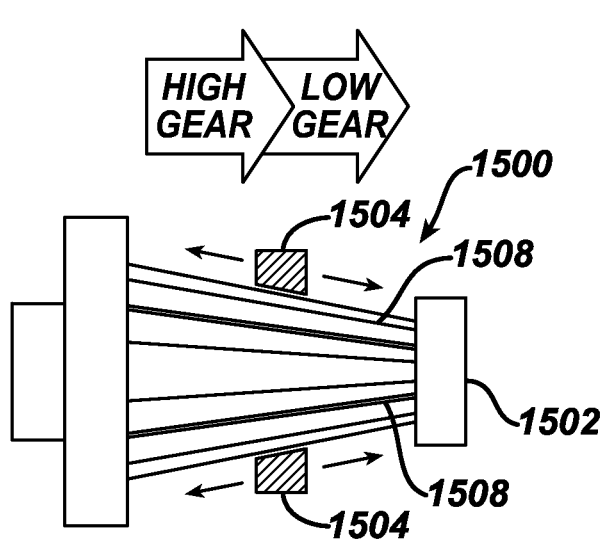
FIG. 51 is a side schematic view of another embodiment of a hub configured to dynamically provide varying amounts of power for closing and for opening an end effector of a surgical device, the hub having a belt coupled thereto.
Figure 52:
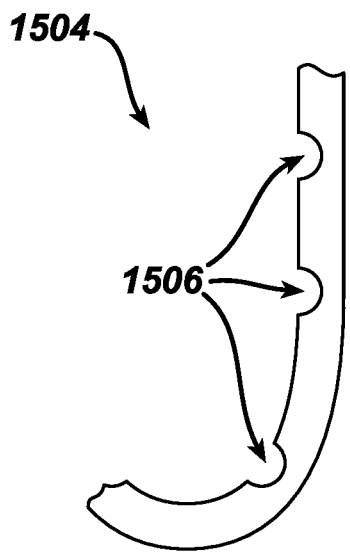
FIG. 52 is a side schematic view of the belt of FIG. 51.

FIG. 51 illustrates another embodiment of a hub 1500 configured to dynamically provide varying amounts of power for closing and for opening an end effector of a surgical device. The hub 1500 can include a ribbed body 1502 coupled to a belt 1504. The belt 1504 can include a plurality of grooves 1506 formed therein, as shown in FIG. 52, such that the belt 1504 is toothed. The grooves 1506 can have any size and shape. Each of the grooves 1506 can be configured to engage one of the plurality of ribs 1508 that extend longitudinally along the hub body 1502. Unlike the hub 1400 of FIG. 50, the hub 1500 of FIG. 51 does not rotate to move between high and low gears. The belt 1504 can be configured to move longitudinally along the hub 1502. The belt 1504 translating longitudinally in a first direction, e.g., toward the right in FIG. 51, can correspond to moving toward the low gear, and the belt 1504 translating longitudinally in a second, opposite longitudinal direction, e.g., toward the left in FIG. 51, can correspond to moving toward the high gear. The body 1502 can have a varying diameter along a longitudinal axis of the hub 1500, with a smaller diameter at the low gear side of the hub 1500. The belt 1504 can be a flexible member configured to ride along a surface of the body 1502 along the body's varying diameter. One end of the belt 1504 can be attached to a motor of the device, and the other end of the belt 1504 can be attached to the hub 1500. Actuating a closure trigger of the device can cause the belt 1504 to translate along the hub 1500.

The surgical devices disclosed herein can be used to perform a surgical procedure in which tissue is grasped and transected. The tissue can include, for example, stomach tissue, intestinal tissue, esophageal tissue, or blood vessels. The surgical procedure can be a minimally invasive procedure or an open surgical procedure. The surgical devices disclosed herein can be used in robotic-assisted minimally invasive or open surgical procedures.

For example, a minimally invasive surgical procedure can begin by preparing the patient for surgery and making one or more appropriately sized incisions at a desired location. In a minimally invasive procedure, one or more cannulas or trocars (not shown) can be positioned in the incision(s) to provide access to the surgical site. One or more viewing devices, e.g., scopes, can be placed in one of the incisions to allow medical personnel to view the surgical site from outside the body. Once the patient is prepared for surgery, a surgical device can be inserted through an incision and/or through a cannula, and an end effector of the surgical device can be positioned adjacent to a desired tissue to be treated. As the surgical device is being inserted into the patient, a closure grip of the surgical device can be disposed adjacent to a stationary grip of the surgical device so that the end effector is in a closed position and occupies a smaller amount of space than when in an open position. When the end effector is positioned adjacent to the tissue to be treated, the closure grip can be moved away from the stationary grip, and the tissue to be treated can be positioned between facing engagement surfaces of the end effector's jaws. Movement of the closure grip toward the stationary grip can close the jaws so that the engagement surfaces are in direct contact with the tissue and so that the tissue is securely grasped between the jaws. A position of the jaws can directly correspond to a position of the closure grip relative to the stationary grip. With the jaws having tissue grasped therebetween, a user can engage a firing actuator which can advance a cutting element to cut the grasped tissue and/or a compression member to further compress the grasped tissue. In another embodiment, the device can automatically cause a cutting element and/or a compression member to advance through the jaws. A person skilled in the art will appreciate that, optionally, energy can be applied to the tissue prior to or during transection of the tissue between the jaws. After the cutting element is advanced through the tissue and is retracted proximally, the device can continue to apply energy to the cut tissue or the jaws can automatically release the tissue.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a handle portion;
   a motor;
   an elongate shaft extending distally from the handle portion and having an end effector at a distal end thereof, the end effector being configured to engage tissue, and the motor being configured to supply power that causes the end effector to selectively open and close; and
   an actuator coupled to the handle portion and configured to have pressure applied thereto by a user input;
   wherein an amount of the pressure applied to the actuator defines an amount of the power supplied by the motor, and the amount of pressure applied to the actuator defines a drive direction of the motor; and
   wherein the amount of pressure applied to the actuator being in a first range of pressure defines a first amount of power supplied by the motor and defines a first drive direction of the motor, and the amount of pressure applied to the actuator being in a second range of pressure that is greater than the first range of pressure defines a second amount of power supplied by the motor that is greater than the first amount of power and defines a second drive direction of the motor that is opposite to the first direction.

2. The device of claim 1, wherein the amount of pressure applied to the actuator being in a third range of pressure that is less than the first range of pressure defines a third amount of power supplied by the motor that is less than the first amount of power.

3. The device of claim 1, wherein the amount of pressure applied to the actuator being in a third range of pressure that is greater than the first range of pressure and less than the second range of pressure defines a third amount of power supplied by the motor that is less than the first amount of power.

4. The device of claim 1, further comprising a sensor configured to sense the amount of pressure applied to the actuator; and
a controller configured to receive a signal from the sensor indicative of the sensed amount of pressure, and the controller being configured to use the signal to control the power supplied by the motor.

5. The device of claim 1, further comprising a compression member configured to translate along the end effector to selectively open and close the end effector.

6. The device of claim 5, wherein the motor driving in the first drive direction urges the compression member in a proximal direction, the motor driving in the second drive direction urges the compression member in a distal direction, and the amount of power supplied by the motor defines a movement speed of the compression member.

7. The device of claim 1, further comprising a cutting element configured to translate along the end effector in response to the power supplied by the motor.

8. The device of claim 1, wherein the actuator includes a movable trigger coupled to the handle portion.

9. A surgical device, comprising:
a motor;
an elongate shaft having first and second jaws at a distal end thereof, the first and second jaws being configured to engage tissue therebetween;
a compression member configured to translate relative to the first and second jaws;
an actuator configured to have pressure applied thereto by a user and thereby cause the motor to provide power that causes the compression member to translate along the first and second jaws;
a sensor configured to sense an amount of the pressure applied to the actuator; and
a controller configured to receive a signal from the sensor indicative of the sensed amount of pressure, and the controller being configured to use the signal to control the power provided by the motor that causes the translation of the compression member along the first and second jaws;
wherein when the sensed amount of pressure is within a first range of pressure the controller is configured to control the power provided by the motor such that the compression member translates proximally along the first and second jaws; and
wherein when the sensed amount of pressure is within a second range of pressure that is greater than the first range of pressure the controller is configured to control the power provided by the motor such that the compression member translates distally along the first and second jaws.

10. The device of claim 9, wherein when the sensed amount of pressure is within the first range of pressure the controller is configured to control the power provided by the motor such that the power decreases as the sensed amount of pressure increases, and when the sensed amount of pressure is within the second range of pressure the controller is configured to control the power provided by the motor such that the power increases as the sensed amount of pressure increases.

11. The device of claim 9, wherein when the sensed amount of pressure is within the first range of pressure the motor drives in a first direction, and when the sensed amount of pressure is within the second range of pressure the motor drives in a second direction that is opposite to the first direction.

12. The device of claim 9, wherein when the sensed amount of pressure is within a third range of pressure that is less than the first range of pressure the controller is configured to control the power provided by the motor such that the motor is not providing power.

13. The device of claim 9, wherein when the sensed amount of pressure is within a third range of pressure that is greater than the first range of pressure and less than the second range of pressure the controller is configured to control the power provided by the motor such that the motor is not providing power.

14. The device of claim 9, wherein the compression member translating distally along the first and second jaws urges the jaws closed, and the compression member translating proximally along the first and second jaws urges the jaws open.

15. The device of claim 9, wherein the compression member has a cutting element on a distal end thereof, and the compression member translating distally along the first and second jaws causes the cutting element to cut tissue engaged between the first and second jaws.

16. The device of claim 9, wherein the motor is operatively coupled to the compression member via a gear and rack.

17. The device of claim 9, wherein the compression member is at a distal end of a movable rod operatively coupled to the motor.

18. The device of claim 9, further comprising a handle portion from which the elongate shaft distally extends, and wherein the actuator includes a movable trigger coupled to the handle portion.

19. A surgical method, comprising:
engaging a tissue with first and second jaws of a surgical device;
sensing with a sensor an amount of pressure applied to an actuator of the surgical device; and
causing a motor to provide power that causes at least one of the first and second jaws to move, the sensed amount of the pressure defining an amount of the power provided by the motor, and the sensed amount of pressure applied defining a drive direction of the motor;
wherein the sensed amount of pressure being in a first range of pressure defines a first amount of rower provided by the motor and defines a first drive direction of the motor, and the sensed amount of pressure being in a second range of pressure that is greater than the first range of pressure defines a second amount of power provided by the motor that is greater than the first amount of power and defines a second drive direction of the motor that is opposite to the first direction.

20. The method of claim 19, wherein the amount of pressure applied to the actuator being in a third range of pressure that is less than the first range of pressure defines a third amount of power supplied by the motor that is less than the first amount of power; and the amount of pressure applied to the actuator being in a fourth range of pressure that is greater than the first range of pressure and less than the second range of pressure defines a fourth amount of power supplied by the motor that is less than the first amount of power.

\* \* \* \* \*